(12) United States Patent
Aruffo et al.

(10) Patent No.: US 6,312,693 B1
(45) Date of Patent: Nov. 6, 2001

(54) ANTIBODIES AGAINST HUMAN CD40

(76) Inventors: Alejandro A. Aruffo, 33 Cheston Ct., Belle Mead, NJ (US) 08502; Diane Hollenbaugh, 344 Wrights Rd., Newtown, PA (US) 18940; Anthony W. Siadak, 6210 First Ave. NW., Seattle, WA (US) 98107; Karen K. Berry, 1206 Sayre Dr., Princeton, NJ (US) 08540; Linda Harris, 1214 16$^{th}$ Ave. E., Seattle, WA (US) 98112; Barbara A. Thorne, 3626 223rd Ave. SE., Issaquah, WA (US) 98029; Jurgen Bajorath, 17406 37th Ave., Lynnwood, WA (US) 98037; William D. Huse, 1993 Zapo St., Del Mar, CA (US) 92014; Herren Wu, 5255 Timber Branch Way, San Diego, CA (US) 92130; Jeffry D. Watkins, 455 Jolina Way, Encinitas, CA (US) 92024

( * ) Notice: Subject to any disclaimer, the term of this patent is extended or adjusted under 35 U.S.C. 154(b) by 0 days.

(21) Appl. No.: 09/247,352

(22) Filed: Feb. 10, 1999

Related U.S. Application Data

(63) Continuation-in-part of application No. 09/026,291, filed on Feb. 19, 1998, now Pat. No. 6,051,228.

(51) Int. Cl.$^7$ ................. A61K 39/395; C07K 16/28; C12N 15/13
(52) U.S. Cl. ................. 424/154.1; 424/130.1; 424/133.1; 424/141.1; 424/143.1; 424/173.1; 530/387.1; 530/387.3; 530/388.1; 530/388.2; 530/388.22; 530/388.7; 530/388.73; 435/69.6; 435/455; 435/471; 435/326; 435/328; 435/332; 435/334; 435/343; 435/343.1; 435/252.2; 435/320.1; 536/23.1; 536/23.5; 536/23.53
(58) Field of Search ............ 424/130.1, 133.1, 424/144.1; 435/69.6, 326, 334, 252.3; 530/387.1, 388.2, 388.73; 536/23.1

(56) References Cited

U.S. PATENT DOCUMENTS 5,677,165  10/1997  de Boer et al. ............ 435/240
6,051,228 *  4/2000  Aruffo et al. .

OTHER PUBLICATIONS

Int. J. Cancer (1989) 43:786–94 Young et al.
Eur. J. Immunol. (1996) 26:2329–34 Denfeld et al.
Eur. J. Immunol. (1996) 26:1371–77 Gaspari et al.
J. Immunol. (1997) 158:144–52 Pequet–Navarro et al.
J. Exp. Med. (1995) 182:33–40 Hollenbaugh et al..
J. Immunol. (1992) 14:775–82 Galy and Spits.
J. Leukoc. Biol. (1995) 58:209–16 Yellin et al.
J. Clin. Invest. (1996) 97:1761–66 Ohkawara et al.
Science (1993) 259:990–93 Allen et al.
Cell (1993) 72:291–300 Aruffo et al.
Nature (1993) 361:541–43 Di Santo et al.
*Proc. Natl. Acad. Sci. USA (1993) 90(6):2170–73 Fuleihan et al.
Nature (1993) 361:539–541 Korthauer et al.
Immunity (1994) 1:167–78 Kawabe et al.
Immunity (1994) 1:423–431 Xu et al.
J. Exp. Med. (1994) 180:1889–1900 Renshaw et al.
Proc. Natl. Acad. Sci. USA (1996) 93:13967–72 Castigli et al.
J. Exp. Med. (1993) 178:1567–75 Foy et al.
Science (1993) 261:1328–30 Durie et al.
* Proc. Natl. Acad. Sci. USA (1995) 93:2499–504 Gerritse et al.
J. Immunol. (1995) 154:1470–1480 Mohan et al.
Transplantation (1996) 61:4–9 Larsen et al.
Proc. Natl. Acad. Sci. USA (1996) 93:13967–72 Hancock et al.
Proc. Natl. Acad. Sci. USA (1995) 92:9560–64 Parker et al.
J. Clin. Invest. (1994) 94:1333–38 Durie et al.
J. Immunol. (1995) 155:4917–25 Kiener et al.
J. Immunol. (1995) 156:3952–60 Malik et al.
J. Exp. Med. (1995) 182:33–40 Hollenbaugh et al.

* cited by examiner

*Primary Examiner*—Phillip Gambel
(74) *Attorney, Agent, or Firm*—Joan E. Switzer

(57) ABSTRACT

The Applicants have discovered humanized anti-human CD40 antibodies which block the interaction between gp39 and CD40. The anti-CD40 antibodies of the present invention are effective in modulating humoral immune responses against T cell-dependent antigens, collagen induced arthritis, and skin transplantation, and are also useful for their anti-inflammatory properties.

26 Claims, 22 Drawing Sheets

A) Light Chain Variable Region (SEQ ID NO:1).

MEAPAQLLFLLLLWLPDTTGDIVLTQSPATLSVTPGDRVSLSCRASQSISDYLHWYQQKS
HESPRLLIKYASHSISGIPSRFSGSGSGSDFTLSINSVEPEDVGIYYCQHGHSFPWTFGG
GTKLEIKR

B) Heavy Chain Variable Region (SEQ ID NO:2).

MDWTWRILFLVAAATGAHSQIQLVQSGPELKKPGETVRISCKASGYAFTTTGMQWVQEMP
GKGLKWIGWINTHSGVPKYVEDFKGRFAFSLETSANTAYLQISNLKNEDTATYFCVRSGN
GNYDLAYFAYWGQGTLVTVSA

FIG. 4

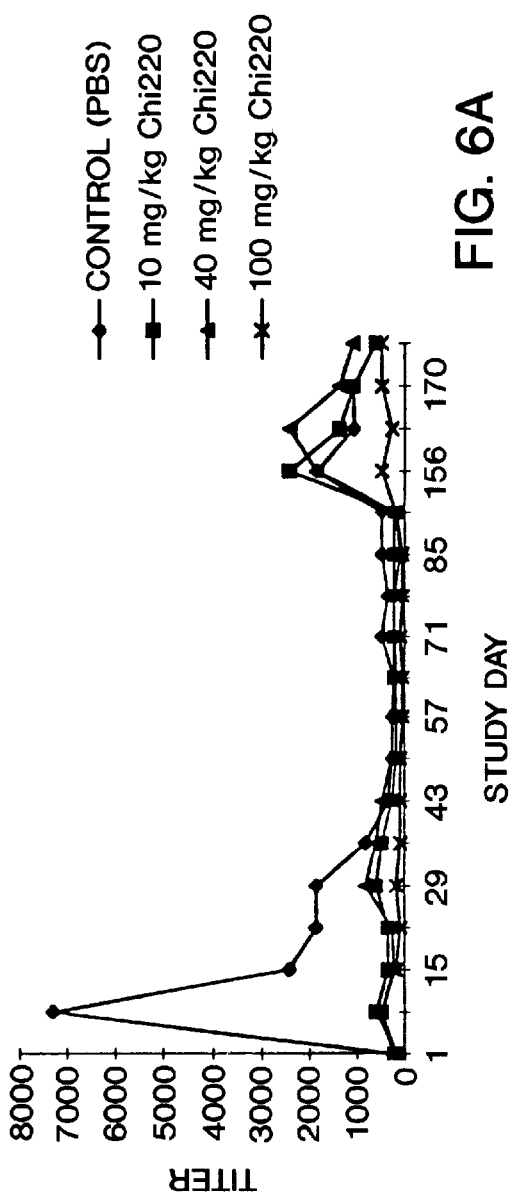
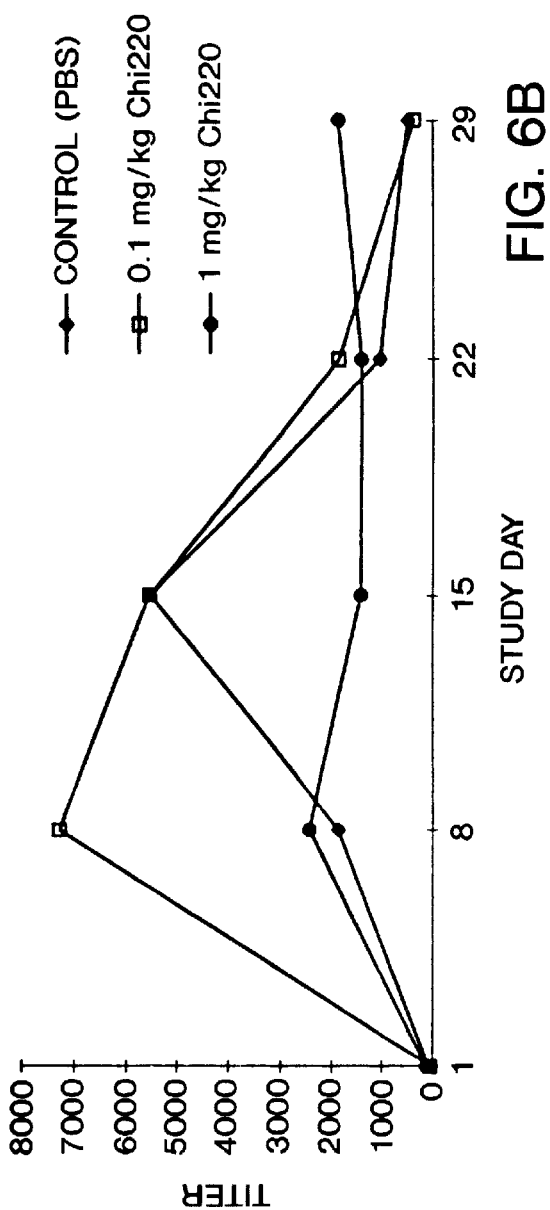
FIG. 6A
FIG. 6B

```
   1 GACGGATCGG GAGATCTGCT AGGTGACCTG AGGCGCGCCG GCTTCGAATA GCCAGAGTAA
  61 CCTTTTTTTT TAATTTTATT TTATTTTATT TTTGAGATGG AGTTTGGCGC CGATCTCCCG
 121 ATCCCCTATG GTCGACTCTC AGTACAATCT GCTCTGATGC CGCATAGTTA AGCCAGTATC
 181 TGCTCCCTGC TTGTGTGTTG GAGGTCGCTG AGTAGTGCGC GAGCAAAATT TAAGCTACAA
 241 CAAGGCAAGG CTTGACCGAC AATTGCATGA AGAATCTGCT TAGGGTTAGG CGTTTTGCGC
 301 TGCTTCGCGA TGTACGGGCC AGATATACGC GTTGACATTG ATTATTGACT AGTTATTAAT
 361 AGTAATCAAT TACGGGGTCA TTAGTTCATA GCCCATATAT GGAGTTCCGC GTTACATAAC
 421 TTACGGTAAA TGGCCCGCCT GGCTGACCGC CCAACGACCC CCGCCCATTG ACGTCAATAA
 481 TGACGTATGT TCCCATAGTA ACGCCAATAG GGACTTTCCA TTGACGTCAA TGGGTGGACT
 541 ATTTACGGTA AACTGCCCAC TTGGCAGTAC ATCAAGTGTA TCATATGCCA AGTACGCCCC
 601 CTATTGACGT CAATGACGGT AAATGGCCCG CCTGGCATTA TGCCCAGTAC ATGACCTTAT
 661 GGGACTTTCC TACTTGGCAG TACATCTACG TATTAGTCAT CGCTATTACC ATGGTGATGC
 721 GGTTTTGGCA GTACATCAAT GGGCGTGGAT AGCGGTTTGA CTCACGGGA TTTCCAAGTC
 781 TCCACCCCAT TGACGTCAAT GGGAGTTTGT TTTGGCACCA AAATCAACGG GACTTTCCAA
 841 AATGTCGTAA CAACTCCGCC CCATTGACGC AAATGGGCGG TAGGCGTGTA CGGTGGGAGG
 901 TCTATATAAG CAGAGCTCTC TGGCTAACTA GAGAACCCAC TGCTTACTGG CTTATCGAAA
 961 TTAATACGAC TCACTATAGG GAGACCCAAG CTTGGTACCA TGGACTGGAC CTGGAGAATC
1021 CTCTTCTTGG TGGCAGCAGC AACAGGTGCC CACTCCCAGA TCCAGTTGGT GCAATCTGGA
1081 CCTGAGCTGA AGAAGCCTGG AGAGACAGTC AGGATCTCCT GCAAGGCTTC TGGGTATGCC
1141 TTCACAACTA CTGGAATGCA GTGGGTGCAA GAGATGCCAG GAAAGGGTTT GAAGTGGATT
1201 GGCTGGATAA ACACCCACTC TGGAGTGCCA AAATATGTAG AAGACTTCAA GGGACGGTTT
1261 GCCTTCTCTT TGGAAACCTC TGCCAACACT GCATATTTAC AGATAAGCAA CCTCAAAAAT
1321 GAGGACACGG CTACGTATTT CTGTGTGAGA TCCGGGAATG GTAACTATGA CCTGGCCTAC
1381 TTTGCTTACT GGGGCCAAGG GACACTGGTC ACTGTCTCTG CAGCTAGCAC CAAGGGCCCA
1441 TCGGTCTTCC CCCTGGCACC CTCCTCCAAG AGCACCTCTG GGGGCACAGC GGCCCTGGGC
1501 TGCCTGGTCA AGGACTACTT CCCCGAACCG GTGACGGTGT CGTGGAACTC AGGCGCCCTG
1561 ACCAGCGGCG TGCACACCTT CCCGGCTGTC CTACAGTCCT CAGGACTCTA CTCCCTCAGC
1621 AGCGTGGTGA CCGTGCCCTC CAGCAGCTTG GGCACCCAGA CCTACATCTG CAACGTGAAT
1681 CACAAGCCCA GCAACACCAA GGTGGACAAG AAAGTTGGTG AGAGGCCAGC ACAGGGAGGG
1741 AGGGTGTCTG CTGGAAGCCA GGCTCAGCGC TCCTGCCTGG ACGCATCCCG GCTATGCAGC
1801 CCCAGTCCAG GGCAGCAAGG CAGGCCCCGT CTGCCTCTTC ACCCGGAGGC CTCTGCCCGC
1861 CCCACTCATG CTCAGGGAGA GGGTCTTCTG GCTTTTTCCC CAGGCTCTGG GCAGGCACAG
1921 GCTAGGTGCC CCTAACCCAG GCCCCACACA CAAAGGGGCA GGTGCTGGGC TCAGACCTGC
1981 CAAGAGCCAT ATCCGGGAGG ACCCTGCCCC TGACCTAAGC CCACCCCAAA GGCCAAACTC
2041 TCCACTCCCT CAGCTCGGAC ACCTTCTCTC CTCCCAGATT CCAGTAACTC CCAATCTTCT
2101 CTCTGCAGAG CCCAAATCTT GTGACAAAAC TCACACATGC CCACCGTGCC CAGGTAAGCC
2161 AGCCCAGGCC TCGCCCTCCA GCTCAAGGCG GGACAGGTGC CCTAGAGTAG CCTGCATCCA
2221 GGGACAGGCC CCAGCCGGGT GCTGACACGT CCACCTCCAT CTCTTCCTCA GCACCTGAAC
2281 TCCTGGGGGG ACCGTCAGTC TTCCTCTTCC CCCCAAAACC CAAGGACACC CTCATGATCT
2341 CCCGGACCCC TGAGGTCACA TGCGTGGTGG TGGACGTGAG CCACGAAGAC CCTGAGGTCA
2401 AGTTCAACTG GTACGTGGAC GGCGTGGAGG TGCATAATGC CAAGACAAAG CCGCGGGAGG
2461 AGCAGTACAA CAGCACGTAC CGTGTGGTCA GCGTCCTCAC CGTCCTGCAC CAGGACTGGC
2521 TGAATGGCAA GGAGTACAAG TGCAAGGTCT CCAACAAAGC CCTCCCAGCC CCCATCGAGA
2581 AAACCATCTC CAAAGCCAAA GGTGGGACCC GTGGGGTGCG AGGGCCACAT GGACAGAGGC
2641 CGGCTCGGCC CACCCTCTGC CCTGAGAGTG ACCGCTGTAC CAACCTCTGT CCCTACAGGG
2701 CAGCCCCGAG AACCACAGGT GTACACCCTG CCCCCATCCC GGGATGAGCT GACCAAGAAC
2761 CAGGTCAGCC TGACCTGCCT GGTCAAAGGC TTCTATCCCA GCGACATCGC CGTGGAGTGG
2821 GAGAGCAATG GGCAGCCGGA GAACAACTAC AAGACCACGC CTCCCGTGCT GGACTCCGAC
2881 GGCTCCTTCT TCCTCTACAG CAAGCTCACC GTGGACAAGA GCAGGTGGCA GCAGGGGAAC
2941 GTCTTCTCAT GCTCCGTGAT GCATGAGGCT CTGCACAACC ACTACACGCA GAAGAGCCTC
3001 TCCCTGTCTC CGGGTAAATG AGTGCGACGG CCGGCAAGCC CCCGCTCCCC GGGCTCTCGC
```

FIG. 13A

```
3061 GGTCGCACGA GGATGCTTGG CACGTACCCC CTGTACATAC TTCCCGGGCG CCCAGCATGG
3121 AAATAAAGCA CCCAGCGCTG CCCTGGGCCC CTGCGAGACT GTGATGGTTC TTTCCACGGG
3181 TCAGGCCGAG TCTGAGGCCT GAGTGGCATG AGGGAGGCAG AGCGGGTCCC ACTGTCCCCA
3241 CACTGGCCCA GGCTGTGCAG GTGTGCCTGG GCCCCTAGG GTGGGGCTCA GCCAGGGGCT
3301 GCCCTCGGCA GGGTGGGGGA TTTGCCAGCG TGGCCCTCCC TCCAGCAGCA CCTGCCCTGG
3361 GCTGGGCCAC GGGAAGCCCT AGGAGCCCCT GGGGACAGAC ACACAGCCCC TGCCTCTGTA
3421 GGAGACTGTC CTGTTCTGTG AGCGCCCCTG TCCTCCCGAC CTCCATGCCC ACTCGGGGGC
3481 ATGCCTAGTC CATGTGCGTA GGGACAGGCC CTCCCTCACC CATCTACCCC CACGGCACTA
3541 ACCCCTGGCT GCCCTGCCCA GCCTCGCACC CGCATGGGGA CACAACCGAC TCCGGGGACA
3601 TGCACTCTCG GGCCCTGTGG AGGGACTGGT GCAGATGCCC ACACACACAC TCAGCCCAGA
3661 CCCGTTCAAC AAACCCCGCA CTGAGGTTGG CCGGCCACAC GGCCACCACA CACACACGTG
3721 CACGCCTCAC ACACGGAGCC TCACCCGGGC GAACTGCACA GCACCCAGAC CAGAGCAAGG
3781 TCCTCGCACA CGTGAACACT CCTCGGACAC AGGCCCCCAC GAGCCCACG CGGCACCTCA
3841 AGGCCCACGA GCCTCTCGGC AGCTTCTCCA CATGCTGACC TGCTCAGACA AACCCAGCCC
3901 TCCTCTCACA AGGGTGCCCC TGCAGCCGCC ACACACACAC AGGGGATCAC ACACCACGTC
3961 ACGTCCCTGG CCCTGGCCCA CTTCCCAGTG CCGCCCTTCC CTGCAGGACG GATCAGCCTC
4021 GACTGTGCCT TCTAGTTGCC AGCCATCTGT TGTTTGCCCC TCCCCGTGC CTTCCTTGAC
4081 CCTGGAAGGT GCCACTCCCA CTGTCCTTTC CTAATAAAAT GAGGAAATTG CATCGCATTG
4141 TCTGAGTAGG TGTCATTCTA TTCTGGGGGG TGGGGTGGGG CAGGACAGCA AGGGGGAGGA
4201 TTGGGAAGAC AATAGCAGGC ATGCTGGGA TGCGGTGGGC TCTATGGCTT CTGAGGCGGA
4261 AAGAACCAGC TGGGGCTCTA GGGGGTATCC CCACGCGCCC TGTAGCGGCG CATTAAGCGC
4321 GGCGGGTGTG GTGGTTACGC GCAGCGTGAC CGCTACACTT GCCAGCGCCC TAGCGCCCGC
4381 TCCTTTCGCT TTCTTCCCTT CCTTTCTCGC CACGTTCGCC GGGCCTCTCA AAAAAGGGAA
4441 AAAAAGCATG CATCTCAATT AGTCAGCAAC CATAGTCCCG CCCTAACTC CGCCCATCCC
4501 GCCCCTAACT CCGCCCAGTT CCGCCCATTC TCCGCCCCAT GGCTGACTAA TTTTTTTTAT
4561 TTATGCAGAG GCCGAGGCCG CCTCGGCCTC TGAGCTATTC CAGAAGTAGT GAGGAGGCTT
4621 TTTTGGAGGC CTAGGCTTTT GCAAAAAGCT TGGACAGCTC AGGGCTGCGA TTTCGCGCCA
4681 AACTTGACGG CAATCCTAGC GTGAAGGCTG GTAGGATTTT ATCCCCGCTG CCATCATGGT
4741 TCGACCATTG AACTGCATCG TCGCCGTGTC CCAAAATATG GGGATTGGCA AGAACGGAGA
4801 CCTACCCTGG CCTCCGCTCA GGAACGAGTT CAAGTACTTC CAAAGAATGA CCACAACCTC
4861 TTCAGTGGAA GGTAAACAGA ATCTGGTGAT TATGGGTAGG AAAACCTGGT TCTCCATTCC
4921 TGAGAAGAAT CGACCTTTAA AGGACAGAAT TAATATAGTT CTCAGTAGAG AACTCAAAGA
4981 ACCACCACGA GGAGCTCATT TTCTTGCCAA AAGTTTGGAT GATGCCTTAA GACTTATTGA
5041 ACAACCGGAA TTGGCAAGTA AAGTAGACAT GGTTTGGATA GTCGGAGGCA GTTCTGTTTA
5101 CCAGGAAGCC ATGAATCAAC CAGGCCACCT TAGACTCTTT GTGACAAGGA TCATGCAGGA
5161 ATTTGAAAGT GACACGTTTT TCCCAGAAAT TGATTTGGGG AAATATAAAC TTCTCCCAGA
5221 ATACCCAGGC GTCCTCTCTG AGGTCCAGGA GGAAAAAGGC ATCAAGTATA AGTTTGAAGT
5281 CTACGAGAAG AAAGACTAAC AGGAAGATGC TTTCAAGTTC TCTGCTCCCC TCCTAAAGCT
5341 ATGCATTTTT ATAAGACCAT GGGACTTTTG CTGGCTTTAG ATCTCTTTGT GAAGGAACCT
5401 TACTTCTGTG GTGTGACATA ATTGGACAAA CTACCTACAG AGATTTAAAG CTCTAAGGTA
5461 AATATAAAAT TTTTAAGTGT ATAATGTGTT AAACTACTGA TTCTAATTGT TTGTGTATTT
5521 TAGATTCCAA CCTATGGAAC TGATGAATGG GAGCAGTGGT GGAATGCCTT TAATGAGGAA
5581 AACCTGTTTT GCTCAGAAGA AATGCCATCT AGTGATGATG AGGCTACTGC TGACTCTCAA
5641 CATTCTACTC CTCCAAAAAA GAAGAGAAAG GTAGAAGACC CAAGGACTT TCCTTCAGAA
5701 TTGCTAAGTT TTTTGAGTCA TGCTGTGTTT AGTAATAGAA CTCTTGCTTG CTTTGCTATT
5761 TACACCACAA AGGAAAAAGC TGCACTGCTA TACAAGAAAA TTATGGAAAA ATATTCTGTA
5821 ACCTTTATAA GTAGGCATAA CAGTTATAAT CATAACATAC TGTTTTTTCT TACTCCACAC
5881 AGGCATAGAG TGTCTGCTAT TAATAACTAT GCTCAAAAAT TGTGTACCTT TAGCTTTTTA
5941 ATTTGTAAAG GGGTTAATAA GGAATATTTG ATGTATAGTG CCTTGACTAG AGATCATAAT
6001 CAGCCATACC ACATTTGTAG AGGTTTTACT TGCTTTAAAA AACCTCCCAC ACCTCCCCCT
6061 GAACCTGAAA CATAAAATGA ATGCAATTGT TGTTGTTAAC TTGTTTATTG CAGCTTATAA
```

FIG. 13B

```
6121 TGGTTACAAA TAAAGCAATA GCATCACAAA TTTCACAAAT AAAGCATTTT TTTCACTGCA
6181 TTCTAGTTGT GGTTTGTCCA AACTCATCAA TGTATCTTAT CATGTCTGGA TCGGCTGGAT
6241 GATCCTCCAG CGCGGGGATC TCATGCTGGA GTTCTTCGCC CACCCCAACT TGTTTATTGC
6301 AGCTTATAAT GGTTACAAAT AAAGCAATAG CATCACAAAT TTCACAAATA AAGCATTTTT
6361 TTCACTGCAT TCTAGTTGTG GTTTGTCCAA ACTCATCAAT GTATCTTATC ATGTCTGTAT
6421 ACCGTCGACC TCTAGCTAGA GCTTGGCGTA ATCATGGTCA TAGCTGTTTC CTGTGTGAAA
6481 TTGTTATCCG CTCACAATTC CACACAACAT ACGAGCCGGA AGCATAAAGT GTAAAGCCTG
6541 GGGTGCCTAA TGAGTGAGCT AACTCACATT AATTGCGTTG CGCTCACTGC CCGCTTTCCA
6601 GTCGGGAAAC CTGTCGTGCC AGCTGCATTA ATGAATCGGC CAACGCGCGG GGAGAGGCGG
6661 TTTGCGTATT GGGCGCTCTT CCGCTTCCTC GCTCACTGAC TCGCTGCGCT CGGTCGTTCG
6721 GCTGCGGCGA GCGGTATCAG CTCACTCAAA GGCGGTAATA CGGTTATCCA CAGAATCAGG
6781 GGATAACGCA GGAAAGAACA TGTGAGCAAA AGGCCAGCAA AAGGCCAGGA ACCGTAAAAA
6841 GGCCGCGTTG CTGGCGTTTT TCCATAGGCT CCGCCCCCCT GACGAGCATC ACAAAAATCG
6901 ACGCTCAAGT CAGAGGTGGC GAAACCCGAC AGGACTATAA AGATACCAGG CGTTTCCCCC
6961 TGGAAGCTCC CTCGTGCGCT CTCCTGTTCC GACCCTGCCG CTTACCGGAT ACCTGTCCGC
7021 CTTTCTCCCT TCGGGAAGCG TGGCGCTTTC TCAATGCTCA CGCTGTAGGT ATCTCAGTTC
7081 GGTGTAGGTC GTTCGCTCCA AGCTGGGCTG TGTGCACGAA CCCCCCGTTC AGCCCGACCG
7141 CTGCGCCTTA TCCGGTAACT ATCGTCTTGA GTCCAACCCG GTAAGACACG ACTTATCGCC
7201 ACTGGCAGCA GCCACTGGTA ACAGGATTAG CAGAGCGAGG TATGTAGGCG GTGCTACAGA
7261 GTTCTTGAAG TGGTGGCCTA ACTACGGCTA CACTAGAAGG ACAGTATTTG GTATCTGCGC
7321 TCTGCTGAAG CCAGTTACCT TCGGAAAAAG AGTTGGTAGC TCTTGATCCG GCAAACAAAC
7381 CACCGCTGGT AGCGGTGGTT TTTTTGTTTG CAAGCAGCAG ATTACGCGCA GAAAAAAAGG
7441 ATCTCAAGAA GATCCTTTGA TCTTTTCTAC GGGGTCTGAC GCTCAGTGGA ACGAAAACTC
7501 ACGTTAAGGG ATTTTGGTCA TGAGATTATC AAAAAGGATC TTCACCTAGA TCCTTTTAAA
7561 TTAAAAATGA AGTTTTAAAT CAATCTAAAG TATATATGAG TAAACTTGGT CTGACAGTTA
7621 CCAATGCTTA ATCAGTGAGG CACCTATCTC AGCGATCTGT CTATTTCGTT CATCCATAGT
7681 TGCCTGACTC CCCGTCGTGT AGATAACTAC GATACGGGAG GGCTTACCAT CTGGCCCCAG
7741 TGCTGCAATG ATACCGCGAG ACCCACGCTC ACCGGCTCCA GATTTATCAG CAATAAACCA
7801 GCCAGCCGGA AGGGCCGAGC GCAGAAGTGG TCCTGCAACT TTATCCGCCT CCATCCAGTC
7861 TATTAATTGT TGCCGGGAAG CTAGAGTAAG TAGTTCGCCA GTTAATAGTT TGCGCAACGT
7921 TGTTGCCATT GCTACAGGCA TCGTGGTGTC ACGCTCGTCG TTTGGTATGG CTTCATTCAG
7981 CTCCGGTTCC CAACGATCAA GGCGAGTTAC ATGATCCCCC ATGTTGTGCA AAAAAGCGGT
8041 TAGCTCCTTC GGTCCTCCGA TCGTTGTCAG AAGTAAGTTG GCCGCAGTGT TATCACTCAT
8101 GGTTATGGCA GCACTGCATA ATTCTCTTAC TGTCATGCCA TCCGTAAGAT GCTTTTCTGT
8161 GACTGGTGAG TACTCAACCA AGTCATTCTG AGAATAGTGT ATGCGGCGAC CGAGTTGCTC
8221 TTGCCCGGCG TCAATACGGG ATAATACCGC GCCACATAGC AGAACTTTAA AAGTGCTCAT
8281 CATTGGAAAA CGTTCTTCGG GGCGAAAACT CTCAAGGATC TTACCGCTGT TGAGATCCAG
8341 TTCGATGTAA CCCACTCGTG CACCCAACTG ATCTTCAGCA TCTTTTACTT TCACCAGCGT
8401 TTCTGGGTGA GCAAAAACAG GAAGGCAAAA TGCCGCAAAA AAGGGAATAA GGGCGACACG
8461 GAAATGTTGA ATACTCATAC TCTTCCTTTT TCAATATTAT TGAAGCATTT ATCAGGGTTA
8521 TTGTCTCATG AGCGGATACA TATTTGAATG TATTTAGAAA AATAAACAAA TAGGGGTTCC
8581 GCGCACATTT CCCCGAAAAG TGCCACCTGA CGTC
```

FIG. 13C

```
   1 GACGGATCGG GAGATCTGCT AGCCCGGGTG ACCTGAGGCG CGCCGGCTTC GAATAGCCAG
  61 AGTAACCTTT TTTTTTAATT TTATTTTATT TTATTTTTGA GATGGAGTTT GGCGCCGATC
 121 TCCCGATCCC CTATGGTCGA CTCTCAGTAC AATCTGCTCT GATGCCGCAT AGTTAAGCCA
 181 GTATCTGCTC CCTGCTTGTG TGTTGGAGGT CGCTGAGTAG TGCGCGAGCA AAATTTAAGC
 241 TACAACAAGG CAAGGCTTGA CCGACAATTG CATGAAGAAT CTGCTTAGGG TTAGGCGTTT
 301 TGCGCTGCTT CGCGATGTAC GGGCCAGATA TACGCGTTGA CATTGATTAT TGACTAGTTA
 361 TTAATAGTAA TCAATTACGG GGTCATTAGT TCATAGCCCA TATATGGAGT TCCGCGTTAC
 421 ATAACTTACG GTAAATGGCC CGCCTGGCTG ACCGCCCAAC GACCCCGCC CATTGACGTC
 481 AATAATGACG TATGTTCCCA TAGTAACGCC AATAGGGACT TTCCATTGAC GTCAATGGGT
 541 GGACTATTTA CGGTAAACTG CCCACTTGGC AGTACATCAA GTGTATCATA TGCCAAGTAC
 601 GCCCCCTATT GACGTCAATG ACGGTAAATG GCCCGCCTGG CATTATGCCC AGTACATGAC
 661 CTTATGGGAC TTTCCTACTT GGCAGTACAT CTACGTATTA GTCATCGCTA TTACCATGGT
 721 GATGCGGTTT TGGCAGTACA TCAATGGGCG TGGATAGCGG TTTGACTCAC GGGGATTTCC
 781 AAGTCTCCAC CCCATTGACG TCAATGGGAG TTTGTTTTGG CACCAAAATC AACGGGACTT
 841 TCCAAAATGT CGTAACAACT CCGCCCCATT GACGCAAATG GGCGGTAGGC GTGTACGGTG
 901 GGAGGTCTAT ATAAGCAGAG CTCTCTGGCT AACTAGAGAA CCCACTGCTT ACTGGCTTAT
 961 CGAAATTAAT ACGACTCACT ATAGGGAGAC CCAAGCTTGG TACCATGGAA GCCCAGCTC
1021 AGCTTCTCTT CCTCCTGCTA CTCTGGCTCC CAGATACCAC CGGAGACATT GTTCTGACTC
1081 AGTCTCCAGC CACCCTGTCT GTGACTCCAG GAGATAGAGT CTCTCTTTCC TGCAGGGCCA
1141 GCCAGAGTAT TAGCGACTAC TTACACTGGT ATCAACAAAA ATCACATGAG TCTCCAAGGC
1201 TTCTCATCAA ATATGCTTCC CATTCCATCT CTGGGATCCC CTCCAGGTTC AGTGGCAGTG
1261 GATCAGGGTC AGATTTCACT CTCAGTATCA ACAGTGTGGA ACCTGAAGAT GTTGAATTT
1321 ATTACTGTCA ACATGGTCAC AGCTTTCCGT GGACGTTCGG TGGAGGCACC AAGCTGGAAA
1381 TCAAACGTAA GTCTCGAGTC TCTAGATAAC CGGTCAATCG GTCAATCGAT TGGAATTCTA
1441 AACTCTGAGG GGGTCGGATG ACGTGGCCAT TCTTTGCCTA AAGCATTGAG TTTACTGCAA
1501 GGTCAGAAAA GCATGCAAAG CCCTCAGAAT GGCTGCAAAG AGCTCCAACA AAACAATTTA
1561 GAACTTTATT AAGGAATAGG GGGAAGCTAG GAAGAAACTC AAAACATCAA GATTTTAAAT
1621 ACGCTTCTTG GTCTCCTTGC TATAATTATC TGGGATAAGC ATGCTGTTTT CTGTCTGTCC
1681 CTAACATGCC CTTATCCGCA AACAACACAC CCAAGGGCAG AACTTTGTTA CTTAAACACC
1741 ATCCTGTTTG CTTCTTTCCT CAGGAACTGT GGCTGCACCA TCTGTCTTCA TCTTCCCGCC
1801 ATCTGATGAG CAGTTGAAAT CTGGAACTGC CTCTGTTGTG TGCCTGCTGA ATAACTTCTA
1861 TCCCAGAGAG GCCAAAGTAC AGTGGAAGGT GGATAACGCC CTCCAATCGG GTAACTCCCA
1921 GGAGAGTGTC ACAGAGCAGG ACAGCAAGGA CAGCACCTAC AGCCTCAGCA GCACCCTGAC
1981 GCTGAGCAAA GCAGACTACG AGAAACACAA AGTCTACGCC TGCGAAGTCA CCCATCAGGG
2041 CCTGAGCTCG CCCGTCACAA AGAGCTTCAA CAGGGGAGAG TGTTAGAGGG AGAAGTGCCC
2101 CCACCTGCTC CTCAGTTCCA GCCTGACCCC CTCCCATCCT TTGGCCTCTG ACCCTTTTTC
2161 CACAGGGGAC CTACCCCTAT TGCGGTCCTC CAGCTCATCT TTCACCTCAC CCCCCTCCTC
2221 CTCCTTGGCT TTAATTATGC TAATGTTGGA GGAGAATGAA TAAATAAAGT GAATCTTTGC
2281 ACCTGTGGTT TCTCTCTTTC CTCATTTAAT AATTATTATC TGTTGTTTTA CCAACTACTC
2341 AATTTCTCTT ATAAGGGACT AAATATGTAG TCATCCTAAG GCACGTAACC ATTTATAAAA
2401 ATCATCCTTC ATTCTATTTT ACCCTATCAT CCTCTGCAAG ACAGTCCTCC CTCAAACCCA
2461 CAAGCCTTCT GTCCTCACAG TCCCCTGGGC CATGGTAGGA GAGACTTGCT TCCTTGTTTT
2521 CCCCTCCTCA GCAAGCCCTC ATAGTCCTTT TTAAGGGTGA CAGGTCTTAC AGTCATATAT
2581 CCTTTGATTC AATTCCCTGA GAATCAACCA AAGCAAATTT TTCAAAAGAA GAAACCTGCT
2641 ATAAAGAGAA TCATTCATTG CAACATGATA TAAAATAACA ACACAATAAA AGCAATTAAA
2701 TAAACAAACA ATAGGGAAAT GTTTAAGTTC ATCATGGTAC TTAGACTTAA TGGAATGTCA
2761 TGCCTTATTT ACATTTTTAA ACAGGTACTG AGGGACTCCT GTCTGCCAAG GGCCGTATTG
2821 AGTACTTTCC ACAACCTAAT TTAATCCACA CTATACTGTG AGATTAAAAA CATTCATTAA
2881 AATGTTGCAA AGGTTCTATA AAGCTGAGAG ACAAATATAT TCTATAACTC AGCAATCCCA
2941 CTTCTAGATG ACTGAGTGTC CCCACCCACC AAAAAACTAT GCAAGAATGT TCAAAGCAGC
3001 TTTATTTACA AAAGCCAAAA ATTGGAAATA GCCCGATTGT CCAACAATAG AATGAGTTAT
```

FIG. 14A

```
3061 TAAACTGTGG TATGTTTATA CATTAGAATA CCCAATGAGG AGAATTAACA AGCTACAACT
3121 ATACCTACTC ACACAGATGA ATCTCATAAA AATAATGTTA CATAAGAGAA ACTCAATGCA
3181 AAAGATATGT TCTGTATGTT TTCATCCATA TAAAGTTCAA AACCAGGTAA AAATAAAGTT
3241 AGAAATTTGG ATGGAAATTA CTCTTAGCTG GGGGTGGGCG AGTTAGTGCC TGGGAGAAGA
3301 CAAGAAGGGG CTTCTGGGGT CTTGGTAATG TTCTGTTCCT CGTGTGGGGT TGTGCAGTTA
3361 TGATCTGTGC ACTGTTCTGT ATACACATTA TGCTTCAAAA TAACTTCACA TAAAGAACAT
3421 CTTATACCCA GTTAATAGAT AGAAGAGGAA TAAGTAATAG GTCAAGACCA ACGCAGCTGG
3481 TAAGTGGGGG CCTGGGATCA AATAGCTACC TGCCTAATCC TGCCCWCTTG AGCCCTGAAT
3541 GAGTCTGCCT TCCAGGGCTC AAGGTGCTCA ACAAAACAAC AGGCCTGCTA TTTTCCTGGC
3601 ATCTGTGCCC TGTTTGGCTA GCTAGGAGCA CACATACATA GAAATTAAAT GAAACAGACC
3661 TTCAGCAAGG GGACAGAGGA CAGAATTAAC CTTGCCCAGA CACTGGAAAC CCATGTATGA
3721 ACACTCACAT GTTTGGGAAG GGGGAAGGGC ACATGTAAAT GAGGACTCTT CCTCATTCTA
3781 TGGGGCACTC TGGCCCTGCC CCTCTCAGCT ACTCATCCAT CCAACACACC TTTCTAAGTA
3841 CCTCTCTCTG CCTACACTCT GAAGGGGTTC AGGAGTAACT AACACAGCAT CCCTTCCCTC
3901 AAATGACTGA CAATCCCTTT GTCCTGCTTT GTTTTTCTTT CCAGTCAGTA CTGGGAAAGT
3961 GGGGAAGGAC AGTCATGGAG AAACTACATA AGGAAGCACC TTGCCCTTCT GCCTCTTGAG
4021 AATGTTGATG AGTATCAAAT CTTTCAAACT TTGGAGGTTT GAGTAGGGGT GAGACTCAGT
4081 AATGTCCCTT CCAATGACAT GAACTTGCTC ACTCATCCCT GGGGGCCAAA TTGAACAATC
4141 AAAGGCAGGC ATAATCCAGT TATGAATTCT TGCGGCCGCT TGCTAGCTTC ACGTGTTGGA
4201 TCCAACCGCG GAAGGCCCCT ATTCTATAGT GTCACCTAAA TGCTAGAGCT CGCTGATCAG
4261 CCTCGACTGT GCCTTCTAGT TGCCAGCCAT CTGTTGTTTG CCCCTCCCCC GTGCCTTCCT
4321 TGACCCTGGA AGGTGCCACT CCCACTGTCC TTTCCTAATA AAATGAGGAA ATTGCATCGC
4381 ATTGTCTGAG TAGGTGTCAT TCTATTCTGG GGGTGGGGT GGGGCAGGAC AGCAAGGGGG
4441 AGGATTGGGA AGACAATAGC AGGCATGCTG GGGATGCGGT GGGCTCTATG GCTTCTGAGG
4501 CGGAAAGAAC CAGCTGGGGC TCTAGGGGGT ATCCCCACGC GCCCTGTAGC GGCGCATTAA
4561 GCGCGGCGGG TGTGGTGGTT ACGCGCAGCG TGACCGCTAC ACTTGCCAGC GCCCTAGCGC
4621 CCGCTCCTTT CGCTTTCTTC CCTTCCTTTC TCGCCACGTT CGCCGGGCCT CTCAAAAAAG
4681 GGAAAAAAAG CATGCATCTC AATTAGTCAG CAACCATAGT CCCGCCCTA ACTCCGCCCA
4741 TCCCGCCCCT AACTCCGCCC AGTTCCGCCC ATTCTCCGCC CCATGGCTGA CTAATTTTTT
4801 TTATTTATGC AGAGGCCGAG GCCGCCTCGG CCTCTGAGCT ATTCCAGAAG TAGTGAGGAG
4861 GCTTTTTTGG AGGCCTAGGC TTTTGCAAAA AGCTTGGACA GCTCAGGGCT GCGATTTCGC
4921 GCCAAACTTG ACGGCAATCC TAGCGTGAAG GCTGTAGGA TTTTATCCCC GCTGCCATCA
4981 TGGTTCGACC ATTGAACTGC ATCGTCGCCG TGTCCCAAAA TATGGGGATT GGCAAGAACG
5041 GAGACCTACC CTGGCCTCCG CTCAGGAACG AGTTCAAGTA CTTCCAAAGA ATGACCACAA
5101 CCTCTTCAGT GGAAGGTAAA CAGAATCTGG TGATTATGGG TAGGAAAACC TGGTTCTCCA
5161 TTCCTGAGAA GAATCGACCT TTAAAGGACA GAATTAATAT AGTTCTCAGT AGAGAACTCA
5221 AAGAACCACC ACGAGGAGCT CATTTCTTG CCAAAAGTTT GGATGATGCC TTAAGACTTA
5281 TTGAACAACC GGAATTGGCA AGTAAAGTAG ACATGGTTTG GATAGTCGGA GGCAGTTCTG
5341 TTTACCAGGA AGCCATGAAT CAACCAGGCC ACCTTAGACT CTTTGTGACA AGGATCATGC
5401 AGGAATTTGA AAGTGACACG TTTTTCCCAG AAATTGATTT GGGGAAATAT AAACTTCTCC
5461 CAGAATACCC AGGCGTCCTC TCTGAGGTCC AGGAGGAAAA AGGCATCAAG TATAAGTTTG
5521 AAGTCTACGA GAAGAAAGAC TAACAGGAAG ATGCTTTCAA GTTCTCTGCT CCCCTCCTAA
5581 AGCTATGCAT TTTTATAAGA CCATGGGACT TTTGCTGGCT TTAGATCTCT TTGTGAAGGA
5641 ACCTTACTTC TGTGGTGTGA CATAATTGGA CAAACTACCT ACAGAGATTT AAAGCTCTAA
5701 GGTAAATATA AAATTTTTAA GTGTATAATG TGTTAAACTA CTGATTCTAA TTGTTTGTGT
5761 ATTTTAGATT CCAACCTATG GAACTGATGA ATGGGAGCAG TGGTGGAATG CCTTTAATGA
5821 GGAAAACCTG TTTTGCTCAG AAGAAATGCC ATCTAGTGAT GATGAGGCTA CTGCTGACTC
5881 TCAACATTCT ACTCCTCCAA AAAAGAAGAG AAAGGTAGAA GACCCCAAGG ACTTTCCTTC
5941 AGAATTGCTA AGTTTTTGA GTCATGCTGT GTTTAGTAAT AGAACTCTTG CTTGCTTTGC
6001 TATTTACACC ACAAAGGAAA AAGCTGCACT GCTATACAAG AAAATTATGG AAAAATATTC
6061 TGTAACCTTT ATAAGTAGGC ATAACAGTTA TAATCATAAC ATACTGTTTT TCTTACTCC
```

FIG. 14B

```
6121 ACACAGGCAT AGAGTGTCTG CTATTAATAA CTATGCTCAA AAATTGTGTA CCTTTAGCTT
6181 TTTAATTTGT AAAGGGGTTA ATAAGGAATA TTTGATGTAT AGTGCCTTGA CTAGAGATCA
6241 TAATCAGCCA TACCACATTT GTAGAGGTTT TACTTGCTTT AAAAAACCTC CCACACCTCC
6301 CCCTGAACCT GAAACATAAA ATGAATGCAA TTGTTGTTGT TAACTTGTTT ATTGCAGCTT
6361 ATAATGGTTA CAAATAAAGC AATAGCATCA CAAATTTCAC AAATAAAGCA TTTTTTTCAC
6421 TGCATTCTAG TTGTGGTTTG TCCAAACTCA TCAATGTATC TTATCATGTC TGGATCGGCT
6481 GGATGATCCT CCAGCGCGGG GATCTCATGC TGGAGTTCTT CGCCCACCCC AACTTGTTTA
6541 TTGCAGCTTA TAATGGTTAC AAATAAAGCA ATAGCATCAC AAATTTCACA AATAAAGCAT
6601 TTTTTTCACT GCATTCTAGT TGTGGTTTGT CCAAACTCAT CAATGTATCT TATCATGTCT
6661 GTATACCGTC GACCTCTAGC TAGAGCTTGG CGTAATCATG GTCATAGCTG TTTCCTGTGT
6721 GAAATTGTTA TCCGCTCACA ATTCCACACA ACATACGAGC CGGAAGCATA AAGTGTAAAG
6781 CCTGGGGTGC CTAATGAGTG AGCTAACTCA CATTAATTGC GTTGCGCTCA CTGCCCGCTT
6841 TCCAGTCGGG AAACCTGTCG TGCCAGCTGC ATTAATGAAT CGGCCAACGC GCGGGGAGAG
6901 GCGGTTTGCG TATTGGGCGC TCTTCCGCTT CCTCGCTCAC TGACTCGCTG CGCTCGGTCG
6961 TTCGGCTGCG GCGAGCGGTA TCAGCTCACT CAAAGGCGGT AATACGGTTA TCCACAGAAT
7021 CAGGGGATAA CGCAGGAAAG AACATGTGAG CAAAAGGCCA GCAAAAGGCC AGGAACCGTA
7081 AAAAGGCCGC GTTGCTGGCG TTTTTCCATA GGCTCCGCCC CCTGACGAG CATCACAAAA
7141 ATCGACGCTC AAGTCAGAGG TGGCGAAACC CGACAGGACT ATAAAGATAC CAGGCGTTTC
7201 CCCCTGGAAG CTCCCTCGTG CGCTCTCCTG TTCCGACCCT GCCGCTTACC GGATACCTGT
7261 CCGCCTTTCT CCCTTCGGGA AGCGTGGCGC TTTCTCAATG CTCACGCTGT AGGTATCTCA
7321 GTTCGGTGTA GGTCGTTCGC TCCAAGCTGG GCTGTGTGCA CGAACCCCC GTTCAGCCCG
7381 ACCGCTGCGC CTTATCCGGT AACTATCGTC TTGAGTCCAA CCCGGTAAGA CACGACTTAT
7441 CGCCACTGGC AGCAGCCACT GGTAACAGGA TTAGCAGAGC GAGGTATGTA GGCGGTGCTA
7501 CAGAGTTCTT GAAGTGGTGG CCTAACTACG GCTACACTAG AAGGACAGTA TTTGGTATCT
7561 GCGCTCTGCT GAAGCCAGTT ACCTTCGGAA AAAGAGTTGG TAGCTCTTGA TCCGGCAAAC
7621 AAACCACCGC TGGTAGCGGT GGTTTTTTTG TTTGCAAGCA GCAGATTACG CGCAGAAAAA
7681 AAGGATCTCA AGAAGATCCT TTGATCTTTT CTACGGGGTC TGACGCTCAG TGGAACGAAA
7741 ACTCACGTTA AGGGATTTTG GTCATGAGAT TATCAAAAAG GATCTTCACC TAGATCCTTT
7801 TAAATTAAAA ATGAAGTTTT AAATCAATCT AAAGTATATA TGAGTAAACT TGGTCTGACA
7861 GTTACCAATG CTTAATCAGT GAGGCACCTA TCTCAGCGAT CTGTCTATTT CGTTCATCCA
7921 TAGTTGCCTG ACTCCCCGTC GTGTAGATAA CTACGATACG GGAGGGCTTA CCATCTGGCC
7981 CCAGTGCTGC AATGATACCG CGAGACCCAC GCTCACCGGC TCCAGATTTA TCAGCAATAA
8041 ACCAGCCAGC CGGAAGGGCC GAGCGCAGAA GTGGTCCTGC AACTTTATCC GCCTCCATCC
8101 AGTCTATTAA TTGTTGCCGG GAAGCTAGAG TAAGTAGTTC GCCAGTTAAT AGTTTGCGCA
8161 ACGTTGTTGC CATTGCTACA GGCATCGTGG TGTCACGCTC GTCGTTTGGT ATGGCTTCAT
8221 TCAGCTCCGG TTCCCAACGA TCAAGGCGAG TTACATGATC CCCCATGTTG TGCAAAAAAG
8281 CGGTTAGCTC CTTCGGTCCT CCGATCGTTG TCAGAAGTAA GTTGGCCGCA GTGTTATCAC
8341 TCATGGTTAT GGCAGCACTG CATAATTCTC TTACTGTCAT GCCATCCGTA AGATGCTTTT
8401 CTGTGACTGG TGAGTACTCA ACCAAGTCAT TCTGAGAATA GTGTATGCGG CGACCGAGTT
8461 GCTCTTGCCC GGCGTCAATA CGGGATAATA CCGCGCCACA TAGCAGAACT TTAAAAGTGC
8521 TCATCATTGG AAAACGTTCT TCGGGGCGAA AACTCTCAAG GATCTTACCG CTGTTGAGAT
8581 CCAGTTCGAT GTAACCCACT CGTGCACCCA ACTGATCTTC AGCATCTTTT ACTTTCACCA
8641 GCGTTTCTGG GTGAGCAAAA ACAGGAAGGC AAAATGCCGC AAAAAAGGGA ATAAGGGCGA
8701 CACGGAAATG TTGAATACTC ATACTCTTCC TTTTTCAATA TTATTGAAGC ATTTATCAGG
8761 GTTATTGTCT CATGAGCGGA TACATATTTG AATGTATTTA GAAAAATAAA CAAATAGGGG
8821 TTCCGCGCAC ATTTCCCCGA AAAGTGCCAC CTGACGTC
```

FIG. 14C

Vκ Domain

```
              1                  10                   20                    30                   40
CD40          D I V L T Q S P A T L S V T P G D R V S L S C R A S Q S I S D Y L H W Y Q Q K S H E S P R L L I K
                                                              — | —                         — | —
VKIII         E I V L T Q S P A T L S L S P G E R A T L S C R A S Q S V S S Y L A W Y Q Q K P G Q A P R L L I Y
                                                                                                            *

50                 60                   70                   80                    90                100
CD40          Y A S H S I S G I P S R F S G S G S G S D F T L S I N S V E P E D V G I Y Y C Q H G H S F P W T F G G G T K L E I K
                      — | —                                                          — | —
VKIII/JK4     D A S N R A T G I P A R F S G S G S G T D F T L T I S S L E P E D F A V Y Y C Q Q R S N W P L T F G G G T K V E I K
                                                                                                                              *
```

VH Domain

```
              1                  10                    20                    30                     40
CD40          Q I Q L V Q S G P E L K K P G E T V R I S C K A S G Y A F T T T G M Q W V Q E M P G K G L K W I G
                — | —                                                  — | —                              — | —
VH7           Q V Q L V Q S G S E L K K P G A S V K V S C K A S G Y T F T S Y A M N W V R Q A P G Q G L E W M G
                                                                         *  *                                *

50                  60                    70                     80    abc          90
CD40          W I N T H S G V P K Y V E D F K G R F A F S L E T S A N T A Y L Q I S N L K N E D T A T Y F C V R
                      — | —                      — | —                                      — | —
VH7           W I N T N T G N P T Y A Q G F T G R F V F S L D T S V S T A Y L Q I S S L K A E D T A V Y Y C A R
                                                                                                            * abcde            110
CD40          S G N G N Y D L A Y F A Y W G Q G T L V T V S A
                                                          — | —
JH4                       Y F D Y W G Q G T L V T V S S
```

FIG. 15

Murine Framework Residues

Murine Framework Residues

SEQUENCE LISTING

<160> NUMBER OF SEQ ID NOS: 14

<210> SEQ ID NO 1
<211> LENGTH: 108
<212> TYPE: PRT
<213> ORGANISM: Human and Mouse

<400> SEQUENCE: 1

Asp Ile Val Leu Thr Gln Ser Pro Ala Thr Leu Ser Val Thr Pro Gly
 1               5                  10                  15

```
Asp Arg Val Ser Leu Ser Cys Arg Ala Ser Gln Ser Ile Ser Asp Tyr
             20                  25                  30

Leu His Trp Tyr Gln Gln Lys Ser His Glu Ser Pro Arg Leu Leu Ile
         35                  40                  45

Lys Tyr Ala Ser His Ser Ile Ser Gly Ile Pro Ser Arg Phe Ser Gly
     50                  55                  60

Ser Gly Ser Gly Ser Asp Phe Thr Leu Ser Ile Asn Ser Val Glu Pro
 65                  70                  75                  80

Glu Asp Val Gly Ile Tyr Tyr Cys Gln His Gly His Ser Phe Pro Trp
                 85                  90                  95

Thr Phe Gly Gly Gly Thr Lys Leu Glu Ile Lys Arg
                100                 105

<210> SEQ ID NO 2
<211> LENGTH: 122
<212> TYPE: PRT
<213> ORGANISM: Human and Mouse

<400> SEQUENCE: 2

Gln Ile Gln Leu Val Gln Ser Gly Pro Glu Leu Lys Lys Pro Gly Glu
 1               5                  10                  15

Thr Val Arg Ile Ser Cys Lys Ala Ser Gly Tyr Ala Phe Thr Thr Thr
             20                  25                  30

Gly Met Gln Trp Val Gln Glu Met Pro Gly Lys Gly Leu Lys Trp Ile
         35                  40                  45

Gly Trp Ile Asn Thr His Ser Gly Val Pro Lys Tyr Val Glu Asp Phe
     50                  55                  60

Lys Gly Arg Phe Ala Phe Ser Leu Glu Thr Ser Ala Asn Thr Ala Tyr
 65                  70                  75                  80

Leu Gln Ile Ser Asn Leu Lys Asn Glu Asp Thr Ala Thr Tyr Phe Cys
                 85                  90                  95

Val Arg Ser Gly Asn Gly Asn Tyr Asp Leu Ala Tyr Phe Ala Tyr Trp
                100                 105                 110

Gly Gln Gly Thr Leu Val Thr Val Ser Ala
            115                 120

<210> SEQ ID NO 3
<211> LENGTH: 451
<212> TYPE: PRT
<213> ORGANISM: Human and Mouse

<400> SEQUENCE: 3

Gln Ile Gln Leu Val Gln Ser Gly Pro Glu Leu Lys Lys Pro Gly Glu
 1               5                  10                  15

Thr Val Arg Ile Ser Cys Lys Ala Ser Gly Tyr Ala Phe Thr Thr Thr
             20                  25                  30

Gly Met Gln Trp Val Gln Glu Met Pro Gly Lys Gly Leu Lys Trp Ile
         35                  40                  45

Gly Trp Ile Asn Thr His Ser Gly Val Pro Lys Tyr Val Glu Asp Phe
     50                  55                  60

Lys Gly Arg Phe Ala Phe Ser Leu Glu Thr Ser Ala Asn Thr Ala Tyr
 65                  70                  75                  80

Leu Gln Ile Ser Asn Leu Lys Asn Glu Asp Thr Ala Thr Tyr Phe Cys
                 85                  90                  95

Val Arg Ser Gly Asn Gly Asn Tyr Asp Leu Ala Tyr Phe Ala Tyr Trp
                100                 105                 110
```

```
Gly Gln Gly Thr Leu Val Thr Val Ser Ala Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 4
<211> LENGTH: 214
<212> TYPE: PRT
<213> ORGANISM: Human and Mouse

<400> SEQUENCE: 4

Asp Ile Val Leu Thr Gln Ser Pro Ala Thr Leu Ser Val Thr Pro Gly
  1               5                  10                  15

Asp Arg Val Ser Leu Ser Cys Arg Ala Ser Gln Ser Ile Ser Asp Tyr
                20                  25                  30
```

```
Leu His Trp Tyr Gln Gln Lys Ser His Glu Ser Pro Arg Leu Leu Ile
         35                  40                  45
Lys Tyr Ala Ser His Ser Ile Ser Gly Ile Pro Ser Arg Phe Ser Gly
 50                  55                  60
Ser Gly Ser Gly Ser Asp Phe Thr Leu Ser Ile Asn Ser Val Glu Pro
 65                  70                  75                  80
Glu Asp Val Gly Ile Tyr Tyr Cys Gln His Gly His Ser Phe Pro Trp
                 85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 5
<211> LENGTH: 8614
<212> TYPE: DNA
<213> ORGANISM: Human and Mouse

<400> SEQUENCE: 5
gacggatcgg gagatctgct aggtgacctg aggcgcgccg gcttcgaata gccagagtaa      60
cctttttttt taattttatt ttattttatt tttgagatgg agtttggcgc cgatctcccg     120
atcccctatg gtcgactctc agtacaatct gctctgatgc cgcatagtta agccagtatc     180
tgctccctgc ttgtgtgttg gaggtcgctg agtagtgcgc gagcaaaatt taagctacaa     240
caaggcaagg cttgaccgac aattgcatga agaatctgct tagggttagg cgttttgcgc     300
tgcttcgcga tgtacgggcc agatatacgc gttgacattg attattgact agttattaat     360
agtaatcaat tacggggtca ttagttcata gcccatatat ggagttccgc gttacataac     420
ttacggtaaa tggcccgcct ggctgaccgc ccaacgaccc ccgcccattg acgtcaataa     480
tgacgtatgt tcccatagta acgccaatag ggactttcca ttgacgtcaa tgggtggact     540
atttacggta aactgcccac ttggcagtac atcaagtgta tcatatgcca agtacgcccc     600
ctattgacgt caatgacggt aaatggcccg cctggcatta tgcccagtac atgaccttat     660
gggactttcc tacttggcag tacatctacg tattagtcat cgctattacc atggtgatgc     720
ggttttggca gtacatcaat gggcgtggat agcggtttga ctcacgggga tttccaagtc     780
tccaccccat tgacgtcaat gggagtttgt tttggcacca aaatcaacgg gactttccaa     840
aatgtcgtaa caactccgcc ccattgacgc aaatgggcgg taggcgtgta cggtgggagg     900
tctatataag cagagctctc tggctaacta gagaacccac tgcttactgg cttatcgaaa     960
ttaatacgac tcactatagg gagacccaag cttggtacca tggactggac ctggagaatc    1020
```

-continued

```
ctcttcttgg tggcagcagc aacaggtgcc cactcccaga tccagttggt gcaatctgga  1080
cctgagctga agaagcctgg agagacagtc aggatctcct gcaaggcttc tgggtatgcc  1140
ttcacaacta ctggaatgca gtgggtgcaa gagatgccag aaagggtttt gaagtggatt  1200
ggctggataa acacccactc tggagtgcca aaatatgtag aagacttcaa gggacggttt  1260
gccttctctt tggaaacctc tgccaacact gcatatttac agataagcaa cctcaaaaat  1320
gaggacacgg ctacgtattt ctgtgtgaga tccgggaatg gtaactatga cctggcctac  1380
tttgcttact ggggccaagg gacactggtc actgtctctg cagctagcac caagggccca  1440
tcggtcttcc ccctggcacc ctcctccaag agcacctctg ggggcacagc ggccctgggc  1500
tgcctggtca aggactactt ccccgaaccg gtgacggtgt cgtggaactc aggcgccctg  1560
accagcggcg tgcacacctt cccggctgtc ctacagtcct caggactcta ctccctcagc  1620
agcgtggtga ccgtgccctc cagcagcttg ggcacccaga cctacatctg caacgtgaat  1680
cacaagccca gcaacaccaa ggtggacaag aaagttggtg agaggccagc acagggaggg  1740
agggtgtctg ctggaagcca ggctcagcgc tcctgcctgg acgcatcccg ctatgcagc  1800
cccagtccag ggcagcaagg caggccccgt ctgcctcttc acccggaggc ctctgcccgc  1860
cccactcatg ctcagggaga gggtcttctg cttttttccc caggctctgg gcaggcacag  1920
gctaggtgcc cctaacccag gccctgcaca caaaggggca ggtgctgggc tcagacctgc  1980
caagagccat atccgggagg accctgcccc tgacctaagc ccaccccaaa ggccaaactc  2040
tccactccct cagtcggac accttctctc ctcccagatt ccagtaactc ccaatcttct  2100
ctctgcagag cccaaatctt gtgacaaaac tcacacatgc ccaccgtgcc caggtaagcc  2160
agcccaggcc tcgccctcca gctcaaggcg ggacaggtgc cctagagtag cctgcatcca  2220
gggacaggcc ccagccgggt gctgacacgt ccacctccat ctcttcctca gcacctgaac  2280
tcctggggg accgtcagtc ttcctcttcc ccccaaaacc caaggacacc ctcatgatct  2340
cccggacccc tgaggtcaca tgcgtggtgg tggacgtgag ccacgaagac cctgaggtca  2400
agttcaactg gtacgtggac ggcgtggagg tgcataatgc caagacaaag ccgcgggagg  2460
agcagtacaa cagcacgtac cgtgtggtca gcgtcctcac cgtcctgcac caggactggc  2520
tgaatggcaa ggagtacaag tgcaaggtct ccaacaaagc cctcccagcc ccatcgaga  2580
aaaccatctc caaagccaaa ggtgggaccc gtggggtgcg agggccacat ggacagaggc  2640
cggctcggcc caccctctgc cctgagagtg accgctgtac caacctctgt ccctacaggg  2700
cagccccgag aaccacaggt gtacaccctg cccccatccc gggatgagct gaccaagaac  2760
caggtcagcc tgacctgcct ggtcaaaggc ttctatccca gcgacatcgc cgtggagtgg  2820
gagagcaatg ggcagccgga gaacaactac aagaccacgc ctcccgtgct ggactccgac  2880
ggctccttct tcctctacag caagctcacc gtggacaaga gcaggtggca gcaggggaac  2940
gtcttctcat gctccgtgat gcatgaggct ctgcacaacc actacacgca gaagagcctc  3000
tccctgtctc cgggtaaatg agtgcgacgg ccggcaagcc cccgctcccc gggctctcgc  3060
ggtcgcacga ggatgcttgg cacgtacccc ctgtacatac ttcccgggcg cccagcatgg  3120
aaataaagca cccagcgctg ccctgggccc ctgcgagact gtgatggttc tttccacggg  3180
tcaggccgag tctgaggcct gagtggcatg agggaggcag agcgggtccc actgtcccca  3240
cactggccca ggctgtgcag gtgtgcctgg gccccctagg gtgggctca gccaggggct  3300
gccctcggca gggtggggga tttgccagcg tggccctccc tccagcagca cctgccctgg  3360
gctgggccac gggaagccct aggagcccct ggggacagac acacagcccc tgcctctgta  3420
```

```
ggagactgtc ctgttctgtg agcgccctg tcctcccgac ctccatgccc actcggggc     3480
atgcctagtc catgtgcgta gggacaggcc ctccctcacc catctacccc cacggcacta   3540
accccctggct gccctgccca gcctcgcacc cgcatgggga cacaaccgac tccggggaca  3600
tgcactctcg ggccctgtgg agggactggt gcagatgccc acacacacac tcagcccaga  3660
cccgttcaac aaaccccgca ctgaggttgg ccggccacac ggccaccaca cacacacgtg   3720
cacgcctcac acacggagcc tcacccgggc gaactgcaca gcacccagac cagagcaagg  3780
tcctcgcaca cgtgaacact cctcggacac aggcccccac gagccccacg cggcacctca   3840
aggcccacga gcctctcggc agcttctcca catgctgacc tgctcagaca aacccagccc   3900
tcctctcaca agggtgcccc tgcagccgcc acacacacac aggggatcac acaccacgtc   3960
acgtccctgg ccctggccca cttcccagtg ccgcccttcc ctgcaggacg atcagcctc   4020
gactgtgcct tctagttgcc agccatctgt tgttgccccc tcccccgtgc cttccttgac   4080
cctggaaggt gccactccca ctgtcctttc ctaataaaat gaggaaattg catcgcattg   4140
tctgagtagg tgtcattcta ttctgggggg tggggtgggg caggacagca agggggagga  4200
ttgggaagac aatagcaggc atgctgggga tgcggtgggc tctatggctt ctgaggcgga  4260
aagaaccagc tggggctcta gggggtatcc ccacgcgccc tgtagcggcg cattaagcgc   4320
ggcgggtgtg gtggttacgc gcagcgtgac cgctacactt gccagcgccc tagcgcccgc  4380
tcctttcgct ttcttccctt cctttctcgc cacgttcgcc gggcctctca aaaagggaa   4440
aaaaagcatg catctcaatt agtcagcaac catagtcccg cccctaactc cgcccatccc   4500
gcccctaact ccgcccagtt ccgcccattc tccgccccat ggctgactaa ttttttttat   4560
ttatgcagag gccgaggccg cctcggcctc tgagctattc cagaagtagt gaggaggctt   4620
ttttggaggc ctaggctttt gcaaaaagct tggacagctc agggctgcga tttcgcgcca   4680
aacttgacgg caatcctagc gtgaaggctg gtaggatttt atccccgctg ccatcatggt   4740
tcgaccattg aactgcatcg tcgccgtgtc ccaaaatatg gggattggca agaacggaga   4800
cctaccctgg cctccgctca ggaacgagtt caagtacttc caaagaatga ccacaacctc   4860
ttcagtggaa ggtaaacaga atctggtgat tatgggtagg aaaacctggt tctccattcc   4920
tgagaagaat cgacctttaa aggacagaat taatatagtt ctcagtagag aactcaaaga   4980
accaccacga ggagctcatt ttcttgccaa aagtttggat gatgccttaa gacttattga   5040
acaaccggaa ttgcaagta aagtagacat ggtttggata gtcggaggca gttctgttta   5100
ccaggaagcc atgaatcaac caggccacct tagactcttt gtgacaagga tcatgcagga   5160
atttgaaagt gacacgtttt tcccagaaat tgatttgggg aaatataaac ttctcccaga   5220
atacccaggc gtcctctctg aggtccagga ggaaaaaggc atcaagtata agtttgaagt   5280
ctacgagaag aaagactaac aggaagatgc tttcaagttc tctgctcccc tcctaaagct   5340
atgcatttttt ataagaccat gggacttttg ctggctttag atctctttgt gaaggaacct   5400
tacttctgtg gtgtgacata attggacaaa ctacctacag agatttaaag ctctaaggta   5460
aatataaaat tttttaagtgt ataatgtgtt aaactactga ttctaattgt ttgtgtattt   5520
tagattccaa cctatggaac tgatgaatgg gagcagtggt ggaatgcctt taatgaggaa   5580
aacctgtttt gctcagaaga aatgccatct agtgatgatg aggctactgc tgactctcaa   5640
cattctactc ctccaaaaaa gaagagaaag gtagaagacc ccaaggactt ccttcagaa    5700
ttgctaagtt ttttgagtca tgctgtgttt agtaatagaa ctcttgcttg ctttgctatt   5760
```

```
tacaccacaa aggaaaaagc tgcactgcta tacaagaaaa ttatggaaaa atattctgta    5820
acctttataa gtaggcataa cagttataat cataacatac tgttttttct tactccacac    5880
aggcatagag tgtctgctat taataactat gctcaaaaat tgtgtacctt tagcttttta    5940
atttgtaaag gggttaataa ggaatatttg atgtatagtg ccttgactag agatcataat    6000
cagccatacc acatttgtag aggttttact tgctttaaaa aacctcccac acctccccct    6060
gaacctgaaa cataaaatga atgcaattgt tgttgttaac ttgtttattg cagcttataa    6120
tggttacaaa taaagcaata gcatcacaaa tttcacaaat aaagcatttt ttcactgca     6180 ttctagttgt ggtttgtcca aactcatcaa tgtatcttat catgtctgga tcggctggat    6240
gatcctccag cgcggggatc tcatgctgga gttcttcgcc cacccaact tgtttattgc     6300 agcttataat ggttacaaat aaagcaatag catcacaaat ttcacaaata aagcattttt    6360
ttcactgcat tctagttgtg gtttgtccaa actcatcaat gtatcttatc atgtctgtat    6420
accgtcgacc tctagctaga gcttggcgta atcatggtca tagctgtttc ctgtgtgaaa    6480
ttgttatccg ctcacaattc cacacaacat acgagccgga agcataaagt gtaaagcctg    6540
gggtgcctaa tgagtgagct aactcacatt aattgcgttg cgctcactgc ccgctttcca    6600
gtcgggaaac ctgtcgtgcc agctgcatta atgaatcggc caacgcgcgg ggagaggcgg    6660
tttgcgtatt gggcgctctt ccgcttcctc gctcactgac tcgctgcgct cggtcgttcg    6720
gctgcggcga gcggtatcag ctcactcaaa ggcggtaata cggttatcca cagaatcagg    6780
ggataacgca ggaaagaaca tgtgagcaaa aggccagcaa aaggccagga accgtaaaaa    6840
ggccgcgttg ctggcgtttt tccataggct ccgcccccct gacgagcatc acaaaaatcg    6900
acgctcaagt cagaggtggc gaaacccgac aggactataa agataccagg cgtttccccc    6960
tggaagctcc ctcgtgcgct ctcctgttcc gaccctgccg cttaccggat acctgtccgc    7020
ctttctccct tcgggaagcg tggcgctttc tcaatgctca cgctgtaggt atctcagttc    7080
ggtgtaggtc gttcgctcca agctgggctg tgtgcacgaa ccccccgttc agcccgaccg    7140
ctgcgcctta tccggtaact atcgtcttga gtccaacccg gtaagacacg acttatcgcc    7200
actggcagca gccactggta acaggattag cagagcgagg tatgtaggcg gtgctacaga    7260
gttcttgaag tggtggccta actacggcta cactagaagg acagtatttg gtatctgcgc    7320
tctgctgaag ccagttacct tcggaaaaag agttggtagc tcttgatccg gcaaacaaac    7380
caccgctggt agcggtggtt tttttgtttg caagcagcag attacgcgca gaaaaaaagg    7440
atctcaagaa gatcctttga tcttttctac ggggtctgac gctcagtgga acgaaaactc    7500
acgttaaggg attttggtca tgagattatc aaaaaggatc ttcacctaga tccttttaaa    7560
ttaaaaatga agttttaaat caatctaaag tatatatgag taaacttggt ctgacagtta    7620
ccaatgctta atcagtgagg cacctatctc agcgatctgt ctatttcgtt catccatagt    7680
tgcctgactc cccgtcgtgt agataactac gatacgggag ggcttaccat ctggccccag    7740
tgctgcaatg ataccgcgag acccacgctc accggctcca gatttatcag caataaacca    7800
gccagccgga agggccgagc gcagaagtgg tcctgcaact ttatccgcct ccatccagtc    7860
tattaattgt tgccgggaag ctagagtaag tagttcgcca gttaatagtt tgcgcaacgt    7920
tgttgccatt gctacaggca tcgtggtgtc acgctcgtcg tttggtatgg cttcattcag    7980
ctccggttcc caacgatcaa ggcgagttac atgatccccc atgttgtgca aaaaagcggt    8040
tagctccttc ggtcctccga tcgttgtcag aagtaagttg gccgcagtgt tatcactcat    8100
ggttatggca gcactgcata attctcttac tgtcatgcca tccgtaagat gcttttctgt    8160
```

```
gactggtgag tactcaacca agtcattctg agaatagtgt atgcggcgac cgagttgctc    8220
ttgcccggcg tcaatacggg ataataccgc gccacatagc agaactttaa aagtgctcat    8280
cattggaaaa cgttcttcgg ggcgaaaact ctcaaggatc ttaccgctgt tgagatccag    8340
ttcgatgtaa cccactcgtg cacccaactg atcttcagca tcttttactt tcaccagcgt    8400
ttctgggtga gcaaaaacag gaaggcaaaa tgccgcaaaa aagggaataa gggcgacacg    8460
gaaatgttga atactcatac tcttcctttt tcaatattat tgaagcattt atcagggtta    8520
ttgtctcatg agcggataca tatttgaatg tatttagaaa aataaacaaa tagggggttcc    8580 gcgcacattt ccccgaaaag tgccacctga cgtc                                8614

<210> SEQ ID NO 6
<211> LENGTH: 8858
<212> TYPE: DNA
<213> ORGANISM: Human and Mouse

<400> SEQUENCE: 6
gacggatcgg gagatctgct agcccggggtg acctgaggcg cgccggcttc gaatagccag      60
agtaaccttt ttttttaatt ttattttatt ttatttttga gatggagttt ggcgccgatc     120
tcccgatccc ctatggtcga ctctcagtac aatctgctct gatgccgcat agttaagcca     180
gtatctgctc cctgcttgtg tgttggaggt cgctgagtag tgcgcgagca aaatttaagc     240
tacaacaagg caaggcttga ccgacaattg catgaagaat ctgcttaggg ttaggcgttt     300
tgcgctgctt cgcgatgtac gggccagata tacgcgttga cattgattat tgactagtta     360
ttaatagtaa tcaattacgg ggtcattagt tcatagccca tatatggagt tccgcgttac     420
ataacttacg gtaaatggcc cgcctggctg accgcccaac gaccccccgcc cattgacgtc     480 aataatgacg tatgttccca tagtaacgcc aatagggact ttccattgac gtcaatgggt     540
ggactattta cggtaaactg cccacttggc agtacatcaa gtgtatcata tgccaagtac     600
gccccctatt gacgtcaatg acggtaaatg gcccgcctgg cattatgccc agtacatgac     660
cttatgggac tttcctactt ggcagtacat ctacgtatta gtcatcgcta ttaccatggt     720
gatgcggttt tggcagtaca tcaatgggcg tggatagcgg tttgactcac ggggatttcc     780
aagtctccac cccattgacg tcaatgggag tttgttttgg caccaaaatc aacgggactt     840
tccaaaatgt cgtaacaact ccgccccatt gacgcaaatg ggcggtaggc gtgtacggtg     900
ggaggtctat ataagcagag ctctctggct aactagagaa cccactgctt actggcttat     960
cgaaattaat acgactcact atagggagac ccaagcttgg taccatggaa gccccagctc    1020
agcttctctt cctcctgcta tctctggctcc cagataccac cggagacatt gttctgactc    1080
agtctccagc caccctgtct gtgactccag gagatagagt ctctctttcc tgcagggcca    1140
gccagagtat tagcgactac ttacactggt atcaacaaaa atcacatgag tctccaaggc    1200
ttctcatcaa atatgcttcc cattccatct ctgggatccc ctccaggttc agtggcagtg    1260
gatcagggtc agatttcact ctcagtatca acagtgtgga acctgaagat gttggaattt    1320
attactgtca acatggtcac agctttccgt ggacgttcgg tggaggcacc aagctggaaa    1380
tcaaacgtaa gtctcgagtc tctagataac cggtcaatcg gtcaatcgat tggaattcta    1440
aactctgagg gggtcggatg acgtggccat tctttgccta aagcattgag tttactgcaa    1500
ggtcagaaaa gcatgcaaag ccctcagaat ggctgcaaag agctccaaca aaacaattta    1560
gaactttatt aaggaatagg gggaagctag gaagaaactc aaaacatcaa gattttaaat    1620
```

| | |
|---|---|
| acgcttcttg gtctccttgc tataattatc tgggataagc atgctgtttt ctgtctgtcc | 1680 |
| ctaacatgcc cttatccgca acaacacac ccaagggcag aactttgtta cttaaacacc | 1740 |
| atcctgtttg cttctttcct caggaactgt ggctgcacca tctgtcttca tcttcccgcc | 1800 |
| atctgatgag cagttgaaat ctggaactgc ctctgttgtg tgcctgctga ataacttcta | 1860 |
| tcccagagag gccaaagtac agtggaaggt ggataacgcc ctccaatcgg gtaactccca | 1920 |
| ggagagtgtc acagagcagg acagcaagga cagcacctac agcctcagca gcaccctgac | 1980 |
| gctgagcaaa gcagactacg agaaacacaa agtctacgcc tgcgaagtca cccatcaggg | 2040 |
| cctgagctcg cccgtcacaa agagcttcaa caggggagag tgttagaggg agaagtgccc | 2100 |
| ccacctgctc ctcagttcca gcctgacccc ctcccatcct ttggcctctg accctttttc | 2160 |
| cacaggggac ctacccctat tgcggtcctc cagctcatct ttcacctcac cccctcctc | 2220 |
| ctccttggct ttaattatgc taatgttgga ggagaatgaa taaataaagt gaatctttgc | 2280 |
| acctgtggtt tctctctttc ctcatttaat aattattatc tgttgtttta ccaactactc | 2340 |
| aatttctctt ataagggact aaatatgtag tcatcctaag gcacgtaacc atttataaaa | 2400 |
| atcatccttc attctatttt accctatcat cctctgcaag acagtcctcc ctcaaaccca | 2460 |
| caagccttct gtcctcacag tcccctgggc catggtagga gagacttgct tccttgttt | 2520 |
| cccctcctca gcaagccctc atagtccttt ttaagggtga caggtcttac agtcatatat | 2580 |
| cctttgattc aattccctga gaatcaacca aagcaaattt ttcaaaagaa gaaacctgct | 2640 |
| ataaagagaa tcattcattg caacatgata taaaataaca acacaataaa agcaattaaa | 2700 |
| taaacaaaca atagggaaat gtttaagttc atcatggtac ttagacttaa tggaatgtca | 2760 |
| tgccttattt acatttttaa acaggtactg agggactcct gtctgccaag ggccgtattg | 2820 |
| agtactttcc acaacctaat ttaatccaca ctatactgtg agattaaaaa cattcattaa | 2880 |
| aatgttgcaa aggttctata aagctgagag acaaatatat tctataactc agcaatccca | 2940 |
| cttctagatg actgagtgtc cccacccacc aaaaaactat gcaagaatgt tcaaagcagc | 3000 |
| tttatttaca aaagccaaaa attggaaata gcccgattgt ccaacaatag aatgagttat | 3060 |
| taaactgtgg tatgttttata cattagaata cccaatgagg agaattaaca agctacaact | 3120 |
| ataacctactc acacagatga atctcataaa aataatgtta cataagagaa actcaatgca | 3180 |
| aaagatatgt tctgtatgtt ttcatccata taaagttcaa aaccaggtaa aaataaagtt | 3240 |
| agaaatttga tggaaattta ctcttagctg ggggtgggcg agttagtgcc tgggagaaga | 3300 |
| caagaagggg cttctggggt cttggtaatg ttctgttcct cgtgtggggt tgtgcagtta | 3360 |
| tgatctgtgc actgttctgt atacacatta tgcttcaaaa taacttcaca taagaacat | 3420 |
| cttatcccca gttaatagat agaagaggaa taagtaatag gtcaagacca acgcagctgg | 3480 |
| taagtggggg cctgggatca aatagctacc tgcctaatcc tgcccwcttg agccctgaat | 3540 |
| gagtctgcct tccagggctc aaggtgctca acaaaacaac aggcctgcta ttttcctggc | 3600 |
| atctgtgccc tgtttggcta gctaggagca cacatacata gaaattaaat gaaacagacc | 3660 |
| ttcagcaagg ggacagagga cagaattaac cttgcccaga cactggaaac ccatgtatga | 3720 |
| acactcacat gtttgggaag ggggaagggc acatgtaaat gaggactctt cctcattcta | 3780 |
| tggggcactc tggccctgcc cctctcagct actcatccat ccaacacacc tttctaagta | 3840 |
| cctctctctg cctacactct gaaggggttc aggagtaact aacacagcat cccttccctc | 3900 |
| aaatgactga caatcccttt gtcctgcttt gttttctttt ccagtcagta ctgggaaagt | 3960 |
| ggggaaggac agtcatggag aaactacata aggaagcacc ttgcccttct gcctcttgag | 4020 |

```
aatgttgatg agtatcaaat ctttcaaact ttggaggttt gagtaggggt gagactcagt    4080
aatgtcccctt ccaatgacat gaacttgctc actcatccct gggggccaaa ttgaacaatc   4140
aaaggcaggc ataatccagt tatgaattct tgcggccgct tgctagcttc acgtgttgga    4200
tccaaccgcg gaagggccct attctatagt gtcacctaaa tgctagagct cgctgatcag    4260
cctcgactgt gccttctagt tgccagccat ctgttgtttg cccctcccccc gtgccttcct   4320
tgaccctgga aggtgccact cccactgtcc tttcctaata aaatgaggaa attgcatcgc    4380
attgtctgag taggtgtcat tctattctgg ggggtggggt ggggcaggac agcaaggggg    4440
aggattggga agacaatagc aggcatgctg gggatgcggt gggctctatg gcttctgagg    4500
cggaaagaac cagctggggc tctaggggt atccccacgc gccctgtagc ggcgcattaa     4560
gcgcggcggg tgtggtggtt acgcgcagcg tgaccgctac acttgccagc gccctagcgc    4620
ccgctccttt cgctttcttc ccttcctttc tcgccacgtt cgccgggcct ctcaaaaaag    4680
ggaaaaaaag catgcatctc aattagtcag caaccatagt cccgcccct actccgccca     4740
tcccgcccct aactccgccc agttccgccc attctccgcc ccatggctga ctaattttttt   4800
ttatttatgc agaggccgag gccgcctcgg cctctgagct attccagaag tagtgaggag    4860
gctttttgg aggcctaggc ttttgcaaaa agcttggaca gctcagggct gcgatttcgc     4920
gccaaacttg acggcaatcc tagcgtgaag gctggtagga ttttatcccc gctgccatca    4980
tggttcgacc attgaactgc atcgtcgccg tgtcccaaaa tatggggatt ggcaagaacg    5040
gagacctacc ctggcctccg ctcaggaacg agttcaagta cttccaaaga atgaccacaa    5100
cctcttcagt ggaaggtaaa cagaatctgg tgattatggg taggaaaacc tggttctcca    5160
ttcctgagaa gaatcgacct ttaaaggaca gaattaatat agttctcagt agagaactca    5220
aagaaccacc acgaggagct cattttcttg ccaaaagttt ggatgatgcc ttaagactta    5280
ttgaacaacc ggaattggca agtaaagtag acatggtttg gatagtcgga ggcagttctg    5340
tttaccagga agccatgaat caaccaggcc accttagact cttgtgaca aggatcatgc     5400
aggaatttga aagtgacacg ttttcccag aaattgattt ggggaaatat aaacttctcc      5460
cagaataccc aggcgtcctc tctgaggtcc aggaggaaaa aggcatcaag tataagtttg    5520
aagtctacga gaagaaagac taacaggaag atgctttcaa gttctctgct cccctcctaa    5580
agctatgcat ttttataaga ccatgggact tttgctggct ttagatctct ttgtgaagga    5640
accttacttc tgtggtgtga cataattgga caaactacct acagagattt aaagctctaa    5700
ggtaaatata aaattttttaa gtgtataatg tgttaaacta ctgattctaa ttgtttgtgt    5760
attttagatt ccaacctatg gaactgatga atgggagcag tggtggaatg ccttaatga     5820
ggaaaacctg ttttgctcag aagaaatgcc atctagtgat gatgaggcta ctgctgactc    5880
tcaacattct actcctccaa aaagaagag aaggtagaa gaccccaagg actttccttc      5940
agaattgcta agtttttga gtcatgctgt gtttagtaat agaactcttg cttgctttgc     6000
tatttacacc acaaggaaa aagctgcact gctataccag aaaattatgg aaaaatattc    6060
tgtaaccttt ataagtaggc ataacagtta taatcataac atactgtttt tcttactcc     6120
acacaggcat agagtgtctg ctattaataa ctatgctcaa aaattgtgta cctttagctt   6180
tttaatttgt aaagggtta ataaggaata tttgatgtat agtgccttga ctagagatca    6240
taatcagcca taccacatt gtagaggttt tacttgcttt aaaaaacctc ccacacctcc     6300
ccctgaacct gaaacataaa atgaatgcaa ttgttgttgt taacttgttt attgcagctt    6360
```

-continued

```
ataatggtta caaataaagc aatagcatca caaatttcac aaataaagca ttttttttcac    6420
tgcattctag ttgtggtttg tccaaactca tcaatgtatc ttatcatgtc tggatcggct    6480
ggatgatcct ccagcgcggg gatctcatgc tggagttctt cgcccacccc aacttgttta    6540
ttgcagctta taatggttac aaataaagca atagcatcac aaatttcaca aataaagcat    6600
tttttttcact gcattctagt tgtggtttgt ccaaactcat caatgtatct tatcatgtct    6660
gtataccgtc gacctctagc tagagcttgg cgtaatcatg gtcatagctg tttcctgtgt    6720
gaaattgtta tccgctcaca attccacaca acatacgagc cggaagcata agtgtaaag    6780
cctggggtgc ctaatgagtg agctaactca cattaattgc gttgcgctca ctgcccgctt    6840
tccagtcggg aaacctgtcg tgccagctgc attaatgaat cggccaacgc gcggggagag    6900
gcggtttgcg tattgggcgc tcttccgctt cctcgctcac tgactcgctg cgctcggtcg    6960
ttcggctgcg gcgagcggta tcagctcact caaaggcggt aatacggtta ccacagaat    7020
cagggaataa cgcaggaaag aacatgtgag caaaaggcca gcaaaaggcc aggaaccgta    7080
aaaaggccgc gttgctggcg ttttttccata ggctccgccc ccctgacgag catcacaaaa    7140
atcgacgctc aagtcagagg tggcgaaacc cgacaggact ataaagatac caggcgtttc    7200
cccctggaag ctccctcgtg cgctctcctg ttccgaccct gccgcttacc ggatacctgt    7260
ccgcctttct cccttcggga agcgtggcgc tttctcaatg ctcacgctgt aggtatctca    7320
gttcggtgta ggtcgttcgc tccaagctgg gctgtgtgca cgaaccccccc gttcagcccg    7380
accgctgcgc cttatccggt aactatcgtc ttgagtccaa cccggtaaga cacgacttat    7440
cgccactggc agcagccact ggtaacagga ttagcagagc gaggtatgta ggcggtgcta    7500
cagagttctt gaagtggtgg cctaactacg gctacactag aaggacagta tttggtatct    7560
gcgctctgct gaagccagtt accttcggaa aaagagttgg tagctcttga tccggcaaac    7620
aaaccaccgc tggtagcggt ggtttttttg tttgcaagca gcagattacg cgcagaaaaa    7680
aaggatctca agaagatcct ttgatctttt ctacgggggt ctgacgctcag tggaacgaaa    7740
actcacgtta agggattttg gtcatgagat tatcaaaaag gatcttcacc tagatccttt    7800
taaattaaaa atgaagtttt aaatcaatct aaagtatata tgagtaaact tggtctgaca    7860
gttaccaatg cttaatcagt gaggcaccta tctcagcgat ctgtctattt cgttcatcca    7920
tagttgcctg actccccgtc gtgtagataa ctacgatacg ggagggctta ccatctggcc    7980
ccagtgctgc aatgataccg cgagacccac gctcaccggc tccagattta tcagcaataa    8040
accagccagc cggaagggcc gagcgcagaa gtggtcctgc aactttatcc gcctccatcc    8100
agtctattaa ttgttgccgg gaagctagag taagtagttc gccagttaat agtttgcgca    8160
acgttgttgc cattgctaca ggcatcgtgg tgtcacgctc gtcgtttggt atggcttcat    8220
tcagctccgg ttcccaacga tcaaggcgag ttacatgatc ccccatgttg tgcaaaaaag    8280
cggttagctc cttcggtcct ccgatcgttg tcagaagtaa gttggccgca gtgttatcac    8340
tcatggttat ggcagcactg cataattctc ttactgtcat gccatccgta agatgctttt    8400
ctgtgactgg tgagtactca accaagtcat tctgagaata gtgtatgcgg cgaccgagtt    8460
gctcttgccc ggcgtcaata cgggataata ccgcgccaca tagcagaact ttaaaagtgc    8520
tcatcattgg aaaacgttct cggggcgaaa actctcaag gatcttaccg ctgttgagat    8580
ccagttcgat gtaacccact cgtgcaccca actgatcttc agcatctttt actttcacca    8640
gcgtttctgg gtgagcaaaa acaggaaggc aaaatgccgc aaaaaaggga ataagggcga    8700
cacggaaatg ttgaatactc atactcttcc ttttttcaata ttattgaagc atttatcagg    8760
```

-continued

```
gttattgtct catgagcgga tacatatttg aatgtattta gaaaaataaa caaatagggg      8820
ttccgcgcac atttccccga aaagtgccac ctgacgtc                             8858
```

<210> SEQ ID NO 7
<211> LENGTH: 321
<212> TYPE: DNA
<213> ORGANISM: Human and Mouse

<400> SEQUENCE: 7

```
gaaattgtgt tgacacagtc tccagccacc ctgtctttgt ctccagggga agagccacc       60 ctctcctgca gggccagtca gagtattagc gattacttac attggtacca acagaaacct     120
ggccaggctc ccaggctcct catctattac gcatcccact ccatctctgg catcccagcc     180
aggttcagtg gcagtgggtc tgggacagac ttcactctca ccatcagcag cctagagcct     240
gaagattttg cagtttatta ctgtcagcat ggccactctt tccttggac cttcggaggg      300 gggaccaagg tggaaattaa a                                               321
```

<210> SEQ ID NO 8
<211> LENGTH: 107
<212> TYPE: PRT
<213> ORGANISM: Human and Mouse

<400> SEQUENCE: 8

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Tyr Ala Ser His Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Gly His Ser Phe Pro Trp
                85                  90                  95

Thr Phe Gly Gly Gly Thr Lys Val Glu Ile Lys
            100                 105

<210> SEQ ID NO 9
<211> LENGTH: 366
<212> TYPE: DNA
<213> ORGANISM: Human and Mouse

<400> SEQUENCE: 9

```
caggtgcagc tggtgcaatc tgggtctgag ttgaagaagc ctggggcctc agtgaaggtt      60
tcctgcaagg cttctggata cgccttcact accactggca tgcagtgggt gcgacaggcc    120
cctggacaag gcttgagtg gatgggatgg atcaacaccc acagcgggt cccaaagtat      180 gtcgaggact tcaaaggacg gtttgtcttc tccttggaca cctctgtcag cacggcatat    240
ctgcagatca gcagcctaaa ggctgaggac actgccgtgt attactgtgc gagatctggc    300
aatgggaact atgacctggc atactttaag tattggggcc agggaacccct ggtcaccgtc   360 tcctca                                                                366
```

<210> SEQ ID NO 10
<211> LENGTH: 122

```
<212> TYPE: PRT
<213> ORGANISM: Human and Mouse

<400> SEQUENCE: 10

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Ala Phe Thr Thr Thr
             20                  25                  30

Gly Met Gln Trp Val Arg Gln Ala Pro Gly Gln Gly Leu Glu Trp Met
         35                  40                  45

Gly Trp Ile Asn Thr His Ser Gly Val Pro Lys Tyr Val Glu Asp Phe
     50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Ser Gly Asn Gly Asn Tyr Asp Leu Ala Tyr Phe Lys Tyr Trp
             100                 105                 110

Gly Gln Gly Thr Leu Val Thr Val Ser Ser
         115                 120

<210> SEQ ID NO 11
<211> LENGTH: 321
<212> TYPE: DNA
<213> ORGANISM: Human and Mouse

<400> SEQUENCE: 11
gaaattgtgt tgacacagtc tccagccacc ctgtctttgt ctccagggga aagagccacc      60
ctctcctgca gggccagtca gagtattagc gattacttac attggtacca acagaaacct     120
ggccaggctc ccaggctcct catctattac gcatcccact ccatctctgg catcccagcc     180
aggttcagtg gcagtgggtc tgggacagac ttcactctca ccactagcag cctagagcct     240
gaagattttg cagtttatta ctgtcagcat ggccactctt atccttggac cttcggaggg     300
gggaccaagg tggaaattaa a                                               321

<210> SEQ ID NO 12
<211> LENGTH: 107
<212> TYPE: PRT
<213> ORGANISM: Human and Mouse

<400> SEQUENCE: 12

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Ser Asp Tyr
             20                  25                  30

Leu His Trp Tyr Gln Gln Lys Pro Gly Gln Ala Pro Arg Leu Leu Ile
         35                  40                  45

Tyr Tyr Ala Ser His Ser Ile Ser Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His Gly His Ser Tyr Pro Trp
                 85                  90                  95

Thr Phe Gly Gly Gly Thr Lys Val Glu Ile Lys
             100                 105
```

-continued

```
<210> SEQ ID NO 13
<211> LENGTH: 366
<212> TYPE: DNA
<213> ORGANISM: Human and Mouse

<400> SEQUENCE: 13
cagatccagt tggtgcaatc tggacctgag ctgaagaagc ctggagagac agtcaggatc      60
tcctgcaagg cttctgggta tgccttcaca actactggaa tgcagtgggt gcaagagatg     120
ccaggaaagg gtttgaagtg gattggctgg ataaacaccc actctggagt gccaaaatat    180
gtagaagact tcaagggacg gtttgccttc tctttgaaa cctctgccaa cactgcatat     240
ttacagataa gcaacctcaa aaatgaggac acggctacgt atttctgtgt gagatccggg     300
aatggtaact atgacctggc ctactttgct tactggggcc aagggacact ggtcactgtc     360
tctgca                                                                366

<210> SEQ ID NO 14
<211> LENGTH: 324
<212> TYPE: DNA
<213> ORGANISM: Human and Mouse

<400> SEQUENCE: 14
gacattgttc tgactcagtc tccagccacc ctgtctgtga ctccaggaga tagagtctct      60
ctttcctgca gggccagcca gagtattagc gactacttac actggtatca acaaaaatca    120
catgagtctc caaggcttct catcaaatat gcttcccatt ccatctctgg gatcccctcc    180
aggttcagtg gcagtggatc agggtcagat ttcactctca gtatcaacag tgtggaacct    240
gaagatgttg gaatttatta ctgtcaacat ggtcacagct ttccgtggac gttcggtgga    300
ggcaccaagc tggaaatcaa acgt                                            324
```

ANTIBODIES AGAINST HUMAN CD40

This application is a continuation-in-part of, and claims priority back to, U.S. application Ser. No. 09/026,291 filed Feb. 19, 1998, now U.S. Pat. No. 6,051,228, said priority application hereby incorporated by reference in its entirety.

BACKGROUND OF THE INVENTION

Immune/inflammatory responses are mediated by a complex series of interactions. One receptor/ligand pair shown to be important in these processes is CD40/gp39. The gp39/CD40 interaction mediates a number of important signaling events between activated T cells and other effector cells of the immune system leading to amplification of an immune/inflammatory response. Responses to signaling through CD40 include T cell help to B cells in the humoral immune response, induction of cytokines by monocytes, and expression of adhesion molecules by endothelial cells.

CD40 is a type I cell surface receptor and a member of the tumor necrosis factor receptor (TNFR) supergene family. Though originally identified as a B cell antigen, CD40 is now believed to be expressed by all antigen presenting cells (APC), including dendritic cells, keratinocytes, and monocytes. CD40 is also expressed by cell types that can act as APC under certain conditions, such as vascular endothelial cells, or cells involved in direct interactions with T cells or T cell precursors such as thymic epithelial cells. More recently, it has also been reported that CD40 can be expressed by fibroblasts, eosinophils, and activated T cells. CD40 expression has also been seen in cancerous cells. Evidence for this is primarily derived from the identification of some carcinoma and melanoma derived cell lines which are CD40$^+$. (Clark and Ledbetter, *Proc. Natl. Acad. Sci.* (1986) 83:4494–98; Schriever et al., *J. Exp. Med.* (1989) 169:2043–58; Caux et al., *J. Exp. Med.* (1994) 180:1263–72; Alderson et al., *J. Exp. Med.* (1993) 178:669–74; Young et al., *Int. J. Cancer* (1989) 43:786–94; Paulie et al., *Cancer Immunol. Immunother.* (1985) 20:23–28; Denfeld et al., *Eur. J. Immunol.* (1996) 26:2329–34; Gaspari et al., *Eur. J. Immunol.* (1996) 26:1371–77; Peguet-Navarro et al., *J. Immunol.* (1997) 158:144–52; Hollenbaugh et al., *J. Exp. Med.* (1995) 182:33–40; Galy and Spits, *J. Immunol.* (1992) 149:775–82; Yellin et al., *J. Leukoc. Biol.* (1995) 58:209–16; Ohkawara et al., *J. Clin. Invest.* (1996) 97:1761–66).

This expression pattern differs from the expression pattern of the ligand of CD40, namely gp39. A member of the tumor necrosis factor (TNF) family of proteins, gp39 is a type II cell surface protein that is transiently expressed by activated T cells. Gp39 is also known as CD40L, TRAP, T-BAM, and now has the official CD designation from the Leukocyte Workshop of CD154. In in vitro assays, gp39 appears on the T cells approximately 2–4 hours following T cell activation and levels peak at 6–8 hours. The protein level then rapidly declines and is undetectable 24 hours after stimulation. Gp39 expression has also been detected on eosinophils and mast cells. (Noelle et al., *Proc. Natl. Acad. Sci.* (1992) 89:6550–54; Hollenbaugh et al., *EMBO J.* (1992) 11:4313–21; Spriggs et al., *J. Exp. Med.* (1992) 176:1543–50; Grafet al., *Eur. J. Immunol.* (1992) 22:3191–94; Covey et al., *Mol. Immunol.* (1994) 31:471–84; Castle et al., *J. Immunol.* (1993) 151:1777–88; Roy et al., *J. Immunol.* (1993) 151:2497–2510; Gauchat et al., *Nature* (1993) 365:340–43; Gauchat et al., *Eur. J. Immunol.* (1995) 25:863–65; Koshy et al., *J. Clin. Invest.* (1996) 98:826–37; Desai-Mehta et al., *J. Clin. Invest.* (1996) 97:2063–73).

CD40 is a potent signaling receptor, providing a mechanism for activated T-cells to regulate a wide range of immune and inflammatory responses. In vitro and in vivo studies with recombinant forms of the gp39 ligand and with anti-CD40 mAbs have shown that signaling through this receptor leads to a cellular response in all known CD40$^+$ cells, and that outcome not only varies by cell type but is also modulated by concurrent signaling events through other receptors. In B cells, for example, CD40 signaling in conjunction with signaling by the IL-4 receptor leads to B cell proliferation and production of antibodies of the IgE isotype, while CD40 signaling in conjunction with signals from the IL-10 receptor lead to B cell proliferation and production of antibodies of the IgG isotype (Gordon et al., *Eur. J. Immunol.* (1987) 17:1535–38; Rousset et al., *J. Exp. Med.* (1991) 173:705–710; Jabara et al., *J. Exp. Med.* (1990) 172:1861–64; Gascan et al., *J. Immunol.* (1991) 147:8–13). Gp39 mediated CD40 signaling may play a role in cellular immunity through the induction of CD80 and CD86, important T cell costimulatory molecules which bind CD28 and CTLA4 (Goldstein et al., *Mol. Immunol.* (1996) 33:541–52).

The CD40/gp39 receptor/ligand system is one of the many systems which are involved in the productive interaction between activated T cells and other cells of the immune system. However, a number of findings suggest that this interaction is unique and central to the regulation of the humoral immune response in humans. In particular, defects in gp39 expression or structure have been shown to be the cause of the human immunodeficiency known as X-linked hyper IgM (X-HIM) syndrome. This immunodeficiency is characterized by the inability of affected individuals to produce antibodies other than those of the IgM isotype, indicating that the productive interaction between gp39 and CD40 is required for an effective humoral immune response (Allen et al., *Science* (1993) 259:990–93; Aruffo et al., *Cell* (1993) 72:291–300; Di Santo et al., *Nature* (1993) 361:541–43; Fuleihan, et al., *Proc. Natl. Acad. Sci.* (1993) 90(6):2170–73; Korthauer et al., *Nature* (1993) 361:539–541; Notarangelo et al., *Immunodef Rev.* (1992) 3:101–22). Likewise, recent data indicate that non-X-linked HIM syndrome in humans is caused by defects in the CD40 molecule. Using gene knockout technology, mice lacking CD40 or gp39 have been generated. These mice exhibit a phenotype which has the same characteristics as HIM syndrome suggesting that mice can be an appropriate model in which to test the effects of in vivo treatment with either anti-CD40 or anti-gp39 mAbs that block the interaction between CD40 and gp39 (Kawabe et al., *Immunity* (1994) 1:167–78; Xu et al., *Immunity* (1994) 1:423–431; Renshaw et al., *J. Exp. Med.* (1994) 180:1889–1900; Castigli et al., *Proc. Natl. Acad. Sci. USA* (1994) 91:12135–39).

The effects of in vivo inhibition of the CD40/gp39 interaction have been extensively studied in normal mice and mouse models of disease using a hamster antimouse gp39 mAb (MR1). The immunosuppressive capacity of the antibody is reflected in its ability to completely inhibit the humoral immune response to T-cell dependent antigens (Foy, et al., *J. Exp. Med.* (1993) 178:1567–75). Several mouse models of inmmune diseases have also been shown to be inhibited by treatment with the antibody, including those mediated by cellular immune responses. Disease models shown to be inhibited by treatment with anti-gp39 include collagen induced arthritis, experimental allergic encephalomyelitis, lupus nephritis, transplant rejection, and graft vs. host disease (Durie et al., *Science* (1993) 261:1328–30; Berry, et al., unpublished; Gerritse et al., *Proc. Nati. Acad. Sci. USA* (1995) 93:2499–504; Mohan et al., *J. Immunol.* (1995) 154:1470–1480; Larsen et al., *Transplantation* (1996) 61:4–9; Hancock et al., *Proc. Natl. Acad.*

Sci. USA (1996) 93:13967–72; Parker et al., *Proc. Natl. Acad. Sci. USA* (1995) 92:9560–64; Durie, et al., *J. Clin. Invest.* (1994) 94:1333–38; Wallace, et al., unpublished). The role of CD40/gp39 in the amplification of a cellular immune response may be direct, through the stimulation of a subset of activated T cells that are capable of expressing CD40, or indirect, through induction of cytokines and the expression of important co-stimulatory cell surface molecules such as CD80 and CD86, which bind to the T cell receptors CD28 and CTLA-4. The anti-inflammatory effects of the inhibitor have been demonstrated by studies in a mouse model of oxygen-induced lung injury. The effects on inflammation in vivo are suggested by the in vitro results demonstrating stimulation of CD40 on vascular endothelial cells and monocytes which results in the expression of cell adhesion molecules, nitric oxide (NO), matrix metalloproteinases and proinflammatory cytokines (Kiener et al., *J. Immunol.* (1995) 155:4917–25; Malik et al., *J. Immunol.* (1995) 156:3952–60; Hollenbaugh et al., *J. Exp. Med.* (1995) 182:33–40).

Studies with anti-human gp39 mAbs in monkeys have shown that biologics which inhibit the interaction between gp39 and CD40 in vivo are effective immunosuppressive agents in primates. Anti-gp39 mAbs have been demonstrated to be effective in the inhibition of antibody responses to T-cell dependent antigens, and to protect allografts from rejection, results analogous to that seen in rodents.

Collectively the above studies have shown that agents which disrupt the interaction between gp39 and CD40 would be potent immunosuppressive and anti-inflammatory agents. Therefore, there exists a need in the art for an effective method of blocking the CD40/gp39 interaction to provide an immunosuppressive or anti-inflammatory effect. A purpose of the present invention is to provide an antibody which blocks the interaction between gp39 and CD40.

Another object of the present invention is to provide a chimeric antibody effective in blocking the interaction between CD40 and gp39.

An additional object of the present invention is to provide a humanized antibody effective in blocking the interaction between CD40 and gp39.

A further object of the present invention is a method of modulating an immune response by administering an antibody, chimeric antibody, or humanized antibody of the present invention. The method may be useful in treating any number of autoimmune diseases, as well as skin or other organ transplantation.

SUMMARY OF THE INVENTION

The present invention comprises a novel antibody, more preferably a chimerized anti-human CD40 monoclonal antibody (mAb), which blocks the interaction between gp39 and CD40. In one embodiment of the present invention, a particularly preferred chimerized anti-human CD40 mAb is referred to as "chi220". Chi220 is a chimeric antibody comprising murine variable and human kappa and gamma 1 constant regions. Chi220, like its parent mouse mAb, binds to CD40 and, as a result, effectively blocks humoral immune responses to T cell-dependent antigens in a dose dependent fashion.

Also encompassed within the scope of the present invention are humanized anti-CD40 antibodies which block the interaction between gp39 and CD40. In one embodiment of the present invention, a humanized antibody is referred to as F4; in another embodiment the humanized antibody is referred to as L3.17. The preferred humanized antibodies of the present invention comprise human variable heavy and variable light regions with murine CDR's grafted therein.

The anti-CD40 antibodies of the present invention, preferably the chimeric and humanized antibodies disclosed herein, are effective in modulating humoral immune responses against T cell-dependent antigens, collagen induced arthritis, and transplant rejection. The anti-CD40 antibodies of the present invention, preferably the chimeric and humanized antibodies disclosed herein, are also useful for their anti-inflammatory properties (which are similar to those seen with anti-gp39).

The antibodies of the present invention, particularly the anti-CD40 chimeric antibody chi220 and the anti-CD40 humanized antibodies F4 and L3.17, have wide therapeutic applications, including autoimmune diseases, inflammatory diseases and transplantation. Because of the expression of CD40 seen on malignant cells of several histologic types, the potential oncology applications of anti-CD40 antibodies, particularly the chimeric and humanized antibodies of the present invention, are evident.

The following abbreviations are used throughout the present application and are known by those skilled in the art: APC (antigen presenting cell); CDR (complementary-determining region); CHO (chinese hamster ovary); CIA (collagen-induced arthritis); Cmax (maximum serum concentration); COS (African green monkey fibroblast cell line); DMARD (disease modifying anti-rheumatic drugs); ELISA (enzyme-linked immunosorbent assay); EPT (end point titers); EU (endotoxin units); Fab (antigen binding fragment); FITC (fluoroisothiocyanate); Hu (humanized); h106-2 (humanized anti-gp39 mAb); HAMA (human-anti-mouse antibodies); im (intramuscular); KLH (keyhole limpet hemocyanin); mAb (monoclonal antibody); MTX (methotrexate); OVA (ovalbumin); PBS (phosphate buffered saline); PCR (polymerase chain reaction); PE (phycoerytherin); sc (subcutaneous); SDS-PAGE (sodium dodecyl sulfate polyacrylamide gel electrophoresis); SEC (size exclusion chromatography); SRBC (sheep red blood cells); STR (stirred tank reactor); TNF (tumor necrosis factor); VL (antibody light chain variable region); VH (antibody heavy chain variable region).

A nucleic acid encoding a preferred light chain of a chimeric antibody of the present invention (chimeric antibody 2.220) has been deposited with the American Type Culture Collection and given the Accession Number ATCC 203630. A nucleic acid encoding a preferred heavy chain of a chimeric antibody of the present invention (2.220) has been deposited with the American Type Culture Collection and given the Accession Number ATCC 203629.

A nucleic acid encoding a preferred light chain of a humanized antibody of the present invention (humanized antibody F4) has been deposited with the American Type Culture Collection and given the Accession Number ATCC 203628. A nucleic acid encoding an additional preferred light chain of a humanized antibody of the present invention (humanized antibody L3.17) has been deposited with the American Type Culture Collection and given the Accession Number ATCC 203774. A nucleic acid encoding a preferred heavy chain of a humanized antibody of the present invention (F4 and L3.17) has been deposited with the American Type Culture Collection and given the Accession Number ATCC 203631.

The deposit(s) referred to herein will be maintained under the terms of the Budapest Treaty on the International Recognition of the Deposit of Micro-Organisms for purposes of Patent Procedure. These deposits are provided merely as convenience to those of skill in the art and are not an admission that a deposit is required under 35 U.S.C. §112. The sequence(s) of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

All references cited in this application, whether supra or infra, are herein incorporated by reference in their entirety.

BRIEF DESCRIPTION OF THE DRAWINGS

FIG. 3 shows the anti-SRBC antibody response in primates.

FIG. 4a shows the sequence of the light chain variable region of chi220 in bold (SEQ ID NO:1), and FIG. 4b shows the sequence of the heavy chain variable region of chi220 in bold (SEQ ID NO:2). The underlined sequences in FIGS. 4a and 4b are the inserted signal sequences of the human antibody with the closest homology which had been used as humanization template.

FIG. 5 shows the results of in vitro assays testing chimeric and humanized antibody of the present invention.

FIG. 6 shows the IgM Anti-SRBC antibody response. FIG. 6a shows the results from monkeys that received 10, 40 or 100 mg/kg chi220. FIG. 6b shows the results from monkeys that received 0.1 or 1 mg/kg chi220.

FIG. 7 shows the IgG Anti-SRBC antibody response.

FIG. 8 shows the anti-OVA antibody response in primates.

FIG. 9 shows the anti-KLH antibody response in primates.

FIG. 13 provides a nucleic acid sequence (SEQ ID NO:5) for an expression vector capable of expressing a heavy chain of a chimeric antibody of the present invention. The start ATG (nucleotides 1000–1002), encoding the start Met of the inserted signal sequence of the human antibody, is in bold. Nucleotides 1057 through 1422 (SEQ ID NO:13), underlined, provide a preferred nucleic acid sequence encoding a variable heavy chain of an antibody of the present invention.

FIG. 14 provides a nucleic acid sequence (SEQ ID NO:6) for an expression vector capable of expressing a light chain of a chimeric antibody of the present invention. The start ATG (nucleotides 1005–1007), encoding the start Met of the inserted signal sequence of the human antibody, is in bold. Nucleotides 1065 through 1388 (SEQ ID NO:14), underlined, provide a preferred nucleic acid sequence encoding a variable light chain of an antibody of the present invention.

FIG. 15 shows an alignment of murine anti-CD40 variable regions and a human template sequences. The amino acid sequences of the murine anti-CD40 H and L chain variable regions were used to identify homologous human germline sequences. The numbering of residues and the definition of CDRs (underlined) were based on Kabat et al. (Kabat, E. A., et al., (1991) Sequences of proteins of immunological interest (5th Ed). Washington DC: United States Department of Health and Human Services; Kabat, E. A., et al., (1977) *J Biol. Chem.* 252:6609–6616). Differences in sequence are indicated by vertical lines and framework positions characterized in the combinatorial expression library are marked with an asterisk.

DETAILED DESCRIPTION OF THE INVENTION

Figure 1:
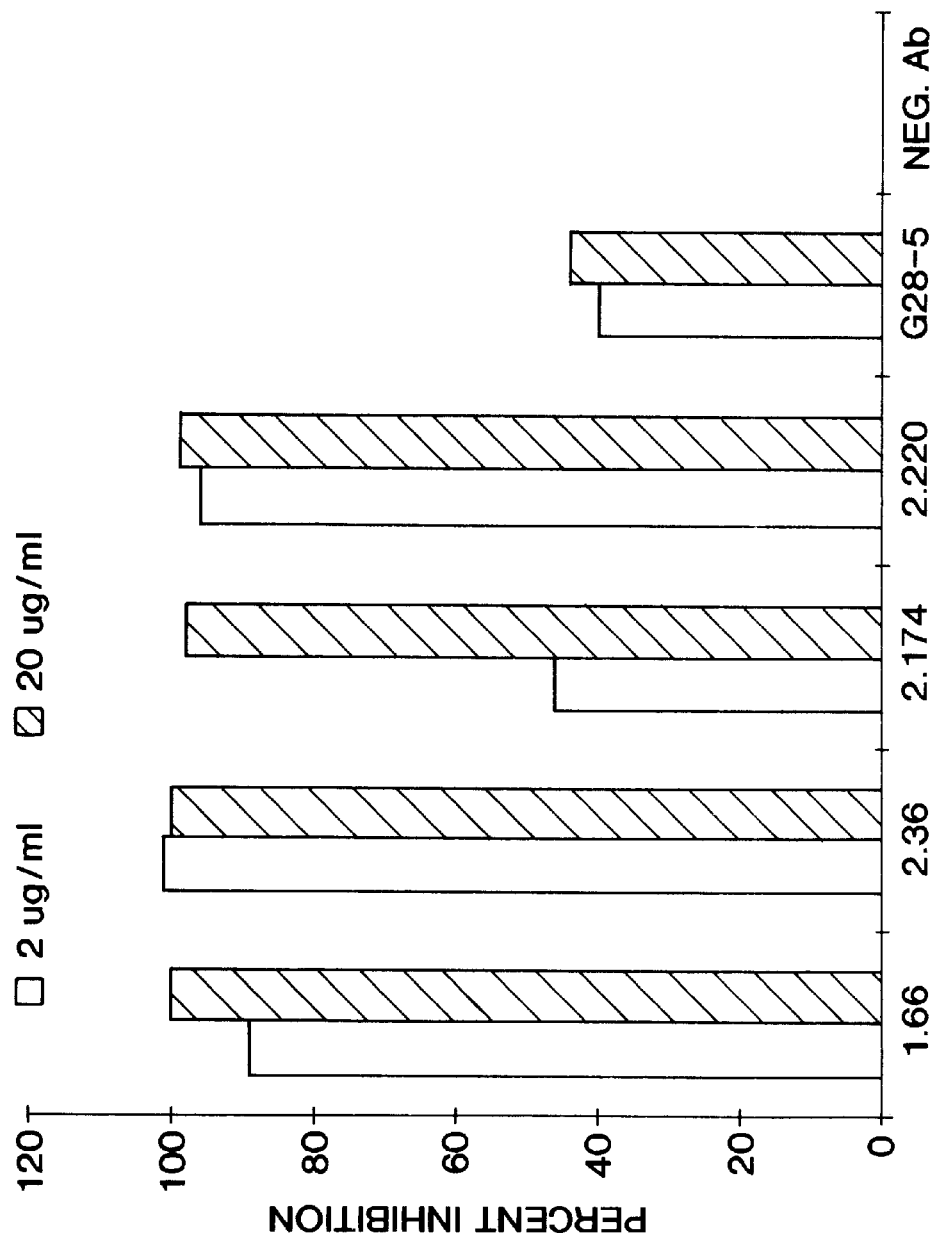
FIG. 1 shows the inhibition of sgp39 binding to Raji cells by anti-human CD40 mAbs.

The present inventors have developed chimeric and humanized anti-human CD40 antibodies with immunosuppressive properties. Such anti-human CD40 antibodies have obvious applications as a therapeutic. The present inventors have also developed a closely matched anti-mouse CD40 mAb (closely matched to the antihuman CD40 mAb) which is useful to study the effects of anti-CD40 mAb therapy in a number of mouse models of immune and inflammatory disease. Development of anti-CD40 antibodies is complicated by the fact that CD40 is a potent signaling molecule. Antibodies that bind to this antigen can be categorized based on the ability to stimulate CD40 signaling as well as the ability to block the CD40/gp39 interaction.

Applicants' anti-human CD40 mAb, which blocks the CD40/gp39 interaction, was selected from an extensive panel of anti-CD40 mAbs. The antibody, labeled 2.220, was chimerized and humanized. "Chimeric" antibodies comprise a light chain and a heavy chain: the light chain is comprised of a light chain variable region and a light chain constant region; the heavy chain is comprised of a heavy chain variable region and a heavy chain constant region. Chimeric antibodies comprise variable regions from one species and constant regions from another species (for example, mouse variable regions joined to human constant regions). (See, e.g., U.S. Pat. Nos. 4,816,397 and 4,816,567). Each of the light chain variable region (VL) and heavy chain variable region (VH) consists of "framework" regions interrupted by three hypervariable regions called "complementarity determining regions" or "CDRs". "Humanized" antibodies comprise antibodies with human framework regions combined with CDRs from a donor mouse or rat immunoglobulin. (See, e.g., U.S. Pat. No. 5,530,101) Encompassed within the scope of the present invention are humanized antibodies which comprise CDRs derived from the murine variable chains disclosed herein.

The most straightforward approach to humanizing an antibody consists of grafting the CDRs from the donor mAb onto a human framework (Jones, P. T., et al., (1986) Nature 321:522–525). However, certain framework residues support CDR structure, and contact antigen grafting murine CDRs onto human framework templates may diminish the binding activity of the resulting humanized mAb (Foote, J., et al., (1992) *J. Mol. BioL.* 224:487–499). Assessing the potential contribution of specific framework residues to antibody affinity poses two problems. First, for a particular mAb it is difficult to predict which framework residues serve a critical role in maintaining the affinity and specificity. Second, for framework positions that differ between the parent mAb and the human template it is difficult to predict whether the amino acid derived from the murine parent or the human template will yield a more active mAb. Consequently, antibody humanization methods that rely exclusively on structural predictions are not always successful.

The prior art contains a description of a general antibody engineering strategy that addresses the difficulty of maintaining antibody binding activity following humanization (Rosok, M. J., et al., (1996) *J. Biol. Chem.* 271:22611–22618). Potentially important framework residues that differ between the parent mAb and the human template are characterized in a single step by synthesizing and expressing a combinatorial antibody library that contains all possible combinations of parent and human template amino acids at the framework positions in question. Variants displaying the optimal framework structure are identified by screening and subsequently, optimal framework structure(s) are determined by DNA sequencing. Typically, sequencing multiple active clones reveals critical framework positions that require the expression of a particular amino acid. Conversely, the expression of a murine or human amino acid at a library framework position at an equivalent frequency in the active clones is consistent with a less important function for that particular framework position. Thus, a humanized version of the antibody that preserves the binding activity of the parent mAb is rapidly identified based on functional binding.

The processes of antibody humanization and affinity maturation are often performed in discreet steps (Rosok (1996), supra; Yelton, D. E., et al., (1995) *J. Immunol.* 155:1994–2004; Wu, H., et al., (1998) *Proc. Natl. Acad. Sci. USA* 95:6037–6042; Baca, M., et al., (1997) *J. Biol. Chem.* 272:10678–10684; Marks, J. D., et al., (1992) *J. Biol. Chem.* 267:16007–16010). Using a modified strategy described below, multiple humanized versions of the murine mAb 2.220 displaying affinities equivalent to or better than the chimeric Fab were generated.

Applicants' chimeric anti-CD40 antibody of the present invention is referred to herein as "chi220". Applicants' closely matched anti-mouse CD40 mAb is referred to herein as "7E1". Applicants' humanized anti-CD40 antibodies of the present invention are referred to herein as "F4" and "L3.17".

Two different isotype variants of 7E1 were generated. These two variants of 7E1 are useful in examining the role of the Fc portion of the molecule in anti-CD40 mAb therapy in preclinical models of immune and inflammatory diseases. The generation of the anti-mouse CD40 mAb, the criteria used to select one which matched the properties of chi220, the generation of the isotype variants of the mAb and their in vivo activity in mouse models of immune disease are also presented herein. Studies with both chi220 and its parent murine mAb 2.220 in monkeys, as well as studies with 7E1 in mice, showed that these anti-CD40 mAbs are potent immunosuppressive agents, and will be discussed in more detail below. The studies described herein were performed using standard technology known by those skilled in the art.

In summary, Applicants' antibodies have been shown to suppress a humoral immune response in monkeys. Likewise, two isotype variants of a closely matched anti-mouse CD40 mAb, 7E1, showed immunosuppressive activity in a number of preclinical models of human disease. Taken together, these findings indicate that chi220, F4 and L3.17 are useful for clinical application in the treatment of autoimmune diseases and transplantation.

The following examples are for illustrative purposes only and do not limit the scope of Applicants invention, which is defined only by the claims.

EXAMPLE 1

Selection of Murine Anti-Human CD40 Antibody

A. Isolation and In Vitro Characterization

A panel of monoclonal antibodies was generated against human CD40 using standard hybridoma technology with human CD40 fusion protein as the immunogen. Antibodies were screened for binding to CD40 using both a CD40$^+$ cell line and fusion proteins. Assays of gp39 binding to CD40 and functional assays of stimulation through CD40 were used to characterize cloned antibodies. Selected antibodies were then characterized for crossreactivity with primate cells to assess the suitability of the antibodies for use in primate preclinical models.

1. Immunization and Fusion

Two fusions were performed to generate hybridomas producing anti-human CD40 mAbs. Immunizations to generate immune lymphocytes were carried out in 6–8 week old female BALB/c mice using as the immunogen a recombinant fusion protein consisting of the extracellular domain of human CD40 fused to the hinge, CH2 and CH3 domains of a murine IgG2b antibody (hCD40-mG2b).

For fusion 40-1, the mouse was initially immunized subcutaneously at 3–4 sites with an emulsion (total of 200 ul) of 30 ug hCD40-mG2b in complete Freund's adjuvant. The animal was similarly boosted on day 21 with hCD40-mG2b in incomplete Freund's adjuvant and then given a final pre-fusion immunization on day 37 by intravenous injection of 30 ug of hCD40-mG2b in PBS. Immunizations for fusion 40-2 were similarly performed except that Ribi adjuvant (R-730, Universal Biological Ltd.) was substituted for Freund's adjuvant. Booster immunizations were on days 21 and 42 with the final pre-fusion boost on day 58.

Three days following final booster injections, leukocytes from the spleen and lymph nodes were harvested and fused at a 3:1 ratio with X63-Ag8.653 mouse myeloma cells using standard methods (Kearney et al., *J. Immunol.* (1979) 123:1548–50; Lane, *J. Immunol.* (1985) 81:223–28). Cell suspensions from each fusion were seeded into ten 96-well cell culture plates at a plating density of approximately 170,000 total cells (pre-fusion) per well.

2. Screening and Cloning

Two assay formats were used to identify mAbs with specificity for native human CD40. Cell culture supernatants from all wells were initially screened for their ability to bind to a CD40 positive, E13V-transformed human B cell line (1A2–2C) in an ELISA-based format. Each supernatant was then tested in an ELISA based format for reactivity with a purified, recombinant fusion protein consisting of the extracellular domain of human CD40 fused to the hinge, CH2 and CH3 domains of a human IgG1 antibody, hCD40-Ig, and a similarly constructed irrelevant human Ig fusion protein, Leu8-hIg (Hollenbaugh, et al., *EMBO J.* (1992) 11:4313–4321). Reactivity with the former and not the latter fusion protein, coupled with the cell binding data, established the presence of antibody specific for native CD40 in approximately 200 master wells.

A key functional property for the desired anti-CD40 mAb was the capacity to completely block the interaction of CD40 and its ligand, gp39. Thus, as the next step in antibody selection, all CD40 specific master well supernatants were assessed for their ability to inhibit the binding of the soluble, recombinant murine CD8-human gp39 fusion protein, sgp39, to immobilized hCD40-Ig in an ELISA-based format. Those that completely inhibited this interaction were subsequently titrated in the same format to establish which wells contained the highest titer of inhibiting antibody. From this analysis, ten of the most strongly inhibiting master wells were selected for cloning.

Cloning of the appropriate antibody secreting cells was accomplished in a two step process. Cells from each master well were first "minicloned" at a seeding density of 10 cells/well after which the highest titered, CD40-specific "miniclone" well was formally cloned by a limiting dilution method.

3. Further Characterization

Six assay fornats were used to further characterize the antibodies. These were inhibition of sgp39 binding to human B cells, inhibition of B cell proliferation induced by sgp39 plus anti-IgM, inhibition of in vitro antibody synthesis by B cells induced by activated T cells, direct costimulation of B cells with anti-IgM, costimulation of B cells with anti-IgM in the presence of cross-linking anti-kappa light chain antibody, and costimulation of B cells with anti-IgM in the presence of a second anti-CD40 mAb, G28–5. This mAb was known to possess strong costimulatory activity and to incompletely block CD40/gp39 interaction. It has been included for comparison purposes in many of these assays.

This analysis led to the selection of four mAbs: 1.66 (IgG2b), 2.36 (IgG2a), 2.174 (IgG1) and 2.220 (IgG2a). Tests were run to characterize the mAbs. In one experiment, cells from the human B cell line Raji were incubated with 2 or 20 μg/ml of various anti-CD40 mAbs followed by a second incubation in undiluted COS cell supernatant containing mCD8-gp39 fusion protein (sgp39). Bound sgp39 was detected by further incubation of the cells with a FITC labeled anti-mCD8 mAb and analysis of the cells on a FACScan flow cytometer (Becton Dickinson). Percent inhibition was calculated by dividing mean fluorescence of samples incubated with antibody by the mean fluorescence of samples without antibody in the first incubation (FIG. 1).

As shown in FIG. 1, each of these four mAbs was capable of completely inhibiting the binding of sgp39 fusion protein to a human B cell line expressing high levels of CD40, although in the case of 2.174, a relatively high concentration of antibody was required for complete blockade. Similar data were obtained using human tonsillar B cells. These data were paralleled by two fimctional assays. First, it was shown that each mAb was able to completely block sgp39-mediated costimulation of human tonsillar B cells. Second, each significantly inhibited the production of IgG and IgM in an in vitro T cell-dependent B cell antibody synthesis assay.

Three of the four antibodies showed limited ability to costimulate B cell proliferation in the presence of anti-IgM. MAb 2.220 was more consistent in its ability to induce weak costimulatory activity. With the addition of an anti-kappa light chain antibody, used to cross-link the anti-CD40 mAbs, 2.36 gained significant costimulatory activity, while the activity of other three antibodies was not affected. The costimulatory ability of G28–5 was shown to be differentially modulated when it was paired in combination with each of the four new anti-CD40 mAbs. MAbs 1.66 and especially 2.174 enhanced G28–5 costimulation, whereas 2.220 and 2.36 suppressed it.

Following selection based on evaluations in human in vitro systems, the four anti-CD40 mAbs were further examined for their suitability for in vivo evaluation in non-human primate studies. Two key points of analysis were the relative potency of each for binding to primate B cells and suppression of in vitro, T cell-dependent B cell antibody synthesis. It was found that all four mAbs crossreacted with cynomolgus macaque (*Macaca fascicularis*) B cells. 2.36 and 2.220 bound with higher avidity than 2.174 and 1.66. Lower apparent binding of mAbs 2.174 and 1.66 was not due to their particular isotypes, as other isotype-matched anti-CD40 mAbs demonstrated binding levels comparable to 2.36 and 2.220 (e.g., G28–5 and 2.118). These results were in contrast to that observed with human B cells where each of the mAbs demonstrated comparable binding. The ability of the four mAbs to suppress antibody synthesis by monkey B cells was found to parallel the ability to bind.

B. In Vivo Characterization

Two studies were performed in non-human primates using the murine antihuman CD40 mAbs to assess the suitability of anti-CD40 as an immunosuppressive agent and to select the appropriate antibody for further development. First, the in vivo clearance and acute toxicity of the four selected anti-CD40 mAbs were compared. These results were used to select two antibodies, 2.36 and 2.220, that were then tested in a second study designed to assess efficacy in the inhibition of the antibody response to a T-dependent antigen and acute toxicity.

Figure 2:
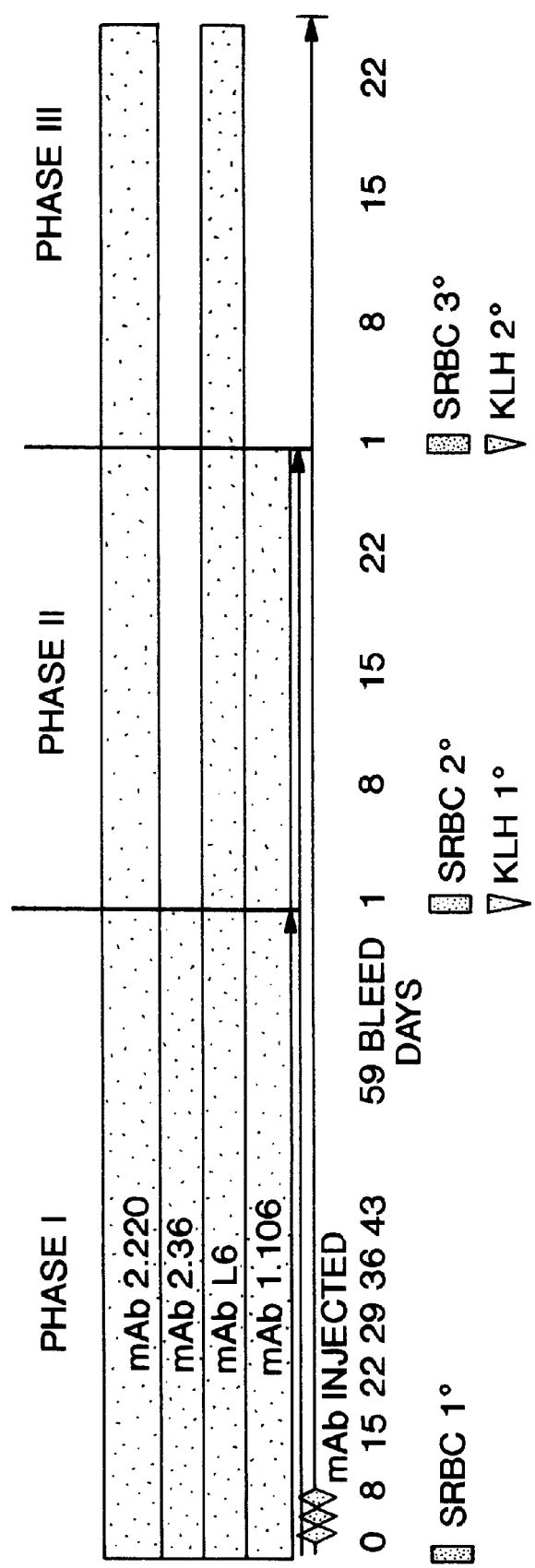
FIG. 2 is a schematic outlining the primate study protocol. Days of treatment are indicated with diamonds. Immunizations with SRBC and KLH are indicated with rectangles and triangles, respectively. Animals treated with 2.36 were not studied past Phase I and animals treated with 1.106 were not studied past Phase II.

Primate Efficacy Study with 2.36 and 2.220 Based upon previous findings, mAbs 2.36 and 2.220 were evaluated for their ability to suppress a T-dependent antibody response following intravenous administration to cynomolgus monkeys. This study was divided into three phases (FIG. 2). In Phase I, four groups consisting of one or two male and two female cynomolgus monkeys each were immunized intravenously on day 1 with sheep red blood cells (SRBCs), and then treated with 20 mg/kg of mAb 2.36, 2.220, 1.106 (IgG1 murine anti-human gp39, positive control), or L6 (IgG2a murine anti-human tumor antigen, negative control) on days 1, 3, and 5. IgM and IgG titers to the SRBC immunogen, serum levels of test and control articles, the presence of anti-test and control article antibodies, serum immunoglobulin levels, peripheral blood leukocyte counts, and the frequencies of various subpopulations of peripheral blood lymphocytes were determined. In phase II, after the control and test articles had cleared, the animals were immunized with SRBCs and a second antigen, keyhole limpet hemocyanin (KLH), to assess the induction of immunological tolerance and the reversibility of the observed immunosuppression. In phase III, selected animals were reimmunized to determine if the initially suppressed anti-SRBC antibody response recovered following an additional challenge with SRBCs and to assess the secondary antibody response to KLH.

Figure 3A:
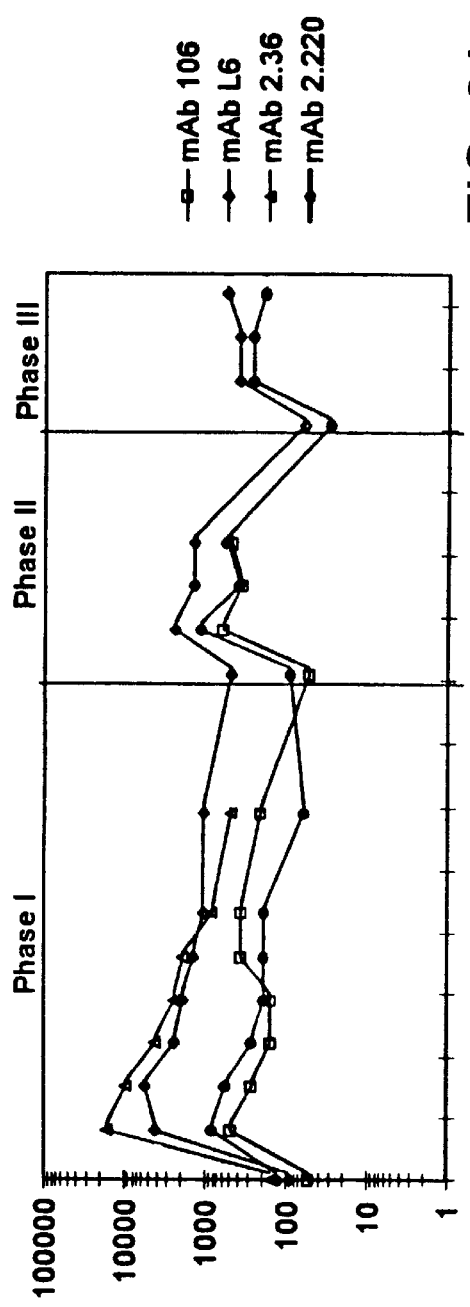
FIG. 3a shows the results of analysis for IgM anti-SRBC antibodies.
Figure 3B:
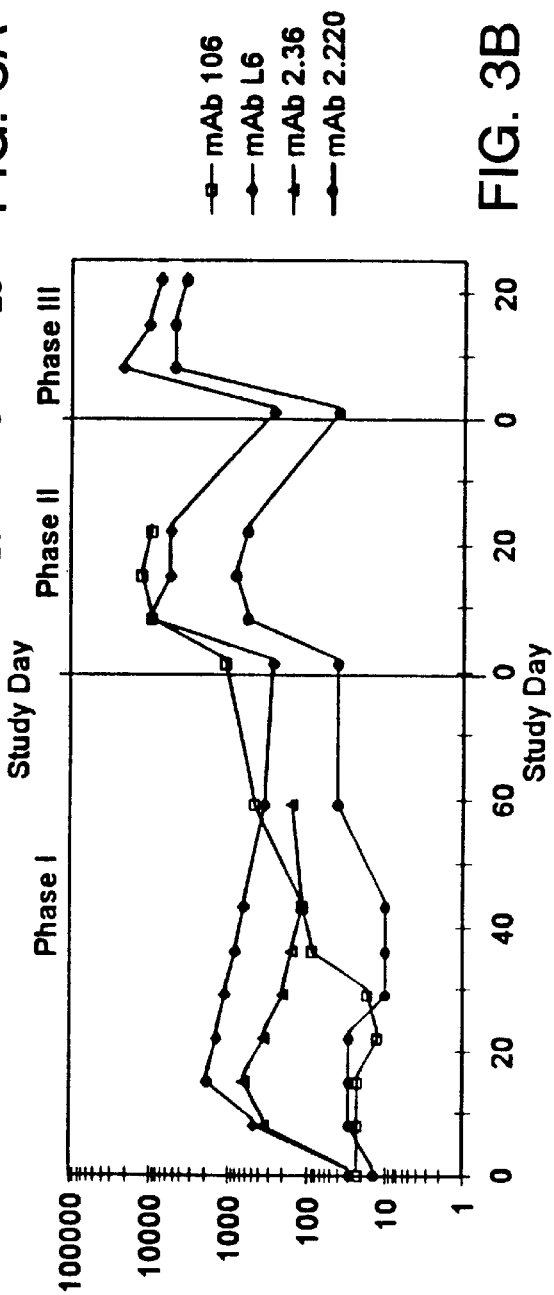
FIG. 3b shows the results of analysis for IgG anti-SRBC antibodies.

An experiment was performed to show that MAb 2.220 significantly suppressed the primary antibody response to SRBCs (FIG. 3). Monkeys were treated with 20 mg/kg of either mAb 1.106, L6, 2.36 or 2.220 on Phase I Days 1, 3, and 5. Monkeys were immunized with SRBC on Day 1 of Phase I, II and III. FIG. 3a shows the results of serum samples that were analyzed for IgM anti-SRBC antibodies; FIG. 3b shows the results of serum samples that were analyzed for IgG anti-SRBC antibodies. Data are expressed as the geometric mean anti-SRBC titer for each group (n=3 or 4).

The peak primary response was inhibited 85% and 98% for IgM and IgG, respectively. Following clearance of mAb 2.220 in serum to below detectable levels, the peak secondary response to SRBCs was still inhibited 79% and 56% for IgM and IgG, respectively, compared to the negative control response in Phase I. This was in contrast to the positive control, mAb 1.106, with which a strong secondary antibody response to SRBCs was observed. The tertiary response to SRBCs was not inhibited, indicating that mAb 2.220 induced a prolonged immunosuppression, but not immunological tolerance. All animals immunized with KLH had a primary and secondary anti-KLH response, suggesting that the immunosuppression was reversible. Animals treated with 2.36 were not included in phase II because there was no significant inhibition seen in phase I of the study.

Mean peak serum concentrations, occurring immediately after the last dose, were 744 and 405 µg/ml for mAbs 2.220 and 2.36, respectively. Whereas mAb 2.36 cleared from the serum to below detectable levels by day 15, mAb 2.220 did not clear until day 29. Both mAbs 2.36 and 2.220 were immunogenic.

There were no drug-related clinical observations, changes in body weight or food consumption, or alterations in hematology or serum Ig levels in any animal. The only drug-related findings observed were transient 70% and 43% decreases in the percentages of peripheral B cells with mAbs 2.36 and 2.220, respectively. Recovery of B cells to normal levels occurred within 2–3 weeks post-treatment.

In summary, mAb 2.220 significantly suppressed the antibody response to SRBCs and 2.36 did not. Although mAb 2.220 induced a prolonged antigen-specific immunosuppression, it was reversible. Based on these findings, mAb 2.220 was selected for futher development.

EXAMPLE 2

Generation of Chimeric Antibody chi220

To address immunogenicity of the murine anti-human mAb 2.220, recombinant forms in which variable regions are fused to human constant regions were generated and compared for in vitro efficacy. The two approaches used were generation of a chimeric antibody, containing the unaltered murine variable regions, and humanized forms in which murine hypervariable regions (CDRs) are grafted on human framework sequences within the variable regions. Chimeric antibodies retain the antigen binding properties of parent antibody, but may have a greater likelihood of being immunogenic. Humanized antibodies are less likely to be immunogenic, but mutations introduced in the humanization can affect antigen binding.

A. Construction and In Vitro Characterization of Chimeric and Humanized Antibodies The VL and VH regions from the anti-CD40 mAb 2.220 were obtained by PCR. cDNA was generated from RNA isolated from the hybridoma expressing the 2.220 mAb using an IgG1-specific or a Cκ-specific anti-sense primer to obtain the VH or VL regions, respectively. A poly-G tail was added to these single stranded cDNAs. The variable regions were then amplified by PCR using as a sense primer an oligonucleotide containing a poly-C sequence, complimentary to the poly-G tail, and a nested set of antisense primers. The PCR product obtained was then inserted into a bacterial vector using restriction sites included in the primers. Multiple clones were then sequenced by dideoxynucleotide sequencing. Two independent experiments were performed, beginning at the RNA stage and the sequences obtained were the same.

To generate a chimeric form of the antibody, the variable regions were amplified by PCR using primers that introduced a sequence encoding the signal sequence of the human antibody found to most closely match the 2.220 sequence, as shown in FIG. 4. The underlined portions of the light chain variable sequence (FIG. 4a) and the heavy chain variable sequence (FIG. 4b) designate the inserted signal sequences of the human antibody with the closest homology to murine 2.220. These PCR products were inserted into a vector containing sequences encoding the constant regions of human kappa or of human γ1 to generate complete light or heavy chain, respectively. The vectors also contained appropriate drug resistance genes for the generation and amplification of stable lines expressing the protein. Protein for initial characterization was produced by transient expression from COS cells followed by Protein A purification.

Figure 12A:
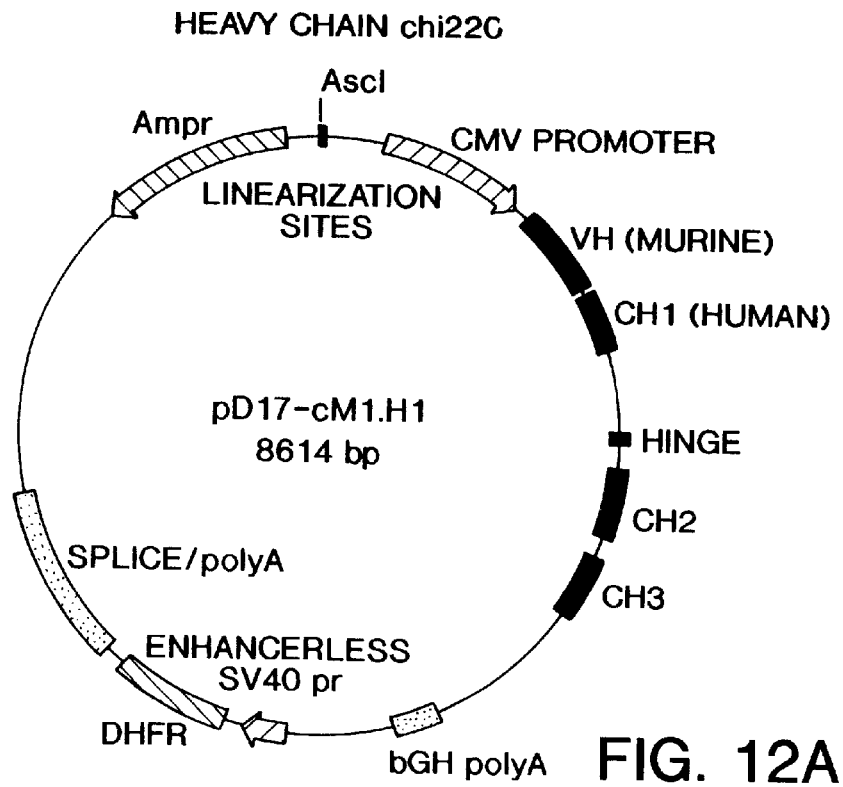
FIG. 12 shows expression vector maps for a heavy chain region and light chain region of a chimeric antibody of the present invention.
Figure 12B:
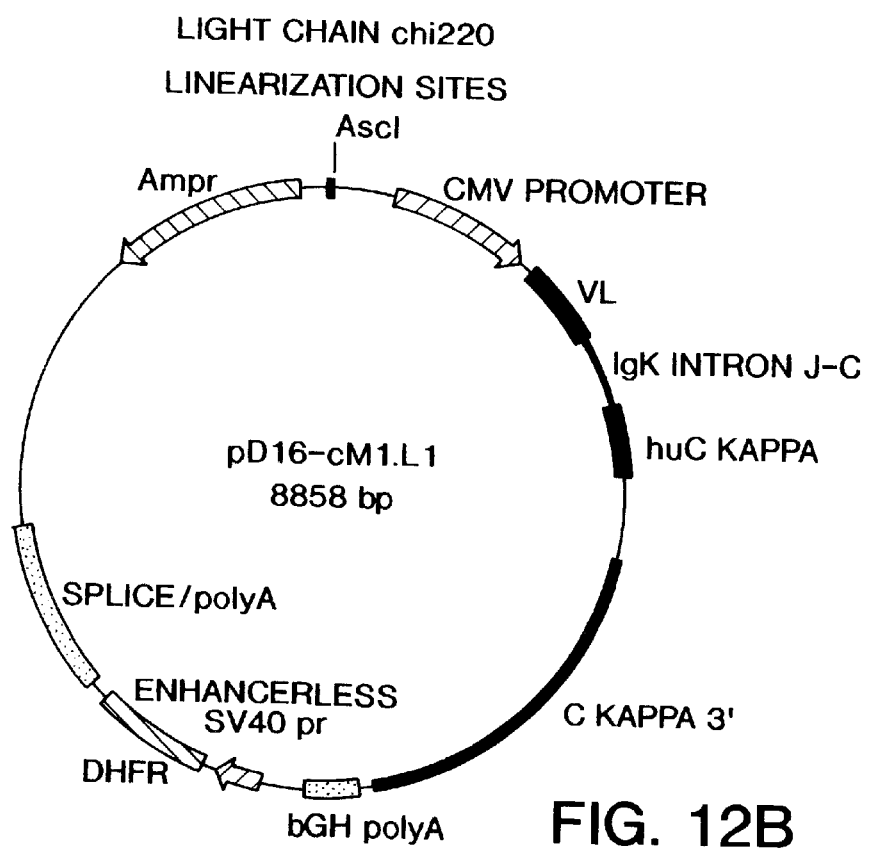

As an example, a chimeric antibody producing cell line was generated by co-transfecting CHO DG44 cells with separate expression vectors for the heavy and light chains of the chimeric antibody, and the high copy number electroporation method was used to promote co-integration. (See, U.S. Pat. No. 4,956,288). The chi220 heavy and light chains were cloned into the pD 17 and pD 16 expression vectors, respectively. Both vectors are derived from the InVitrogen™ plasmid pcDNA3, and contain the following features (FIG. 12): (1) the neomycin resistance gene from pcDNA3 was replaced with the murine dihydrofolate reductase (DHFR) gene under control of the enhancerless SV40 promoter (also referred to as the "weakened DHFR"; note that only the promoter was weakened, not the DHFR enzyme—the enhancerless promoter still contains the SV40 origin of replication, so these vectors can be used in transient COS transfections); (2) the gene of interest is expressed from the CMV promoter, and the poly adenylation signal is from the bovine growth hormone gene; (3) the expression cassette for the gene of interest is flanked by transcription termination sequences (i.e., 5' to the promoter and 3' to the poly A site); (4) the vectors contain two distinct restriction site polylinkers, one 3' to the promoter for cloning the gene of interest, and one 5' to the promoter for vector linearization prior to transfection; and (5) the ampicillin resistance gene and ColE1 origin for plasmid propagation in E. coli.

The heavy and light chain genes used were genomic constructs, with the following modifications: (1) the coding sequences for the heavy chain signal peptide, variable region and CH1 domain were contiguous (i.e., contained no introns); and (2) the coding sequences for the light chain signal peptide and variable region were contiguous.

Other expression vectors known by those skilled in the art, and capable of expressing a chimeric antibody of the present invention, are contemplated by the present invention. A nucleic acid sequence useful in an expression vector capable of expressing a heavy chain of a chimeric antibody of the present invention is shown in FIG. 13; a nucleic acid sequence useful in an expression vector capable of expressing a light chain of a chimeric antibody of the present invention is shown in FIG. 14.

Figure 5A:
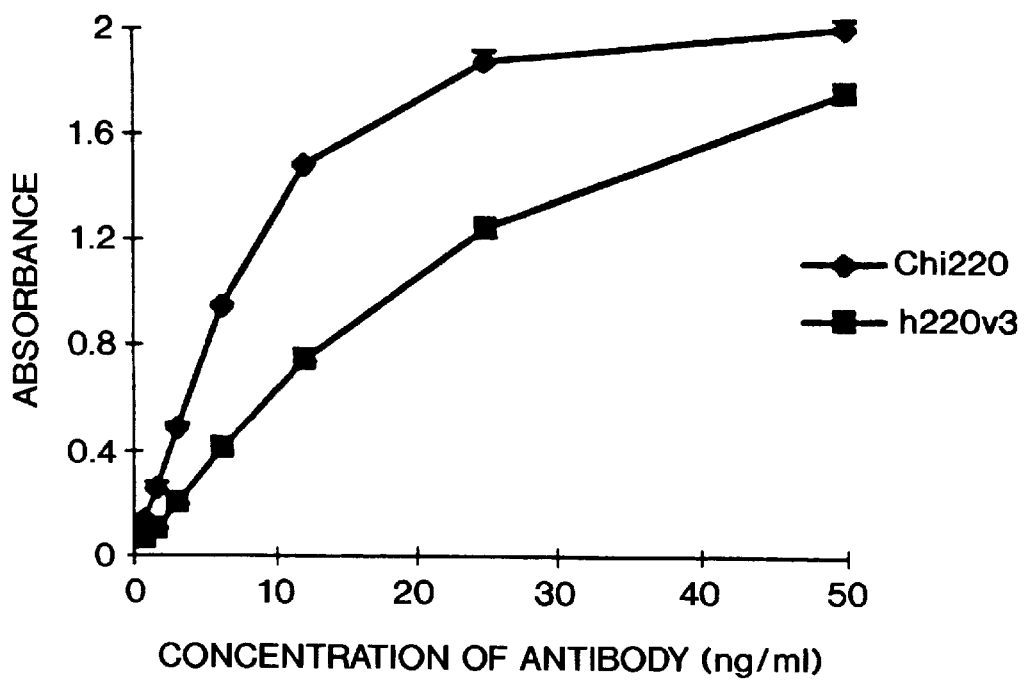
FIG. 5a shows the binding of chi220 and h220v3 to hCD40-mG2b in an ELISA based assay.

The complete amino acid sequence of the heavy and light chains of the chimeric antibody ("chi220"), including the variable and constant regions, is as follows (the bold amino acids indicate variable heavy and variable light):

sequence known or suspected to be important to the binding specificity are replaced in the human sequences for both VH and VL. The structures of these sequences were then modeled using as a template the protein with the closest homology for which a crystal structure has been solved. Plasmids encoding the humanized forms were generated using PCR directed mutagenesis and used to generate antibody by transient expression from COS cells. In vitro assays were performed with the chimeric and humanized antibodies of the present invention, and results are depicted in FIG. 5. FIG. 5a shows the results of a binding assay testing the binding of chi220 and h220v3 to hCD40-mG2b in an ELISA based assay. Wells of Immulon-2 plates Immunlon® II microtiter plates (Dynex) were coated with hCD40-mG2b at a concentration of 10 ng/ml in PBS for 2 hrs. Wells were blocked with Specimen Diluent (Genetic Systems), and antibodies were added at the indicated concentrations. Following a 1hr incubation, wells were washed, and the presence of the antibody detected using peroxidase-conjugated goat anti-human IgG antibody. H220v3 is a humanized form of mAb 2.220. Values are the average of duplicate wells and error bars represent the standard deviation.

Figure 5B:
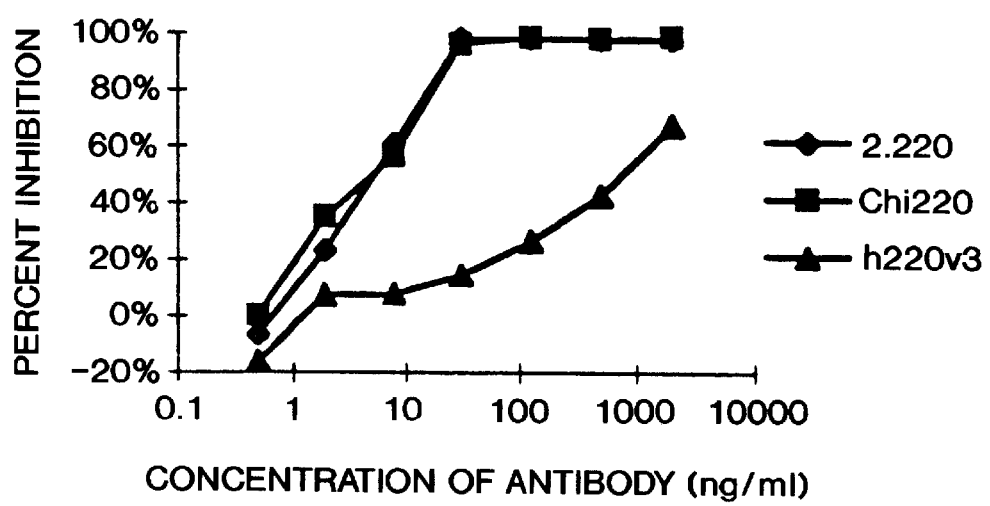
FIG. 5b shows the inhibition of sgp39mediated costimulation of human B cells with anti-human CD40 mAbs.

FIG. 5b shows the results of an assay testing the inhibition of sgp39-mediated costimulation of human B cells with anti-human CD40 mAbs. Resting human tonsillar B cells (50,000/well) were incubated with sgp39 fusion protein, 20 µg/ml rabbit anti-human IgM coated immununobeads and the indicated concentrations of the anti-CD40 mAbs or medium only control in 96 well plates. 72 hrs after initiation of cultures, all wells were pulsed with 1 uCi/well [$^3$H] thymidine and the cells cultured for an additional 18 hrs.

```
Heavy Chain Sequence (SEQ ID NO:3)
QIQLVQSGPE LKKPGETVRI SCKASGYAFT TTGMQWVQEM PGKGLKWIGW   50

INTHSGVPKY VEDFKGRFAF SLETSANTAY LQISNLKNED TATYFCVRSG  100

NGNYDLAYFA YWGQGTLVTV SAASTKGPSV FPLAPSSKST SGGTAALGCL  150

VKDYFPEPVT VSWNSGALTS GVHTFPAVLQ SSGLYSLSSV VTVPSSSLGT  200

QTYICNVNHK PSNTKVDKKV EPKSCDKTHT CPPCPAPELL GGPSVFLFPP  250

KPKDTLMISR TPEVTCVVVD VSHEDPEVKF NWYVDGVEVH NAKTKPREEQ  300

YNSTYRVVSV LTVLHQDWLN GKEYKCKVSN KALPAPIEKT ISKAKGQPRE  350

PQVYTLPPSR DELTKNQVSL TCLVKGFYPS DIAVEWESNG QPENNYKTTP  400

PVLDSDGSFF LYSKLTVDKS RWQQGNVFSC SVMHEALHNH YTQKSLSLSP  450

GK                                                     452

Light Chain Sequence (SEQ ID NO:4)
DIVLTQSPAT LSVTPGDRVS LSCRASQSIS DYLHWYQQKS HESPRLLIKY   50

ASHSISGIPS RFSGSGSGSD FTLSINSVEP EDVGIYYCQH GHSFPWTFGG  100

GTKLEIKRTV AAPSVFIFPP SDEQLKSGTA SVVCLLNNFY PREAKVQWKV  150

DNALQSGNSQ ESVTEQDSKD STYSLSSTLT LSKADYEKHK VYACEVTHQG  200

LSSPVTKSFN RGEC                                        214
```

Several humanized forms of 220 were generated. This process involves the identification of murine and human germline sequences with the closest homology to the VH and VL domains. The murine germline sequences were used to identify likely locations of somatic mutations that have arisen during the process of affinity maturation. The human sequences were then used as template and regions of the Cells were then harvested and incorporated [$^3$H]thymidine measured in a scintillation counter.

Based upon the results of in vitro assays (FIGS. 5a and 5b, that show both the chimeric and humanized antibody effectively bound CD40 and inhibited B cell stimulation) the chimeric antibody was chosen for further study.

EXAMPLE 3

Efficacy of chi220

A. Chimeric mAb 2.220: Single-Dose Efficacy Study in Nonhuman Primates

Chi220 was evaluated in cynomolgus monkeys for its ability to suppress primary and secondary humoral immune responses to T cell-dependent antigens. In one study, groups of four monkeys were immunized with sheep erythrocytes (SRBCs) and given a secondary immunization of ovalbumin (OVA) immediately prior to receiving a single intravenous bolus dose of either chi220 at 10, 40, or 100 mg/kg or sterile phosphate buffered saline (PBS) as a control. Substantial suppression of the primary humoral immune response against SRBCs was observed at all three dose levels, demonstrating efficacy of chi220 in primates. A dose-dependent transient depletion of peripheral blood B cells was observed in all of the chi220-treated monkeys, with the time to recovery also being dose dependent. At the two highest doses, transient mild decreases in the group mean absolute numbers of peripheral blood T cells were observed. Transient minimal decreases in serum IgM levels were observed, with no drug related changes in serum levels of IgG or IgA.

To assess the induction of immunological tolerance and reversibility of immunosuppressive activity, all monkeys were immunized with OVA, SRBCs, and a neoantigen, keyhole limpet hemocyanin (KLH) on day 149, when serum levels of chi220 in the 100 mg/kg group were below levels believed to be immunosuppressive (~10 $\mu$g/ml) and the numbers of peripheral blood B cells had returned to predose levels. The anti-SRBC response at the lowest dose level was generally comparable to the primary anti-SRBC antibody response in the control monkeys. However, the antibody response to SRBCs was still partially or substantially suppressed in the monkeys treated at the two higher dose levels.

To further explore the dose dependence of immunosuppression and B cell depletion, a second study was performed in which additional monkeys (four/group) were immunized with SRBCs, and then given a single dose of chi220 at 0.1 or 1.0 mg/kg or PBS. Suboptimal immunosuppression of the antibody response to SRBCs was observed at both dose levels. Moderate depletion of peripheral blood B cells was evident in monkeys that received 1.0 mg/kg chi220 by Day 8, reversing by Day 29. At 0.1 mg/kg, a decrease in the mean number and percentage of peripheral blood B cells was observed, but values were not outside the normal historical ranges for percent B cells. Historical limits have not been established for absolute numbers of peripheral blood B cells. Transient minimal decreases in peripheral blood T cell numbers and mild decreases in ex vivo T cell proliferation were observed in monkeys that received 1 mg/kg chi220. Finally, there was no evidence of complement activation or drug-related changes in the serum levels of IL-6 or TNF$\alpha$. Ex vivo T cell activation, complement activation, and serum cytokine levels were not assessed in monkeys treated with 10, 40, or 100 mg/kg chi220.

In both studies, serum samples were examined following chi220 administration for circulating levels of test article, and to assess antibody formation against the test article. Phannacokinetic analysis indicated that the mean peak serum concentration (Cmax) of chi220 did not increase in a manner proportional to the dose increment, and that the half-life of chi220 became prolonged as the dose administered was increased. Chi220 was found to be immunogenic when administered at 0.1, 1 or 10 mg/kg. At circulating concentrations above 10 $\mu$g/ml, it appears that chi220 can suppress the antibody response directed against it.

1. Experimental Protocol

In the initial study mentioned above, cynomolgus monkeys were assigned to four groups consisting of two males and two females each. All monkeys were immunized 28 days prior to chi220 or control article administration with OVA (5 mg/kg, im and 10 mg/kg, sc). On Day 1, all monkeys were immunized with SRBCs (1.7 ml/kg of a 10% suspension, iv) and given a secondary immunization of OVA (5 mg/kg, im and 10 mg/kg, sc) immediately prior to receiving a single intravenous bolus dose of either chi220 at 10, 40, or 100 mg/kg or sterile PBS as a control. On Day 149, after the serum levels of chi220 had fallen below putatively immunosuppressive levels (~10 $\mu$g/ml) and the levels of peripheral blood B cells had returned to predose levels in all groups, the monkeys were immunized with OVA, SRBCs, and KLH (10 mg/animal, im). The purpose of the KLH immunization was to show that the monkeys were able to mount an immune response to a neoantigen after being treated with chi220.

In order to demonstrate a better dose response with respect to imnunosuppression and peripheral blood B cell depletion, additional monkeys in a second study (two/sex/group) were immunized with SRBCs, and then given a single dose of either chi220 at 0.1 or 1.0 mg/kg or PBS as a control on Day 1. Hematological parameters and peripheral blood lymphocyte subpopulations were monitored at selected time points during both studies. Serum chemistry parameters were monitored in monkeys that received 10, 40, or 100 mg/kg chi220, but were not monitored at the 0.1 and 1 mg/kg dose levels because no drug-related findings were observed at the higher doses. In addition, serum levels of IgM, IgG, IgA, and chi220 were measured. To assess efficacy, specific IgM and IgG antibody formation against the SRBC and OVA immunogens was determined on the appropriate serum samples obtained just prior to immnunogen administration and weekly thereafter. Specific IgM and IgG antibody formation against the test article for monkeys that received chi220 was determined prior to test article administration on Day 1, and weekly thereafter. Geometric mean titers were used when comparing antibody responses between groups. In addition, total hemolytic complement activity ($CH_{50}$) and C4d fragment levels were measured, and TNF-$\alpha$ and IL-6 levels were determined in monkeys that received 0.1 or 1 mg/kg chi220 at selected time points following chi220 administration. Ex vivo peripheral blood T cell activation was also assessed following stimulation with concanavalin A in monkeys receiving 0.1 and 1 mg/kg chi220 on Days 17 and 31 to assess the effects of chi220 on T cell responsiveness to a mitogen. Finally, all monkeys were observed daily for clinical signs of toxicity, body weights recorded weekly, and food consumption monitored daily.

Monkeys were immunized with SRBC prior to receiving vehicle or 10, 40, or 100 mg/kg chi220 (FIG. 6a) or 0.1 or 1 mg/kg chi220 (FIG. 6b) on Day 1. Serum samples were analyzed for IgM anti-SRBC antibodies by ELISA. Data are expressed as the geometric mean anti-SRBC antibody endpoint titer (EPT) for each group (n=2 [100 mg/kg group beyond Day 15] or 4), where EPT is equivalent to the reciprocal of the greatest dilution of serum with an absorbance of greater than two times the mean plate background.

2. Results a. Anti-SRBC Antibody Response

Figure 7A:
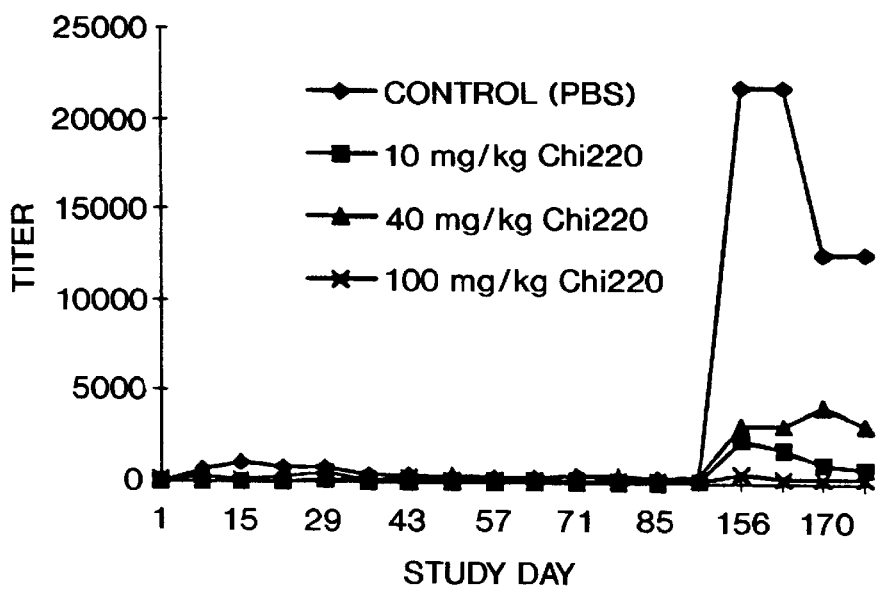
FIG. 7a shows the results from monkeys that received 10, 40 or 100 mg/kg chi220.

When administered to monkeys at 10, 40, or 100 mg/kg, chi220 was effective at substantially suppressing the primary antibody response against SRBCs. On the peak day of the control primary IgM anti-SRBC antibody response (Day 8), the mean primary IgM anti-SRBC antibody response was suppressed approximately 92–94% in the monkeys treated with 10, 40, and 100 mg/kg chi220, compared to controls (FIG. 6a). The group mean IgM anti-SRBC antibody response did not become positive through Day 85 at the 10, 40 or 100 mg/kg dose levels. On the peak day of the control primary IgG anti-SRBC antibody response (Day 15), the mean primary IgG anti-SRBC antibody response was suppressed 98%, 99%, and 85% in monkeys that received 10, 40, and 100 mg/kg, respectively, compared to controls (FIG. 7a). Higher overall predose anti-SRBC antibody titers in the 100 mg/kg group may have accounted for the apparent lack of dose-dependent immunosuppression. Overall, monkeys treated with 10 or 100 mg/kg chi220 did not mount a primary IgG anti-SRBC antibody response through Day 85. However, two of the monkeys treated with 40 mg/kg chi220 had a delayed primary IgG antibody response to SRBCs (comparable to the control response in magnitude), which became positive by Day 36 and peaked on Day 51.

On Day 149, after the serum levels of chi220 had fallen below putatively immunosuppressive levels (~10 $\mu$g/ml) and the levels of peripheral blood B cells had returned to predose levels in all groups, the monkeys were immunized a second time with SRBCs. As expected, control monkeys mounted a strong secondary IgG antibody response to SRBCs. Monkeys treated with 10 mg/kg chi220 mounted primary IgM and IgG antibody responses to SRBCs that were generally comparable to the primary antibody response in the control monkeys. However, the antibody response to SRBCs was still partially suppressed at the 40 mg/kg dose level and substantially suppressed at the 100 mg/kg dose level. Although two monkeys treated with 40 mg/kg chi220 that had previously mounted weak primary antibody responses to SRBCs developed IgM and IgG anti-SRBC antibody titers characteristic of a secondary antibody response, the anti-SRBC antibody responses in the two other monkeys in that group and the remaining monkeys treated with 100 mg/kg chi220 was still approximately 90% suppressed compared to the mean primary anti-SRBC antibody response of the control monkeys.

Figure 7B:
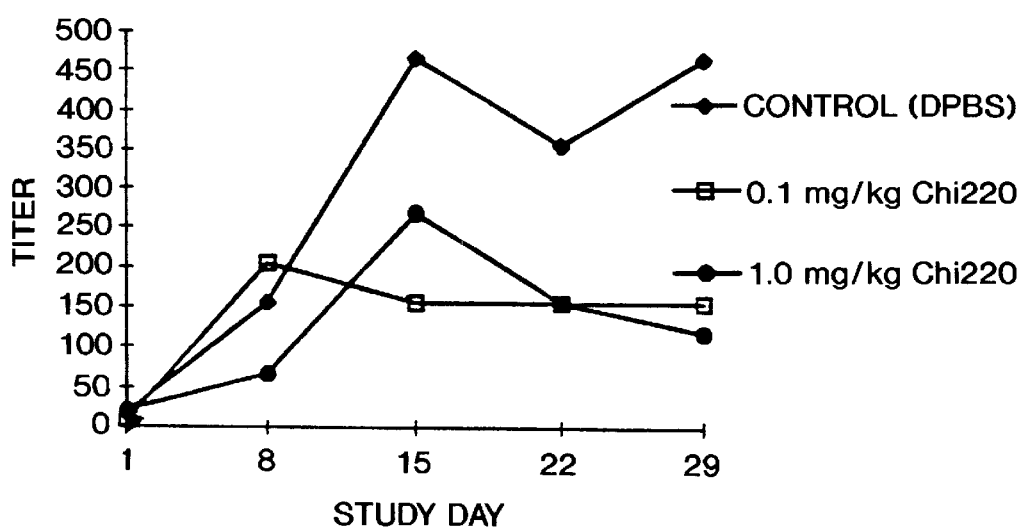
FIG. 7b shows the results from monkeys that received 0.1 or 1 mg/kg chi220.

Suboptimal immunosuppression of the antibody response to SRBCs was observed following administration of 0.1 or 1.0 mg/kg chi220 (FIGS. 6b and 7b). While all of the chi220-treated monkeys mounted a positive IgM antibody response to the SRBC antigen, the overall mean peak IgM anti-SRBC antibody response was suppressed approximately 56% in the monkeys treated with 1 mg/kg chi220 compared to the mean peak control response. No suppression of the IgM anti-SRBC antibody response was observed in monkeys treated with 0.1 mg/kg chi220. The mean IgM anti-SRBC antibody response peaked on Day 15 in the control monkeys, and on Day 8 in the monkeys that received 0.1 and 1.0 mg/kg chi220. Overall, the mean peak IgG anti-SRBC antibody response was suppressed 56% and 42% in the monkeys treated with 0.1 and 1.0 mg/kg chi220, respectively. The mean IgG anti-SRBC antibody response peaked on Day 15 in the control monkeys and monkeys treated with 1 mg/kg chi220, and on Day 8 in the monkeys that received 0.1 mg/kg chi220.

b. Anti-OVA Antibody Response

Figure 8A:
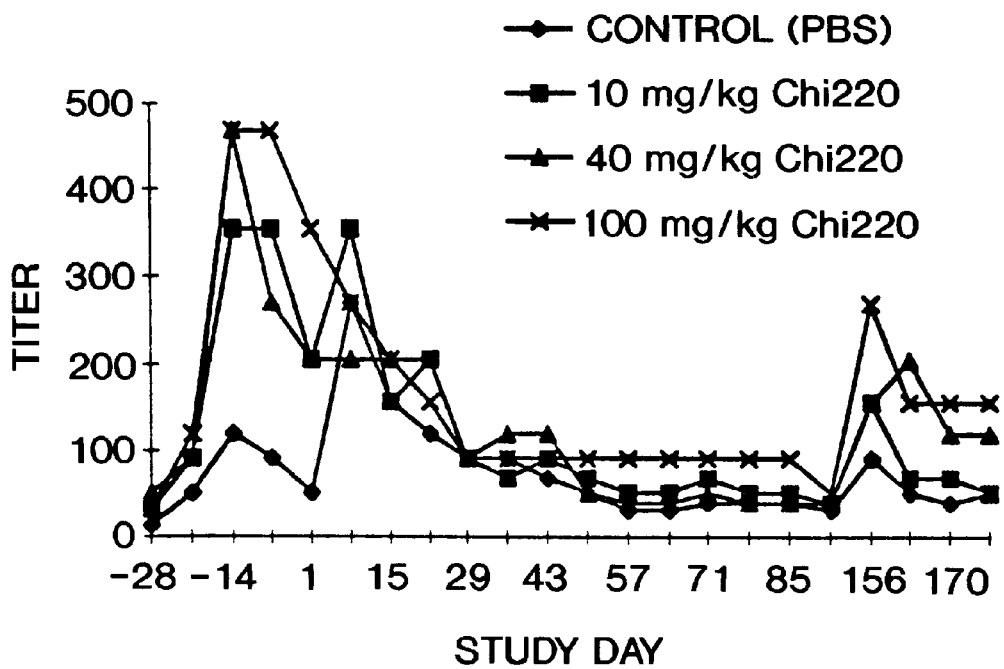
FIG. 8a shows the results of analysis for IgM anti-OVA antibodies.
Figure 8B:
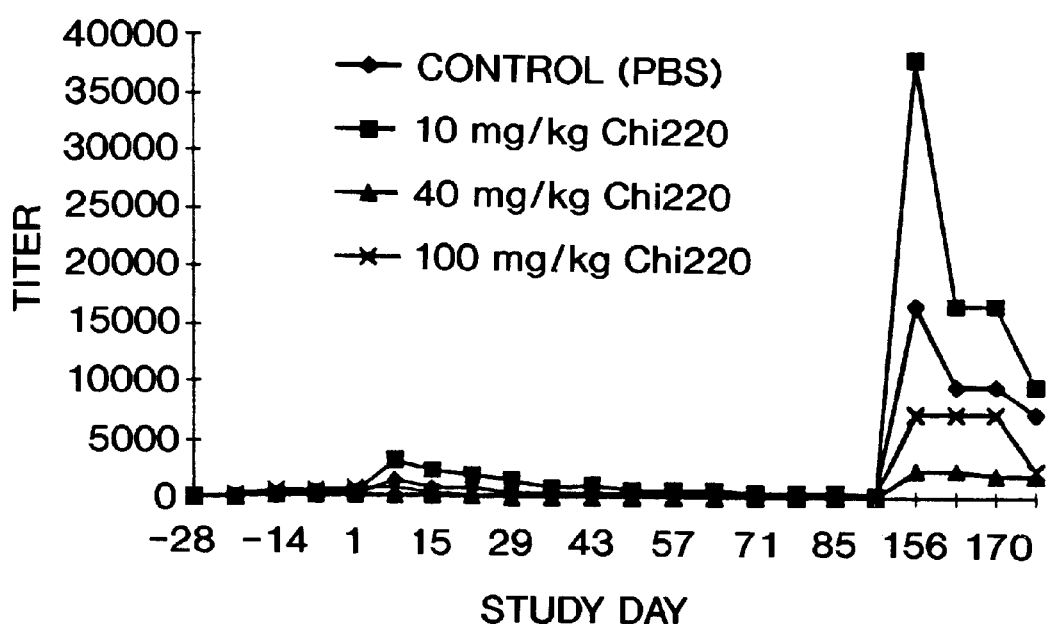
FIG. 8b shows the results of analysis for IgG anti-OVA antibodies.

Monkeys were administered an intravenous dose of 10, 40, or 100 mg/kg chi220 on Day 1. In addition all monkeys were immunized with OVA on Days -28, 1, and 149. Serum samples were analyzed for IgM (FIG. 8a) or IgG (FIG. 8b) anti-OVA antibodies. Data are expressed as the geometric mean anti-OVA endpoint titer (EPT) for each group (n=2 [100 mg/kg group beyond Day 15] or 4), where EPTs are equivalent to the reciprocal of the greatest dilution of serum with an absorbance of greater than two times the mean plate background.

Specific IgM and IgG antibody formation against OVA was monitored weekly during the study in monkeys that received 10, 40, or 100 mg/kg chi220. The primary and secondary anti-OVA antibody responses were highly variable and generally weak in all monkeys (FIG. 8). Monkeys scheduled to receive chi220 on Day I had greater anti-OVA antibody titers than monkeys in the control group.

On Day 149, the monkeys were given a tertiary OVA immunization. All of the monkeys mounted positive IgG antibody responses to OVA within 7 days following challenge. Control monkeys and monkeys treated with 10 mg/kg chi220 had antibody titers characteristic of a tertiary antibody response, whereas monkeys treated with either 40 or 100 mg/kg chi220 developed antibody titers that were more characteristic of a secondary antibody response.

C. Anti-KLH Antibody Response

Figure 9A:
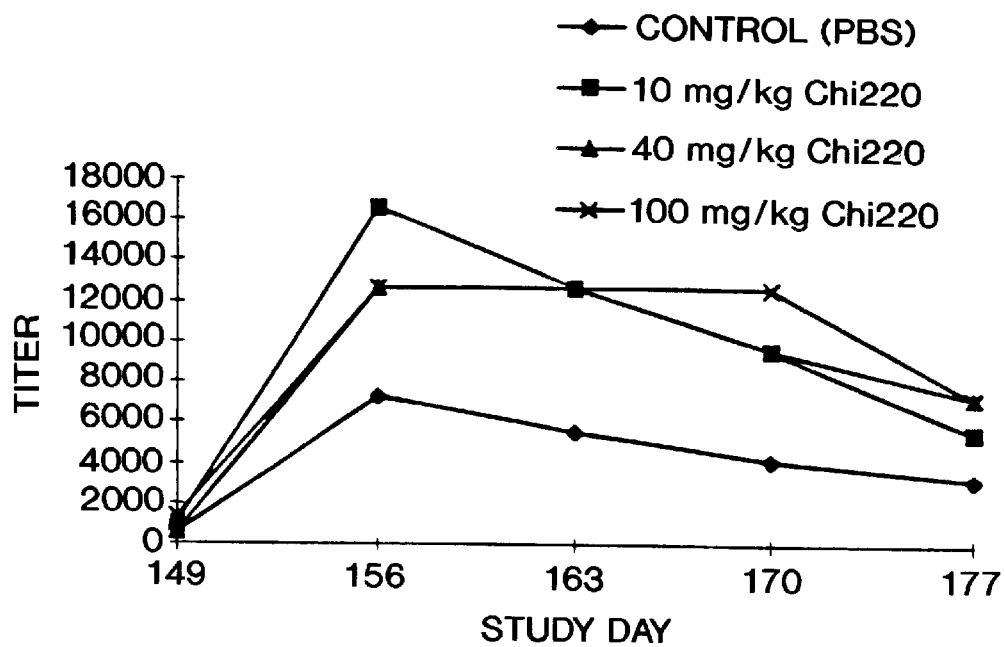
FIG. 9a shows the results of analysis for IgM anti-KLH antibodies.
Figure 9B:
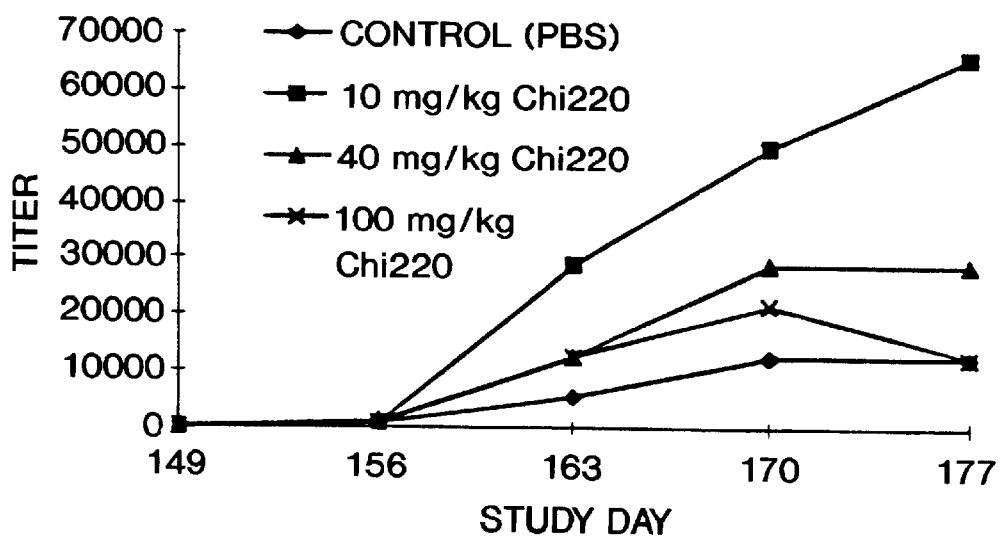
FIG. 9b shows the results of analysis for IgG anti-KLH antibodies.

Monkeys were administered an intravenous dose of 10, 40, or 100 mg/kg chi220 on Day 1. In addition, all monkeys were immunized with KLH on Day 149. Serum samples were analyzed for IgM (FIG. 9a) or IgG (FIG. 9b) anti-KLH antibodies. Data are expressed as the geometric mean anti-KLH endpoint titer (EPT) for each group (n=2 [100 mg/kg group beyond Day 15] or 4), where EPTs are equivalent to the reciprocal of the greatest dilution of serum with an absorbance of greater than two times the mean plate background.

On Day 149, after the serum levels of chi220 had fallen below putatively immunosuppressive levels (~10 $\mu$g/ml) and the levels of peripheral blood B cells had returned to predose levels in all groups, the monkeys were immunized with KLH (10 mg/animal, im). All monkeys mounted positive IgM and IgG antibody responses to KLH, demonstrating that the ability to respond to a new antigen was not compromised (FIG. 9).

d. Serum Levels of Test Article and Anti-Test Article Antibody Response

Serum samples were examined following chi220 administration to determine circulating levels of test article and to assess antibody formation against the test article. The mean peak serum concentration (Cmax) of chi220 occurred three minutes following the administration of 10 or 40 mg/kg doses and six hours following administration of the 100 mg/kg dose. Cmax values of chi220 were 329, 2429, and 2343 $\mu$g/ml in the monkeys treated with 10, 40, or 100 mg/kg chi220, respectively. There was, however, considerable variation in the Cmax of individual monkeys in the 40 and 100 mg/kg groups. The mean serum half-life of chi220 was estimated to be approximately 114, 173 and 315 hours in monkeys treated with 10, 40, or 100 mg/kg chi220, respectively.

Mean Cmax values, occurring three minutes following chi220 administration, were 1.77 and 33 $\mu$g/ml for 0.1 and 1 mg/kg doses, respectively. No gender related differences in the serum levels of chi220 were observed within each dose level. Mean $AUC_{inf}$ values were 15.5 and 847 ug.h/ml, for 0.1 and 1 mg/kg doses, respectively. Taken together, the studies suggest that the half-life of chi220 becomes prolonged as the dose administered is increased. Furthermore, it appears that the Cmax of chi220 increases in a manner disproportionate to the dose increment.

Although the IgM anti-test article response was minimal or absent in the monkeys that received 10, 40, or 100 mg/kg chi220, a significant IgG anti-test article antibody response was observed in the monkeys that received 10 mg/kg chi220. The mean IgG anti-test article antibody response in the monkeys that received 10 mg/kg chi220 became positive on Day 29, approximately 1 week after the mean group serum concentration of chi220 had fallen below 10 µg/ml, and peaked on Days 36 and 43 at a geometric mean titer of 12,627. The appearance of IgG anti-test article antibodies in the monkeys that were treated with 10 mg/kg chi220 also coincided with the first detectable increases in B cell numbers following depletion. By the last day measured (Day 149), the monkeys that received 40 or 100 mg/kg chi220 had still not mounted a positive antibody response against chi220, although the group mean chi220 serum levels were below 10 µg/ml by Day 57 (40 mg/kg group) or Day 92 (100 mg/kg group).

Chi220 was immunogenic when administered at 0.1 or 1 mg/kg. Three of four monkeys that received either 0.1 or 1 mg/kg chi220 had weakly positive IgM anti-test article antibody responses by Day 15 during the study. Three of four monkeys treated with 1 mg/kg chi220 had significant IgG anti-test article antibody responses by Day 22, peaking at a geometric mean endpoint titer of 16,618. Overall, the geometric mean IgG anti-test article antibody response was not positive in the monkeys that received 0.1 mg/kg chi220, and only one monkey that received 0.1 mg/kg chi220 had a weakly positive IgG anti-test article antibody response, peaking at an endpoint titer of 2430 on Day 22. Collectively, these data suggest that chi220 is capable of immunosuppressing an antibody response against itself at serum levels of greater than approximately 10 µg/ml.

EXAMPLE 4

Generation of Humanized Anti-CD40 Antibodies F4 and L3.17

A variety of methods known in the art have been used for the humanization of mAbs. Structure-based approaches have proven useful but the complexity that arises from the large number of framework residues potentially involved in binding activity diminishes the rate of success. Rather than predicting the optimal framework based on modeling, the antibody library approach described below permits identification of active framework conformations based on screening numerous combinations. Mutagenesis approaches coupled to selection methods permit the analysis of many variants and mimics the in vivo maturation process (reviewed in Marks, J. D., et al., (1992) *J. Biol. Chem.* 267:16007–16010). Codon-based mutagenesis permits the construction of libraries that characterize the contribution of specific residues and thus, is more efficient than random mutagenesis approaches. For example, error-prone PCR can not be used to synthesize the combinatorial framework libraries described below. Moreover, random mutagenesis creates larger more diverse libraries and unfortunately, the majority of mutations do not enhance the binding activity of the mAb. Consequently, larger numbers of clones must be screened to identify active variants.

A strategy termed "guided selection" has been used to isolate human mAbs from a phage display library in a two-step process that uses a rodent mAb as a template (Jespers, L. S., et al., (1994) *Bio/lTechnology* 12:899–903). Recently, a variation of guided selection using phage display technologies was described in which a chimeric Fd fragment was used to select a L chain from a library containing human L chains with grafted murine CDR3 (Rader, C., et al., (1998) *Proc. Natl. Acad. Sci. USA* 95:8910–8915). Subsequently, the most active L chain was used to select an H chain from a human H chain library containing the murine HCDR3. The mAbs isolated by these approaches are entirely human (Jespers, supra) or mostly human (Rader, supra), but the large antibody diversity introduced at each step of the processes necessitates the use of affinity enrichment methods.

The following materials and methods were utilized to generate the humanized anti-CD40 antibodies F4 and L3.17 of the present invention.

1. Construction of Chimeric anti-CD40

Based on the sequence of anti-CD40 murine mAb 2.220 overlapping oligonucleotides encoding $V_H$ and $V_L$ (69–75 bases in length) were synthesized and purified. The variable H and L domains were synthesized separately by combining 25 pmol of each of the overlapping oligonucleotides with Pfu DNA polymerase (Stratagene) in a 50 µl PCR reaction consisting of 5 cycles of: denaturing at 94° C. for 20 sec, annealing at 50° C. for 30 sec, ramping to 72° C. over 1 min, and maintaining at 72° C. for 30 sec. Subsequently, the annealing temperature was increased to 55° C. for 25 cycles. A reverse primer and a biotinylated forward primer were used to further amplify 1 µl of the fusion product in a 100 µl PCR reaction using the same program. The products were purified by agarose gel electrophoresis, electroeluted, and phosphorylated by T4 polynucleotide kinase (Boehringer Mannheim) and were then incubated with streptavidin magnetic beads (Boehringer Mannheim) in 5 mM Tris-C1, pH 7.5, 0.5 mM EDTA, 1 M NaCl, and 0.05% Tween 20 for 15 min at 25° C. The beads were washed and the non-biotinylated, minus strand DNA was eluted by incubating with 0.15 M NaOH at 25° C. for 10 min. Chimeric anti-CD40 Fab was synthesized in a modified M13IX104 vector (Kristensson, K., et al., (1995) *Vaccines* 95, pp. 39–43, Cold Spring Harbor Laboratory, Cold Spring Harbor, N.Y.), termed M13IX104CS, by hybridization mutagenesis (Rosok, M. J., et al., (1996) *J. Biol. Chem.* 271:22611–22618; Kunkel, T. A. (1985) *Proc. Natl. Acad. Sci. USA* 82:488–492) using the $V_H$ and $V_L$ oligonucleotides in 3-fold molar excess of the uridinylated vector template. The M13IX104 vector was modified by replacing cysteine residues at the end of the kappa and γ1 constant regions with serine. The reaction was electroporated into DH10B cells and titered onto a lawn of XL-1 Blue.

2. Construction of Combinatorial Framework and Framework/CDR3 Libraries.

The combinatorial framework library (Hu I) was synthesized by the same method used to construct the chimeric anti-CD40, with modifications. Overlapping oligonucleotides encoding the framework regions of the H and L variable domains of the human template and the murine anti-CD40 CDRs as defined by Kabat et aL (Kabat, E. A., et al., (1991) Sequences of proteins of immunological interest (5th Ed), Washington DC: United States Department of Health and Human Services; Kabat, E. A., et al., (1977) *J. Biol. Chem.* 252:6609–6616) were synthesized. Degenerate oligonucleotides encoding both the murine and the human amino acids at seven $V_H$ and one $V_K$ framework position were synthesized (FIG. 15, residues marked with asterisk).

The framework/HCDR3 (Hu II) and framework/HCDR3/LCDR3 (Hu III) libraries were synthesized by the same method as the combinatorial framework library, with modifications. The CDR residues selected for mutagenesis were: $Ser^{95}$-$Tyr^{102}$ in HCDR3 and $Gln^{89}$-$Thr^{97}$ in LCDR3 (FIG. 15, underlined). Oligonucleotides encoding HCDR3 and LCDR3 were designed to mutate a single CDR residue and were synthesized by introducing NN(G/T) at each position as described in the art (Glaser, S. M., et al., (1992) *J. Immunol.* 149:3903–3913). The overlapping oligonucleotides encoding the framework library and non-library murine CDRs were combined with 25 pmol of the oligonucleotides encoding mutated HCDR3 or with 25 pmol each of the oligonucleotides encoding mutated HCDR3 and LCDR3.

3. Screening of Phage Expression Libraries

The Hu II and Hu III libraries were initially screened by a modified plaque lift approach known in the art, termed capture lifi (Watkins, J. D., et al., (1998) *Anal. Biochem.* 256:169–177). Briefly, nitrocellulose filters (82-mm) were coated with goat anti-human kappa, blocked with 1 % BSA, and were applied to an agar plate containing the phage-infected bacterial lawn. In the initial screen, phage were plated at $10^5$ phage/100-mm plate. After the capture of phage-expressed anti-CD40 variant Fabs, the filters were incubated 3 h at 25° C. with 5 ng/ml CD40-Ig in PBS containing 1% BSA. The filters were rinsed four times with PBS containing 0.1% Tween 20 and were incubated with goat anti-mouse $IgG_{2b}$-alkaline phosphatase conjugate (Southern Biotechnology) diluted 3000-fold in PBS containing 1% BSA for 1 h at 25° C. The filters were washed four times with PBS containing 0.1% Tween 20 and were developed as described (Watkins (1998), supra). To isolate individual clones, positive plaques from the initial screen were picked, replated at lower density ($<10^3$ phage/100-mm plate), and were screened by the same approach.

The Hu I combinatorial library was first screened by an ELISA that permits the rapid assessment of the relative affinities of the variants (Watkins, J. D., et al., (1997) *Anal. Biochem.* 253:37–45). In addition, the ELISA was used to characterize clones identified by capture lift screening. Briefly, microtiter plates were coated with 5 μg/ml goat anti-human kappa (Southern Biotechnology) and blocked with 3% BSA in PBS. Next, 50 μl Fab from the *Escherichia coli* culture supernatant or from the cell lysate, was incubated with the plate 1 h at 25° C., the plate was washed three times with PBS containing 0.1% Tween 20, and 0.1 μg/ml CD40-Ig in PBS containing 1% BSA for 2 h at 25° C. The plate was washed three times with PBS containing 0.1% Tween 20 and goat anti-mouse $IgG_{2b}$-alkaline phosphatase conjugate diluted 3000-fold in PBS containing 1% BSA was added for 1 h at 25° C. The plate was washed three times with PBS containing 0.1% Tween 20 and was developed as described in the art (Watkins (1997), supra).

4. DNA Sequencing

Single-stranded DNA was isolated and the H and L chain variable region genes of the humanized antibodies of the present invention were sequenced by the fluorescent dideoxynucleotide termination method (Perkin-Elmer, Foster City, Calif.).

The nucleic acid (SEQ ID NO:7) and amino acid (SEQ ID NO:8) sequence of the variable light chain of humanized antibody F4 is as follows:

```
GAA ATT GTG TTG ACA CAG TCT CCA GCC ACC CTG TCT TTG TCT    42
 E   I   V   L   T   Q   S   P   A   T   L   S   L   S     14

CAA GGG GAA AGA GCC ACC CTC TCC TGC AGG GCC AGT CAG AGT    84
 P   G   E   R   A   T   L   S   C   R   A   S   Q   S     28

ATT AGC GAT TAC TTA CAT TGG TAC CAA CAG AAA CCT GGC CAG   126
 I   S   D   Y   L   H   W   Y   Q   Q   K   P   G   Q     42

GCT CCC AGG CTC CTC ATC TAT TAC GCA TCC CAC TCC ATC TCT   168
 A   P   R   L   L   I   Y   Y   A   S   H   S   I   S     56

GGC ATC CCA GCC AGG TTC AGT GGC AGT GGG TCT GGG ACA GAC   210
 G   I   P   A   R   F   S   G   S   G   S   G   T   D     70

TTC ACT CTC ACC ATC AGC AGC CTA GAG CCT GAA GAT TTT GCA   252
 F   T   L   T   I   S   S   L   E   P   E   D   F   A     84

GTT TAT TAC TGT CAG CAT GGC CAC TCT TTT CCT TGG ACC TTC   294
 V   Y   Y   C   Q   H   G   H   S   F   P   W   T   F     98

GGA GGG GGG ACC AAG GTG GAA ATT AAA                       321
 G   G   G   T   K   V   E   I   K                        107
```

The nucleic acid (SEQ ID NO:9) and amino acid (SEQ ID NO: 10) sequence of the variable heavy chain of humanized antibodies F4 and L3.17 is as follows:

```
CAG GTG CAG CTG GTG CAA TCT GGG TCT GAG TTG AAG AAG CCT    42
 Q   V   Q   L   V   Q   S   G   S   E   L   K   K   P     14

GGG GCC TCA GTG AAG GTT TCC TGC AAG GCT TCT GGA TAC GCC    84
 G   A   S   V   K   V   S   C   K   A   S   G   Y   A     28

TTC ACT ACC ACT GGC ATG CAG TGG GTG CGA CAG GCC CCT GGA   126
 F   T   T   T   G   M   Q   W   V   R   Q   A   P   G     42

CAA GGG CTT GAG TGG ATG GGA TGG ATC AAC ACC CAC AGC GGG   168
 Q   G   L   E   W   M   G   W   I   N   T   H   S   G     56

GTC CCA AAG TAT GTC GAG GAC TTC AAA GGA CGG TTT GTC TTC   210
 V   P   K   Y   V   E   D   F   K   G   R   F   V   F     70

TCC TTG GAC ACC TCT GTC AGC ACG GCA TAT CTG CAG ATC AGC   252
 S   L   D   T   S   V   S   T   A   Y   L   Q   I   S     84
```

-continued

```
AGC CTA AAG GCT GAG GAC ACT GCC GTG TAT TAC TGT GCG AGA   294
 S   L   K   A   E   D   T   A   V   Y   Y   C   A   R    98

TCT GGC AAT GGG AAC TAT GAC CTG GCA TAC TTT AAG TAT TGG   336
 S   G   N   G   N   Y   D   L   A   Y   F   K   Y   W   112

GGC CAG GGA ACC CTG GTC ACC GTC TCC TCA                   366
 G   Q   G   T   L   V   T   V   S   S                   122
```

The nucleic acid (SEQ ID NO: 11) and amino acid (SEQ ID NO:12) sequence of the variable light chain of humanized antibody L3.17 is as follows:

```
GAA ATT GTG TTG ACA CAG TCT CCA GCC ACC CTG TCT TTG TCT    42
 E   I   V   L   T   Q   S   P   A   T   L   S   L   S    14

CCA GGG GAA AGA GCC ACC CTC TCC TGC AGG GCC AGT CAG AGT    84
 P   G   E   R   A   T   L   S   C   R   A   S   Q   S    28

ATT AGC GAT TAC TTA CAT TGG TAC CAA CAG AAA CCT GGC CAG   126
 I   S   D   Y   L   H   W   Y   Q   Q   K   P   G   Q    42

GCT CCC AGG CTC CTC ATC TAT TAC GCA TCC CAC TCC ATC TCT   168
 A   P   R   L   L   I   Y   Y   A   S   H   S   I   S    56

GGC ATC CCA GCC AGG TTC AGT GGC AGT GGG TCT GGG ACA GAC   210
 G   I   P   A   R   F   S   G   S   G   S   G   T   D    70

TTC ACT CTC ACC ACT AGC AGC CTA GAG CCT GAA GAT TTT GCA   252
 F   T   L   T   I   S   S   L   E   P   E   D   F   A    84

GTT TAT TAC TGT CAG CAT GGC CAC TCT TAT CCT TGG ACC TTC   294
 V   Y   Y   C   Q   H   G   H   S   Y   P   W   T   F    98

GGA GGG GGG ACC AAG GTG GAA ATT AAA                       321
 G   G   G   T   K   V   E   I   K                       107
```

5. Expression and Purification of Fab

Certain Fabs were cloned into an expression vector under the control of the arabinose-regulated BAD promoter. In addition, a six-histidine tag was fused to the carboxyl-terminus of the H chain to permit purification with nickel-chelating resins. Purified Fab was quantitated as described (Watkins (1997), supra). 6. Characterization Assays Immulon®II microtiter plates were coated with 0.1 μg/ml CD40-Ig in PBS for 16 h at 4° C. and were blocked with 3% BSA in PBS. The plates were washed three times in PBS containing 0.1% Tween 20 and Fab released from periplasmic space was diluted serially three-fold in PBS containing 1% BSA and incubated with the plate 2 h at 25° C. Subsequently, the plate was washed four times with PBS containing 0.1% Tween 20 and binding of antibody was detected by incubating with goat anti-human kappa-alkaline phosphatase conjugate diluted 2000-fold in PBS containing 1% BSA for 1 h at 25° C. The plate was washed four times with PBS containing 0.1% Tween 20 and was developed colorimetrically (Watkins (1997), supra).

To test the variants for inhibition of ligand binding, Immulon II microtiter plates were coated with 2 μg/ml anti-murine CD8 to capture sgp39 fuision protein which expresses the CD8 domain. The plates were rinsed once with PBS containing 0.05% Tween 20, and were blocked with 3% BSA in PBS. The plate was washed once with PBS containing 0.05% Tween 20 and was incubated with cell culture media containing saturating levels of sgp39 for 2 h at 25° C. Unbound sgp39 was aspirated and the plate was washed two times with PBS containing 0.05% Tween 20. Next, 25 μl of purified variant Fabs diluted serially 3-fold in PBS was added followed by 25 μl of 4 μg/ml CD40-human Ig in PBS. The plates were incubated 2 h at 25° C. and were washed three times with PBS containing 0.05% Tween 20. Bound CD40-Ig was detected following a 1 h incubation at 25° C. with goat F(ab')2 anti-human IgG Fcγ-specific horseradish peroxidase conjugate (Jackson) diluted 10,000-fold in PBS. The plate was washed four times with PBS containing 0.05% Tween 20 and binding was quantitated calorimetrically by incubating with 1 mg/ml o-phenylenediamine dihydrochloride and 0.003% hydrogen peroxide in 50 mM citric acid, 100 mM $Na_2HPO_4$, pH 5. The reaction was terminated by the addition of $H_2SO_4$ to a final concentration of 0.36 M and the absorbance at 490 nm was determined.

7. BIAcore Analysis

The kinetic constants for the interaction between CD40 and the anti-CD40 variants were determined by surface plasmon resonance (BIAcore). CD40-Ig fusion protein was immobilized to a (1-ethyl-3-[3-dimethylaminopropyl]-carbodiimide hydrochloride) and N-hydroxysuccinimide-activated sensor chip CM5 by injecting 8 μl of 10 μg/ml CD40-Ig in 10 mM sodium acetate, pH 4. CD40-Ig was immobilized at a low density (~150 RU) to prevent rebinding of Fabs during the dissociation phase. To obtain association rate constants ($k_{on}$), the binding rate at six different Fab concentrations ranging from 25–600 nM in PBS was determined at a flow rate of 20 μl/min. Dissociation rate constants ($k_{off}$) were the average of six measurements obtained by analyzing the dissociation phase. Sensorgrams were analyzed with the BIAevaluation 3.0 software program (BIAcore). $K_d$ was calculated from $K_d=k_{off}/k_{on}$. Residual Fab was removed after each measurement by prolonged dissociation.

The results of kinetics analysis for the humanized antibodies F4 and L3.17 compared to a chimeric Fab are shown in Table 1 below:

TABLE 1

| Clone ID# | $k_{on}$ | $K_{off}$ | $K_d$ | Comment |
|---|---|---|---|---|
| Chimeric Fab | 8.43E+5 | 2.65E−3 | 3.14 nM | Prepared by papain cleavage of chimeric 2.220 IgG |
| F4 | 2.00E+6 | 4.77E−4 | 0.24 nM | Humanized |
| L3.17 | 3.17E+6 | 3.28E−4 | 0.10 nM | Humanized |

8. Humanization Results

As discussed above, the murine anti-CD40 mAb variable region framework sequences were used to identify the most homologous human germline sequences. The H chain framework residues were 74% identical to human germline VH7 (7–4.1) and JH4 sequences while the L chain was 75% identical to the corresponding human germline VKIII (L6) and JK4 sequences. Alignment of the H and L chain variable sequences is shown in FIG. 15. CDR residues, as defined by Kabat et al. (Kabat, E. A., et al., (1991) Sequences of proteins of immunological interest (5th Ed), Washington DC: United States Department of Health and Human Services; Kabat, E. A., et al., (1977) J. Biol. Chem. 252:6609–6616) are underlined and were excluded from the homology analysis. Framework residues that differed between the murine mAb and the human templates were assessed individually.

Based on structural and sequence analysis, antibody CDRs with the exception of HCDR3 display a limited number of main chain conformations termed canonical structures (Chothia, C. et al., (1987) J. Mol. Biol. 196:901–917; Chothia, C., et al., (1989) Nature 342:877–883). Moreover, certain residues critical for determining the main chain conformation of the CDR loops have been identified (Chothia (1987), supra; Chothia (1989), supra). Canonical framework residues of murine anti-CD40 were identified therefore, and it was determined that amino acids at all critical canonical positions within the H and L chain frameworks of the human templates were identical to the corresponding murine residues.

Surface-exposed murine amino acids not normally found in human antibodies are likely to contribute to the immunogenicity of the humanized mAb (Padlan, E. A. (1991) Mol. Immunol. 28:489–498). Therefore, framework residues differing between murine anti-CD40 and the human templates were analyzed and based on solvent exposure were predicted to be buried or located on the surface of the antibody (Padlan (1991), supra). Solvent-exposed framework residues distal to the CDRs were not expected to contribute to antigen binding significantly and thus, with the exception of two H chain residues all were changed to the corresponding human amino acid to decrease potential immunogenicity. H chain residues 28 and 46 were predicted to be solvent exposed. However, H28 is located within the HCDR1 region as defined by Chothia et al., supra, and potentially interacts with the antigen. In addition, the lysine at H46 in the murine mAb is somewhat unusual and significantly different from the glutamic acid of the human template. Therefore, the murine and human residues at H28 and H46 were expressed in the combinatorial library (FIG. 15, asterisks).

The remaining differing framework residues, all predicted to be mostly buried within the antibody, were evaluated for: (1) proximity to CDRs; (2) potential to contact the opposite domain in the $V_K$-$V_H$ interface; (3) relatedness of the differing amino acids; and (4) predicted importance in modulating CDR activity as defined by Studnicka et al. (Studnicka, G. M., et al. (1994) Protein Eng. 7:805–814). The majority of L chain framework differences in buried residues were related amino acids at positions considered not likely to be directly involved in the conformation of the CDR. However, L49 is located adjacent to LCDR2, potentially contacts the $V_H$ domain, is unrelated to the human residue, and may be involved in determining the conformation of LCDR2. For these reasons, the murine and human amino acids at L49 were both expressed in the combinatorial framework library (FIG. 15, asterisk).

Analysis of the murine H chain sequence and the human template was more complex. Residue H9 is a proline in the murine mAb while the human template contains an unrelated serine residue. Position H9 may also play a role in modulating the conformation of the CDR and thus, was selected as a combinatorial library site (FIG. 15, asterisks). The remaining buried framework residues that differed between murine anti-CD40 and the H chain template were at framework positions 38, 39, 48, and 91. Murine anti-CD40 mAb contained glutamine and glutamic acid at H38 and H39, respectively, while the human template contained arginine and glutamine. Residue H38 is in proximity to the HCDR1, the glutamine→arginine change is non-conserved, and expression of glutamine at this site in murine Abs is somewhat unusual. Similarly, glutamic acid→glutamine is a non-conservative difference for buried amino acids, H39 is a potential $V_K$ contact residue, and glutamic acid is somewhat unusual in murine mAbs. Residue H48 is in close proximity to HCDR2 and H91 is predicted to be a high risk site (Studnicka (1994), supra; Harris, L. et al., (1995) Prot. Sci. 4:306–310) that potentially contacts the $V_K$ domain. Thus, both murine and human residues were expressed at H38, 39, 48, and 91 (FIG. 15, asterisks).

In summary, the framework library consisted of murine CDRs grafted into the human templates. In addition, one framework residue on the L chain and seven framework residues on the H chain were deemed potentially important for maintaining the activity of the mAb. All of these sites were characterized by synthesizing a combinatorial library that expressed all possible combinations of the murine and human amino acids found at these residues. The total diversity of this library, termed Hu I, was $2^8$ or 256 variants (Table 2 below).

TABLE 2

Summary of phage-expressed anti-CD40 antibody libraries.

| Library | Library Positions | Size* | Screened† |
|---|---|---|---|
| Hu I | Framework | 256 | $2.4 \times 10^3$ |
| Hu II | framework, HCDR3 | $1.1 \times 10^5$ | $2.0 \times 10^6$ |
| Hu III | framework, HCDR3, LCDR3 | $3.1 \times 10^7$ | $5.5 \times 10^5$ |

*Number of unique clones based on DNA sequence. Thirty-two codons are used to encode all 20 amino acids at each CDR position.
†The Hu I library was screened by ELISA using antibodies expressed in small-scale bacterial cultures (Watkins (1997), supra). The Hu II and Hu III libraries were plated on XL-1 Blue/agar lawns at $10^5$ plaques per 100-mm dish and were screened by capture lift (Watkins (1998), supra).

The Hu I library was expressed in small-scale (<1 ml) bacterial cultures, uniform quantities of Fab released from the periplasmic space were captured in a microtiter plate, and the binding activity of the antibodies was compared directly by ELISA (Watkins (1997), supra). Although variants that bind the target antigen with affinities comparable to, or better than, the chimeric Fab were identified, the majority of Hu I clones screened were less active than the chimeric anti-CD40 Fab. Approximately 6% of randomly selected Hu I variants displayed binding activities comparable to the chimeric Fab (data not shown). The identification of multiple Hu I variants with activity comparable to the chimeric CD40 is consistent with the interpretation that the most critical framework residues were included in the combinatorial library.

Figure 16:
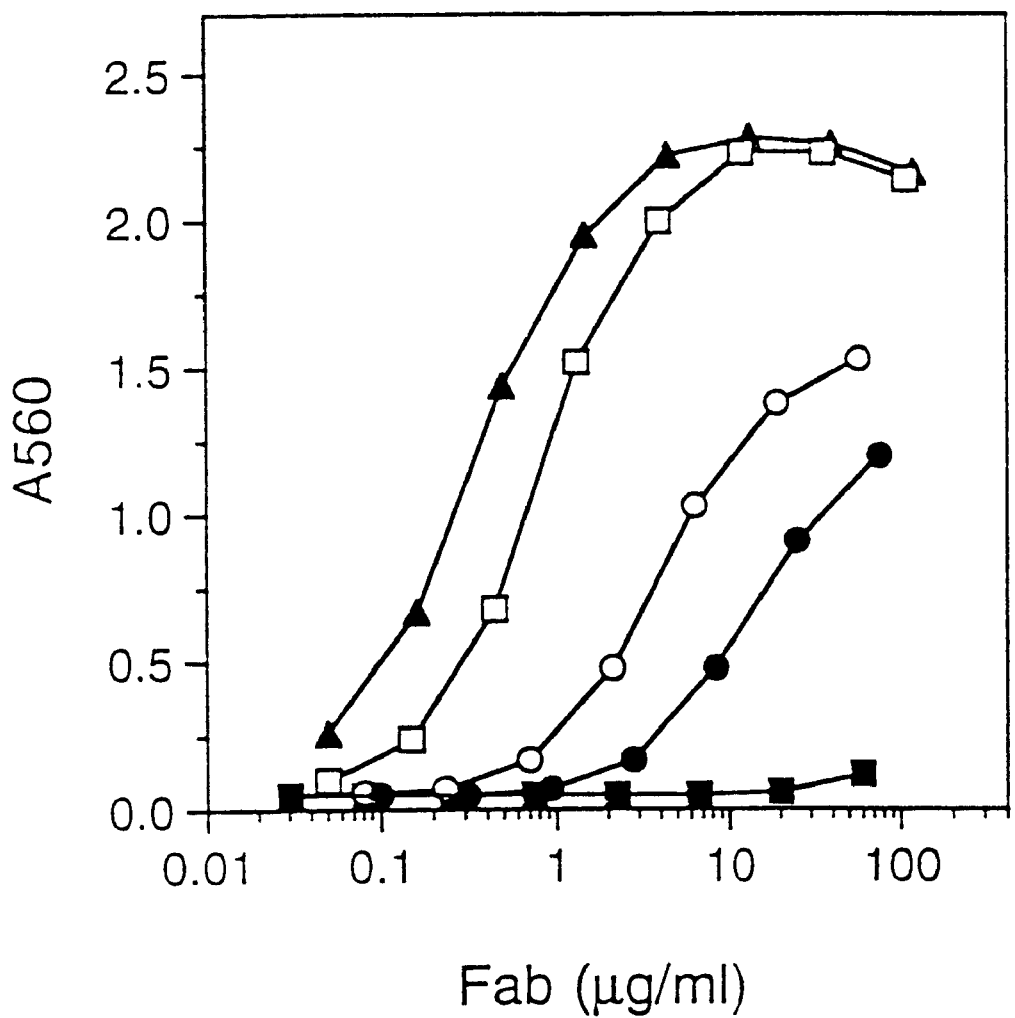
FIG. 16 shows the results of titration of humanized anti-CD40 variants on immobilized antigen. Bacterially-expressed chimeric anti-CD40 Fab and select variants from each of the libraries were characterized. Chimeric (filled circles), Hu I-19C11 (open circles), Hu II-CW43 (open squares), Hu III-2B8 (filled triangles), and an irrelevant (filled squares) Fab were released from the periplasmic space of 15 ml bacterial cultures and serial dilutions were incubated with CD40-Ig antigen immobilized on microtiter plates. Antibody binding was quantitated as described below.

Active clones were characterized firther by titration on immobilized antigen, confirming the identification of multiple variants with enhanced affinity. For example, clone 19C11 binds the CD40 receptor with higher affinity than the chimeric Fab, as demonstrated by the shift in the titration profile (FIG. 16, open circles vs. filled circles). DNA sequencing of 34 of the most active clones led to the identification of 24 unique framework combinations, each containing 2–6 murine framework residues (data not shown).

LCDR3 and HCDR3 contact antigen directly, interact with the other CDRs, and often affect the affinity and specificity of antibodies significantly (Wilson, I. A., et al., (1993) Curr. Opin. Struct. Biol. 3:113–118; Padlan, E. A. (1994) Mol. Immunol. 31:169–217). In addition, the conformation of LCDR3 and HCDR3 are determined in part by certain framework residues. To identify the most active antibody, codon-based mutagenesis (Glaser, S. M., et al., (1992) J. Immunol. 149:3903–3913) was used to synthesize oligonucleotides that introduce mutations at every position in HCDR3, one at a time, resulting in the expression of all 20 amino acids at each CDR residue. Each oligonucleotide encoded no more than a single amino acid alteration. The pool of oligonucleotides encoding the HCDR3 library was mixed with the overlapping oligonucleotides encoding the combinatorial framework and other CDRs to generate a framework/HCDR3 library. The diversity of this library, termed Hu II, was $1.1 \times 10^5$ (Table 2, above). A library for LCDR3 was synthesized in a similar manner. Oligonucleotides encoding the LCDR3, HCDR3, and the combinatorial framework were used to create a framework/HCDR3/LCDR3 library, termed Hu III. The large number of framework/CDR3 combinations resulted in a library with a complexity of $3.1 \times 10^7$ (Table 2, above).

Combining mutations in LCDR3 and/or HCDR3 with the framework library increased the potential diversity of humanized anti-CD40 variants from 256 to greater than $10^7$. In order to screen these larger libraries more efficiently a modified plaque lift assay, termed capture lift, was used (Watkins (1998), supra). Briefly, phage-infected bacteria were plated on solid agar lawns and subsequently, were overlaid with nitrocellulose filters that had been coated with a Fab-specific reagent. Following the capture of nearly uniform quantities of phage-expressed Fab the filters were probed with 5 ng/ml CD40-Ig fusion protein. Because the filters were probed with antigen at a concentration substantially below the Kd of the Fab, only variants displaying enhanced affinity were detectable. Multiple clones displaying higher affinities were identified following the screening of >$10^6$ variants from Hu II and >$10^5$ variants from the Hu III library using 82-mm filters containing ≈$10^5$ variants per filter (Table 2).

Because of the high phage density on the filters, positive plaques were picked, replated at a lower density, and screened again. Subsequently, the variants producing the most intense colorimetric signal in the capture lift assay were further characterized by ELISA. As expected, the majority of clones identified by capture lift screening bound CD40 better than the chimeric Fab. Titration of the variants on immobilized CD40-Ig identified multiple clones displaying affinities greater than the chimeric and humanized Fab (FIG. 16, compare open squares and filled triangles with circles).

The framework/CDR mutations that conferred enhanced affinity were identified by DNA sequencing. Unique variable region sequences were identified in 10/13 Hu II variants and ¾ Hu III variants. Both the Hu II and Hu III variants contained 1–5 murine framework residues and 0–2 CDR3 mutations, as summarized in Table 3 below.

TABLE 3

Simultaneous optimization of framework and CDR residues identifies higher affinity variants.

| Library | Clone | Murine Framework Residues* | CDR Mutations |
|---|---|---|---|
|  | chimeric | (43) | 0 |
| HuI | 19C11 | (2) H28, 48 | 0 |
| Hu II | CW43 | (3) H9, 28, 91 | HCDR3, $^{101}$A→R |
|  | 2B12 | (5) H9, 28, 38, 46, 48 | HCDR3, $^{101}$A→K |
| Hu III | 2B12 | (5) H9, 28, 38, 46, 48 | HCDR3, $^{101}$A→K |
|  | 2B8 | (1) H28 | HCDR3, $^{101}$A→K; LCDR3, $^{96}$R→Y |

*Number of murine framework residues that differ from the most homologous human germline sequence based on definition of CDRs of Kabat et al., supra. The number of murine framework residues differing from the human template is indicated in parentheses. All of the framework differences between the murine mAb and the humanized versions are located on the H chain (H) at the indicated positions using the numbering system of Kabat et al.

The affinities of bacterially-expressed chimeric Fab and select variants from each of the libraries were characterized more thoroughly using surface plasmon resonance measurements to determine the association and dissociation rates of purified Fab with immobilized CD40-Ig. Chimeric anti-CD40 had a dissociation constant $K_d$=3.14 nM and, consistent with the screening results, many of the variants displayed higher affinities. Two of the best clones, F4 and L3.17, had Kd of 0.24 nM and 0.10 nM, respectively (Table 1). The improved affinities of the anti-CD40 variants were predominantly the result of slower dissociation rates as the association rates were very similar for all of the variants (ranging from 0.9 to $3.2 \times 10^6$ $M^{-1}s^{-1}$).

Figure 17:
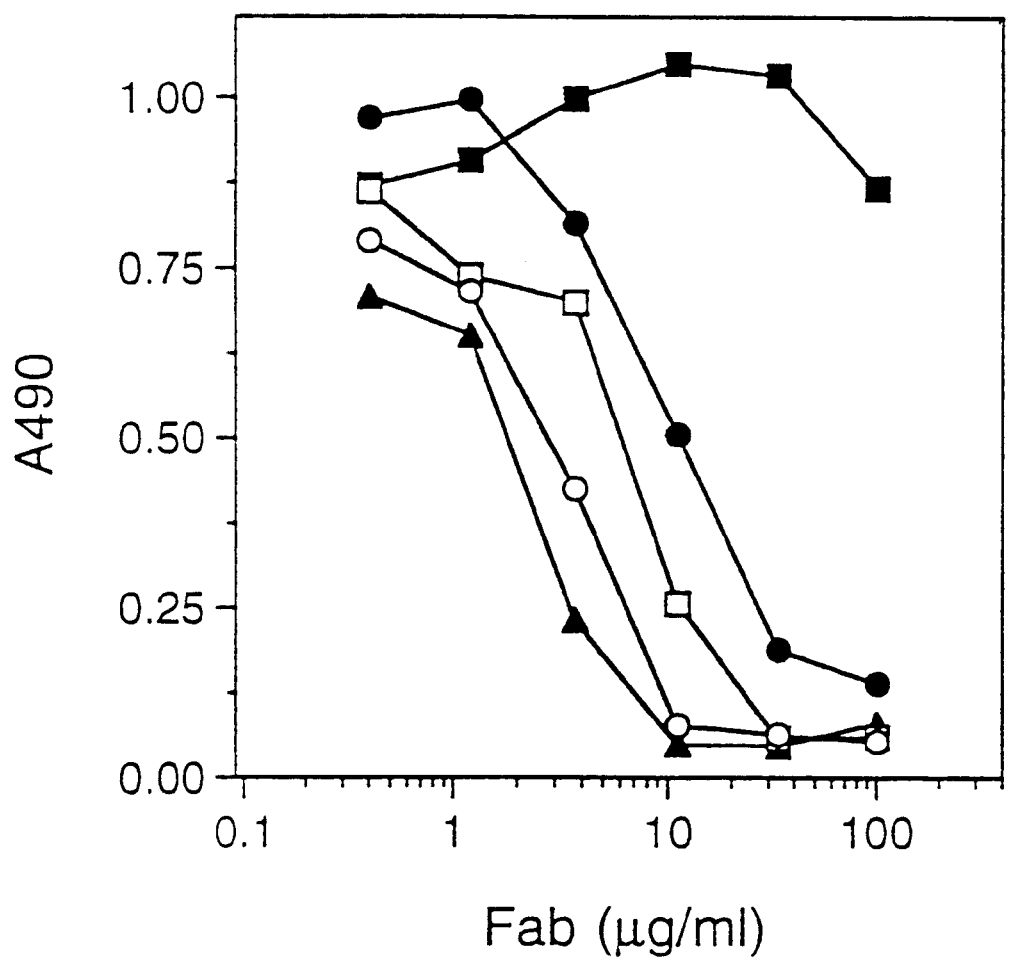
FIG. 17 demonstrates how antibody affinity correlates with the inhibition of soluble-gp39 binding to CD40-Ig. The ligand for the CD40 receptor, gp39, was captured in a microtiter plate. Subsequently, varying amounts of purified chimeric (filled circles), Hu II-CW43 (open squares), Hu III-2B8 (filled triangles), HuII/III-2B12 (open circles), and irrelevant (filled squares) Fab were co-incubated with 2 µg/ml CD40-Ig on the microtiter plate. Binding of CD40-Ig to gp39 was quantitated as described below.
Figure 18A:
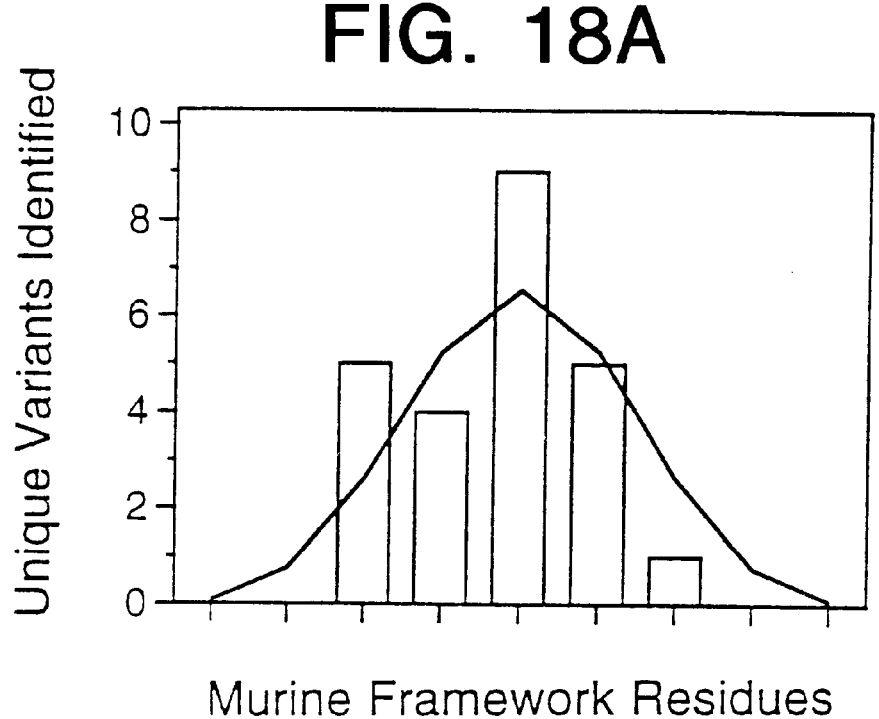
FIG. 18 shows the quantitation of murine framework residues in active variants. The variable regions of the most active anti-CD40 variants from the framework optimization library Hu I (A) and from the framework/HCDR3 optimization library Hu II (B) were sequenced to identify the amino acids at framework library positions. Each unique variant was categorized based on the total number of murine residues retained at the 8 framework library positions. Thirty-four clones from the Hu I library and fourteen clones from the Hu II library were sequenced, leading to the identification of 24 and 10 unique variants, respectively. The solid line indicates the sequence distribution expected from an equal number of randomly selected variants.
Figure 18B:
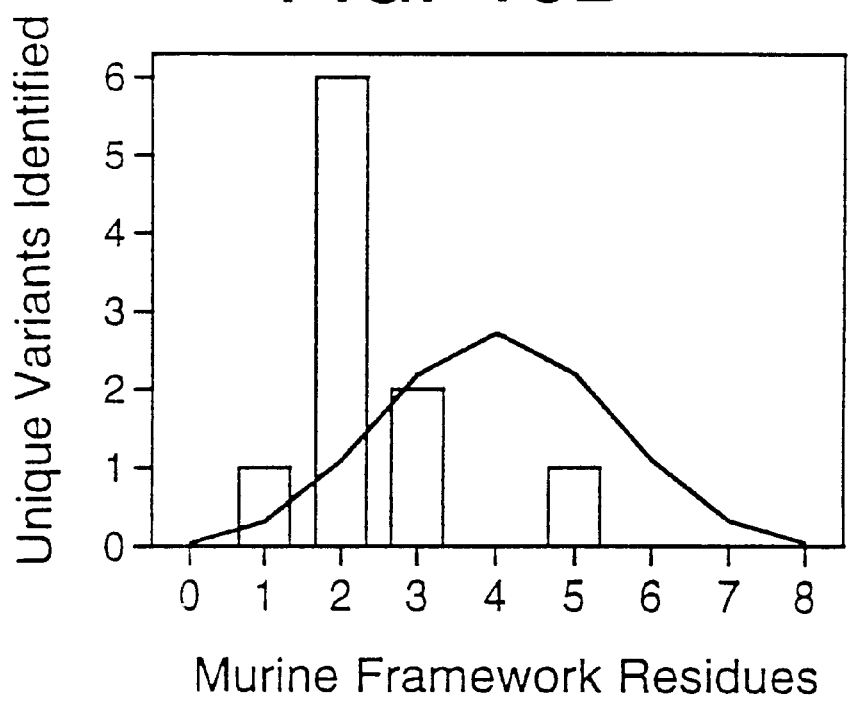

Finally, the variants displaying enhanced affinity were tested for their ability to block the binding of gp39 ligand to the CD40 receptor. The variants all inhibited the binding of soluble CD40-Ig fusion protein to immobilized gp39 antigen in a dosedependent manner that correlated with the affinity of the Fabs (FIG. 17). For example, the most potent inhibitor of ligand binding to CD40-Ig fusion protein was variant 2B8, which was also the variant with the highest affinity for CD40 (FIG. 17). Variant 2B8 displayed ≈17-fold higher affinity for CD40 than did the chimeric Fab and inhibited ligand binding ≈7-fold more effectively.

EXAMPLE 5

Mouse Model System

Applicants also developed and tested in vivo a rat anti-murine CD40 mAb designated 7E1-G2b and its predecessor, 7E1-G1. The generation of this antibody was performed in order to explore the potential of anti-CD40 therapy in murine models of autoimmune, inflammatory and transplant disease. The primary objective of the mouse model system was to generate an anti-murine counterpart that mimicked 2.220's complete and potent blockade of gp39/CD40 interaction while possessing weak costimulatory activity, and test it in vivo in standard experimental disease models.

A. Isolation and Characterization of Anti-Murine CD40 Monoclonal Antibodies 7E1-G1 and 7E1-G2b 1. Immunization, Fusion and Characterization A recombinant murine CD40 immunoglobulin fusion protein consisting of the extracellular region of mouse CD40 fused to the hinge, CH2 and CH3 domains of a mouse IgG2a antibody (mCD40-mIg) was used to immunize an 8 week old female Lewis rat via footpad inoculation. Three days following the last immunization, leukocytes from the draining lymph nodes were fused with X63-Ag8.653 mouse myeloma cells to create rat x mouse heterohybridomas. Wells containing antibody specific for native mouse CD40 were identified for reactivity with the original mCD40-mIg immunogen by ELISA, and for reactivity with a CD40 positive mouse B cell lymphoma cell line (WEHI-231, ATCC CRL-1702). Supernatants were then tested for the ability to inhibit the binding of mCD40-mIg to soluble, recombinant mCD8-murine gp39 fusion protein, mgp39, the murine equivalent of sgp39. Approximately twelve of the most potent inhibitor master wells were cloned by a limiting dilution method.

Following cloning, finctional assays were performed with culture supernatants and purified antibody in order to more accurately assess the ability of the anti-CD40 mAbs to inhibit the interaction of murine gp39 with CD40 and to determine their stimulatory properties. Inhibitory properties were measured by the ability to inhibit the binding of mgp39 to WEHI-231 using standard procedures known in the art. Stimulatory properties were measured by the induction of tight, homotypic adhesion of WEHI-231 cells and the proliferation of splenic B cells in the presence of the antibody and anti-IgM using procedures known in the art. From these results, three mAbs (5A3, 7E1-G1 and 8E1) were determined to be most like the anti-human CD40 mAb 2.220 with respect to gp39/CD40 blockade and level of costimulatory activity.

2. Selection of 7E1 as the Lead Anti-Murine CD40 mAb

In vivo studies in mice were aimed at identifying which of the blocking/non-stimulatory anti-CD40 mAbs most potently suppressed specific antibody responses to a T-dependent antigen. Suppression of the IgG antibody response to SRBCs in mice with anti-murine CD40 mAb was studied. Groups of five BALB/c mice were immunized IV with $1 \times 10^8$ SRBCs and concurrently treated ip with 1 mg of antimurine CD40 mAbs 5A3, 7E1-G1 or 8E1. As controls, groups of similarly immunized mice were treated with MR1 (hamster anti-murine gp39, positive control, 250 ug), 6E9 (rat anti-human gp39, negative control, 1 mg) or PBS. Mice were evaluated for IgG anti-SRBC titers by ELISA on days 7, 14, 21 and 35. The results indicated that when administered as a single dose of antibody at the time of antigen challenge with SRBCs, mAb 7E1-G1 was shown to be a more effective suppressor of the IgG anti-SRBC response compared to mAbs 5A3 or 8E1, and was therefore selected as the lead anti-CD40 mAb for murine studies.

3. Isotype Switch Variant of mAb 7E1-G1

7E1-G1 did not possess effector function characteristics comparable to that of the chimeric 2.220 anti-human CD40 mAb (i.e., rat IgG1 is not as efficient as human IgG1 at complement fixation and Fc receptor interaction) and the profile of specific antibody suppression in vivo for 7E1 was not as complete as that seen with the 2.220 mAb in primates. Thus, an antibody having 7E1 specificity but with a rat isotype more like human IgG1 in its effector capabilities was sought. To this end, a natural isotype switch variant of 7E1, from an IgG1 to an IgG2b, was generated by the sib-selection technique (Hale et al., *J. Immunol. Methods* (1987) 103(l):59–67). Briefly, an anti-CD40 mAb of the IgG2b isotype was identified by ELISA among supernatants of 96 well plates that had been seeded at 1000 cells/well with the original 7E1 hybridoma. Subsequent rounds of plating and identification of IgG2b positive wells at seeding densities of 200 and then 20 cells/well followed by two rounds of cloning by limiting dilution led to the isolation of a clonal IgG2b switch variant of 7E1, 7E1-G2b.

7E1-G2b is a legitimate switch variant of the IgG1 as demonstrated by three sets of data. First, N-terminal sequencing of the heavy chain showed that both versions were identical for the first 35 amino acid residues. Second, PCR analysis using primers specific for the variable heavy chain CDRs of 7E1-G1 yielded a band of appropriate size from cDNA obtained from either 7E1-G1 or 7E1-G2b, and not two other unrelated antibodies. Lastly, assessment of binding activity of purified lots of the two versions to immobilized mCD40-hIg in an ELISA using an anti-kappa tracer reagent yielded essentially identical titration curves.

B. In Vivo Studies

1. In Vivo Comparison of 7E1-G1 to 7E1-G2b in Antibody Response Model

Figure 10A:
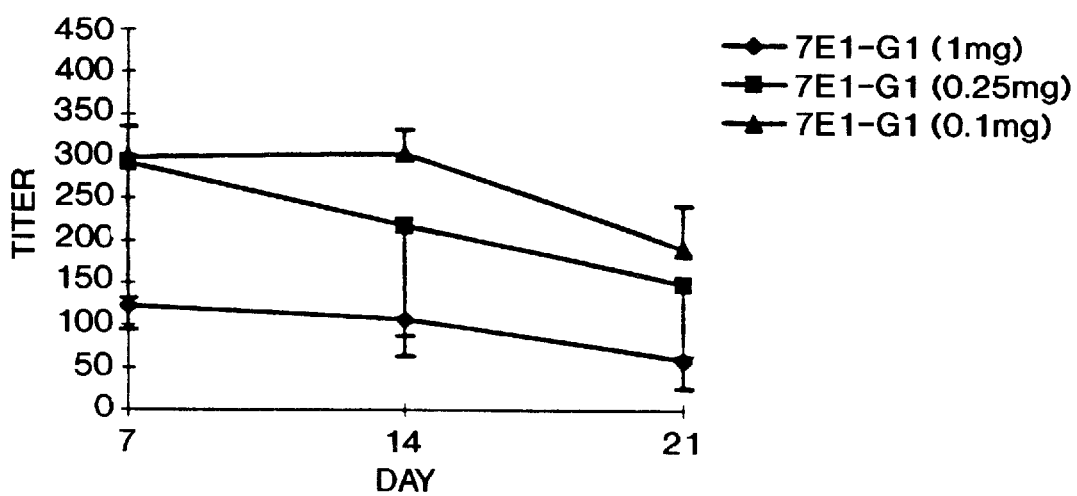
FIG. 10 shows a comparison of the ability of antibody 7E1-G1 and 7E1-G2b to suppress an IgG antibody response to SRBC.
Figure 10B:
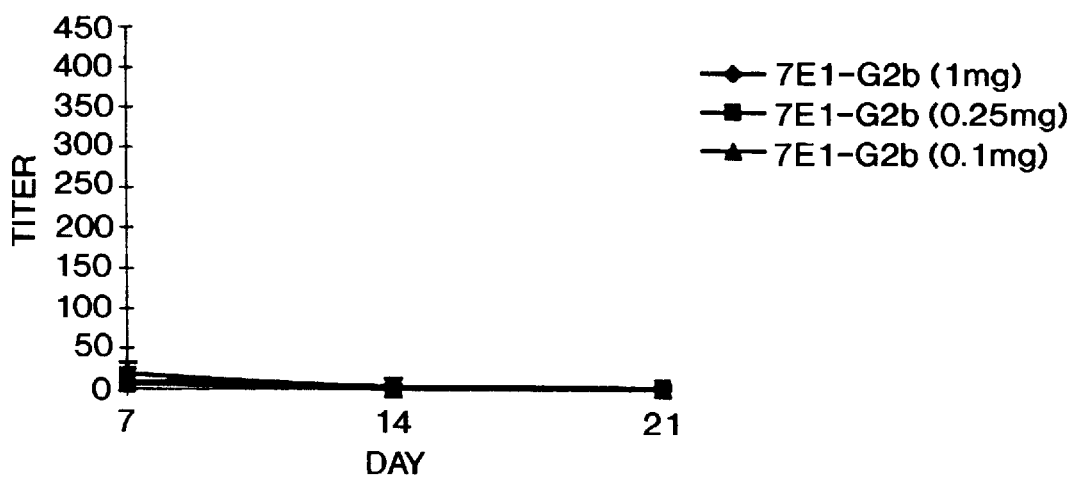
Figure 10C:
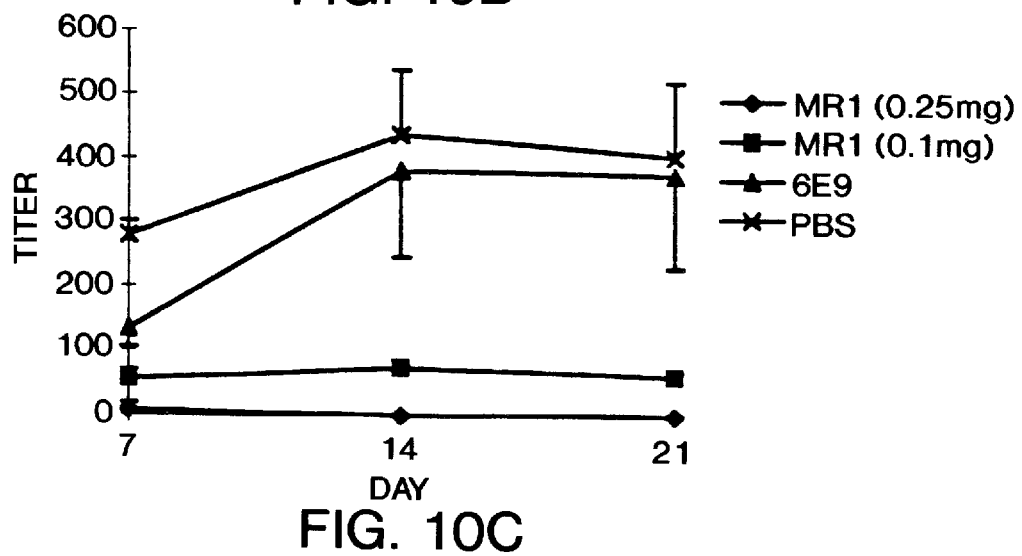

7E1-G1 was compared to 7E1-G2b for efficacy in vivo using SRBC's as the T cell dependent antigen. Groups of three to five animals were immunized iv with SRBC and concurrently treated ip with the antibody 7E1-G1 or 7E1-G2b, at 1, 0.25, or 0.1 mg of compound on day 0 as indicated in FIG. 10. Anti-murine gp39 mAb MR1 served as a positive control for immunosuppressive effect. MAb 6E9 and PBS served as irrelevant mAb and no mAb controls, respectively. Mice were evaluated for anti-SRBC titers by ELISA on days 7, 14 and 21. Titer represents the calculated dilution of serum to yield an OD value =0.3 in the ELISA. As shown in FIG. 10, 7E1-G2b suppressed the IgG response to SRBCs at doses where the 7E1-G1 did not.

2. 7E1-G2b Dose Response in T-dependent Antigen Mouse Model

Figure 11:
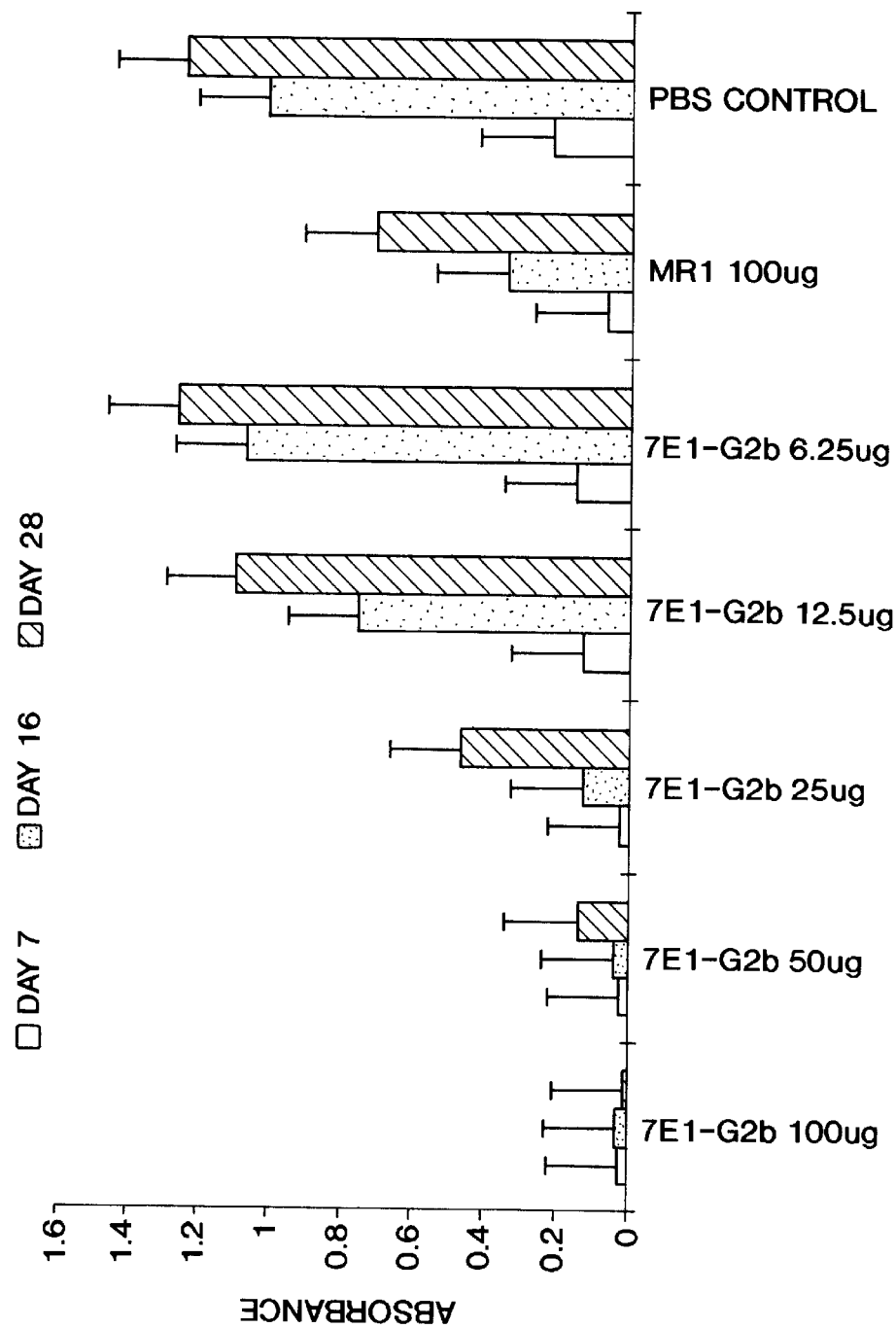
FIG. 11 shows the dose response of inhibition of antibody response to SRBC with 7E1-G2b.

7E1-G2b was examined in a T cell dependent primary immune response model using SRBC as the antigen. 7E1-G2b was tested at various doses to determine the lowest effective dose. BALB/c mice (n=5) were injected IV with $1 \times 10^8$ SRBCs and treated with a single injection of 7E1-G2b at the indicated doses or MR1 (anti-murine gp39) or PBS administered at the same time as the antigen on day 0. Shown in FIG. 11 is the IgG anti-SRBC response on days 7, 16 and 28. Values reported are the ELISA absorbance value at a serum dilution of 1/50. Error bars indicate standard deviation.

As shown in FIG. 11, a single treatment with 7E1-G2b at 25 µg/mouse (1.25 mg/kg) suppressed the IgG immune response by 87% on Day 16 and complete suppression was obtained with 50 or 100 µg doses at Day 16. At Day 28, 50 µg/mouse suppressed the IgG response by 89%, and 100 µg/mouse suppressed completely. Note that MR1 was used as a positive control for immunosuppression at a suboptimal dose of 100 µg/mouse.

3. 7E1-G2b in Preventative Collagen-Induced Arthritis (CIA) Mouse Model

A standard experimental murine model for rheumatoid arthritis, the collagen-induced arthritis model (CIA), was used to determine the effect of 7E1-G2b on prevention of arthritis. DBA/1J male mice (6–8 weeks) were injected with 200 ug of chicken collagen type II (CII) in complete Freund's adjuvant intradermally on day 0. Treatment with 7E1-G2b at 250 μg/dose was administered IP every 4 days starting on day 7. The control group was treated with PBS on the same dosing schedule. All mice were boosted with CII in incomplete Freund's adjuvant on day 21. Mice were observed daily for paw swelling and subjectively scored on a scale of 0–3 with 3 equal to maximum swelling and erythema. Paws were also measured with calipers daily. The clinical score reported was derived by summation of the score of each paw at the time of sacrifice and dividing by the total number of animal in each group. The values reported are the median range of the groups.

Arthritis development, and hence joint inflammation in the mice, was completely inhibited by therapy with 7E1-G2b as shown in Table 4 below. Mice treated with 7E1-G2b were completely free of disease through 90 days.

TABLE 4

Treatment of Collagen-Induced Arthritis

| Tx Group | Arthritis Incidence | Median (Range) Day of onset | Median (Range) Clinical score | Median (Range) Paw measure |
| --- | --- | --- | --- | --- |
| 7E1-G1 | 0/5 | 0 | 0 | 0.075 |
| 7E1-G2b | 0/5 | 0 | 0 | 0.075 |
| PBS control | 4/4 | 30 (27–32) | 3.5 (3–4) | 0.114 (0.110–0.117) |

As demonstrated above, the antibodies of the present invention are potent immunomodulators, with therapeutic uses against a variety of disease.

The present invention encompasses chimeric and humanized antibodies as described above with additional conservative amino acid substitutions which have substantially no effect on CD40 binding. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

In one aspect, the present invention is directed to producing the chimeric and/or humanized antibodies as described above by expressing recombinant DNA segments encoding the murine light variable chain and heavy variable chain (or portions thereof), attached to DNA segments encoding the human constant regions. Exemplary DNA sequences designed in accordance with the present invention code for the polypeptide chains comprising all or a portion of the light chain variable region as shown in SEQ ID NO: 1 or its deposited ATCC clone, and/or all or a portion of the heavy chain variable region as shown in SEQ ID NO:2 or its deposited ATCC clone.

Also encompassed within the present invention are the disclosed heavy and light chain variable regions and active or finctional parts thereof. The immunologically competent or functional form of the protein or part thereof is also referred to herein as a "light/heavy chain variable region or biologically active portion thereof". In the present case, a biologically active portion thereof comprises a portion of said light or heavy chain which, when incorporated into an antibody, still permits the antibody to bind to human CD40.

Specifically encompassed within the present invention are nucleic acid sequences encoding the variable heavy chain and the variable light chain of an antibody of the present invention. For example, nucleotides 1057 through 1422 (SEQ ID NO:13) of FIG. 13 (SEQ ID NO:5) provide a preferred nucleic acid sequence encoding a variable heavy chain of an antibody of the present invention; nucleotides 1065 through 1388 (SEQ ID NO:14) of FIG. 14 (SEQ ID NO:6) provide a preferred nucleic acid sequence encoding a variable light chain of an antibody of the present invention. SEQ ID NO:7 and SEQ ID NO:11 show preferred nucleic acid sequences encoding variable light chains of humanized antibodies of the present invention; SEQ ID NO:9 shows a preferred nucleic acid sequence encoding a variable heavy chain of a humanized antibody of the present invention. Plasmids comprising the polynucleotides shown in SEQ ID NO:7, SEQ ID NO:9 and SEQ ID NO:11 have been deposited with the ATCC.

Chimeric and/or humanized antibodies that bind to human CD40 and that comprise polypeptides that are substantially homologous to, or that show substantial sequence identity to, the variable light and heavy chain sequences disclosed herein are also contemplated by the present invention. For example, chimeric antibodies comprising a light chain region that exhibits at least about 85% sequence identity, more preferably at least about 90% sequence identity, even more preferably at least about 95% sequence identity, and most preferably at least about 98% sequence identity with the light chain region as shown in SEQ ID NO:4 are included within the scope of the present invention. More particularly, chimeric antibodies comprising a variable light chain region that exhibits at least about 85% sequence identity, more preferably at least about 90% sequence identity, even more preferably at least about 95% sequence identity, and most preferably at least about 98% sequence identity with the variable light chain region as shown in SEQ ID NO:1 are also included within the scope of the present invention. Also within the scope of the present invention are humanized antibodies comprising a light chain region that exhibits at least about 85% sequence identity, more preferably at least about 90% sequence identity, even more preferably at least about 95% sequence identity, and most preferably at least about 98% sequence identity with the light chain region as shown in SEQ ID NO:8 and/or SEQ ID NO:12.

Additionally, chimeric antibodies comprising a heavy chain region that exhibits at least about 85% sequence identity, more preferably at least about 90% sequence identity, even more preferably at least about 95% sequence identity, and most preferably at least about 98% sequence identity with the heavy chain region as shown in SEQ ID NO:3 are included within the scope of the present invention. More particularly, chimeric antibodies comprising a variable heavy chain region that exhibits at least about 85% sequence identity, more preferably at least about 90% sequence identity, even more preferably at least about 95% sequence identity, and most preferably at least about 98% sequence identity with the variable heavy chain region as shown in SEQ ID NO:2 are also included within the scope of the present invention. Additionally, humanized antibodies comprising a variable heavy chain region that exhibits at least about 85% sequence identity, more preferably at least about 90% sequence identity, even more preferably at least about 95% sequence identity, and most preferably at least about 98% sequence identity with the variable heavy chain region as shown in SEQ ID NO:10 are also included within the scope of the present invention.

The DNA segments typically further comprise an expression control DNA sequence operably linked to the chimeric or humanized antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into an appropriate host the host is maintained under conditions suitable for high level expression of the nucleotide sequences and, as desired, the collection and purification of the variable light chain, heavy chain, light/heavy chain dimers or intact antibody, binding fragments or other immunoglobulin form may follow. (See, Beychok, S., "Cells of Immunoglobulin Synthesis", Academic Press, N.Y. (1979)). Single chain antibodies may also be produced by joining nucleic acid sequences encoding the VL and VH regions disclosed herein with DNA encoding a polypeptide linker.

Prokaryotic hosts, such as *E. coli*, and other microbes, such as yeast, may be used to express an antibody of the present invention. In addition to microorganisms, mammalian tissue cell culture may also be used to express and produce the antibodies of the present invention. Eukaryotic cells may be preferred, because a number of suitable host cell lines capable of secreting intact immunoglobulins have been developed in the art, and include the CHO cell lines, various COS cell lines, HeLa cells, myeloma cell lines, and hybridomas. Expression vectors for these cells can include expression control sequences, such as a promoter or enhancer, and necessary processing information sites, such as ribosome binding sites, RNA splice sites, polyadenylation sites, and transcriptional terminator sequences, all known in the art.

The vectors containing the DNA segments of interest (e.g., the heavy and/or light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, e.g., Maniatis, et al., "Molecular Cloning: A Laboratory Manual", Cold Spring Harbor Press (1982)).

Once expressed, the whole antibodies, their dimers, individual light and heavy chains, or other immunoglobulin forms of the present invention, can be purified according to standard procedures in the art, including ammonium sulfate precipitation, affinity columns, column chromatography, gel electrophoresis and the like. Substantially pure immunoglobulins of at least 90 to 95% homogeneity are preferred, and 98 to 99% or more homogeneity are most preferred, for pharmaceutical uses.

The antibodies of the present invention will typically find use in treating antibody mediated and/or T cell mediated disorders. Typical disease states suitable for treatment include graft versus host disease and transplant rejection, and autoinmune diseases such as Type I diabetes, psoriasis, multiple sclerosis, rheumatoid arthritis, systemic lupus erythematosus, and myesthenia gravis.

The antibodies and pharmaceutical compositions of the present invention are particularly useful for parenteral administration, i.e., subcutaneously, intramuscularly or intravenously. The pharmaceutical compositions for parenteral administration will commonly comprise a solution of the antibody dissolved in an acceptable carrier, preferably an aqueous carrier. A variety of aqueous carriers can be used, all well known in the art, e.g., water, buffered water, saline, glycine and the like. These solutions are sterile and generally free of particulate matter. These pharmaceutical compositions may be sterilized by conventional well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, human albumin, etc.

The compositions containing antibodies of the present invention can be administered for prophylactic and/or therapeutic treatments. In therapeutic application, compositions are administered to a patient already suffering from a disease, in an amount sufficient to cure or at least partially arrest the disease and its complications. An amount adequate to accomplish this is defined as a "therapeutically effective dose". Amounts effective for this use will depend upon the severity of the disease state and the general state of the patient's own immune system, and can be determined by one skilled in the art.

In prophylactic applications, compositions containing antibodies of the present invention are administered to a patient not already in the disease state to enhance the patient's resistance (suppress an immune response). Such an amount is defined to be a "prophylactically effective dose". In this use, the precise amounts again depend upon the patient's state of health and general level of immunity. A preferred prophylactic use is for the prevention of transplant rejection, e.g., kidney transplant rejection.

Although the present invention has been described in some detail by way of illustration and example for purposes of clarity and understanding, it will be apparent that certain changes and modifications may be practiced within the scope of the appended claims.

We claim:

1. A light chain variable region comprising an amino acid sequence as shown in SEQ ID NO:8.
2. A heavy chain variable region comprising an amino acid sequence as shown in SEQ ID NO:10.
3. A light chain variable region comprising an amino acid sequence as shown in SEQ ID NO:12.
4. A light chain variable region comprising a nucleic acid sequence as shown in SEQ ID NO:7.
5. A heavy chain variable region comprising a nucleic acid sequence as shown in SEQ ID NO:9.
6. A light chain variable region comprising a nucleic acid sequence as shown in SEQ ID NO:11.
7. A humanized antibody which binds to human CD40, comprising a light chain and a heavy chain, said light chain comprising the light chain variable region of SEQ ID NO:8 or an active portion of said antibody which binds to human CD40.
8. A humanized antibody of claim 7, wherein said light chain comprises the light chain variable region of SEQ ID NO:12 or an active portion of said antibody which binds to human CD40.
9. A humanized antibody of claim 7, further comprising a heavy chain variable region of SEQ ID NO:10 or an active portion of said antibody which binds to human CD40.
10. A humanized antibody of claim 8, further comprising a heavy chain variable region of SEQ ID NO:10 or an active portion of said antibody which binds to human CD40.
11. A humanized antibody comprising a portion of the light chain variable region of claim 1 or an active portion of said antibody which binds to human CD40.
12. A humanized antibody comprising a portion of the heavy chain of claim 2 or an active portion of said antibody which binds to human CD40.
13. A humanized antibody of claim 8 comprising a portion of the light chain of claim 3 or an active portion of said antibody which binds to human CD40.
14. The humanized antibody of claim 7 comprising a light chain variable region as shown in SEQ ID NO:8 and a heavy chain variable region as shown in SEQ ID NO:10.
15. The humanized antibody of claim 7 comprising a light chain variable region as shown in SEQ ID NO:12 and a heavy chain variable region as shown in SEQ ID NO:10.
16. A pharmaceutical composition comprising a humanized antibody of claim 14.
17. A pharmaceutical composition comprising a humanized antibody of claim 15.
18. A humanized antibody which binds to human CD40, comprising a light chain and a heavy chain, said light chain comprising the light chain deposited as Accession Number ATCC 203628.
19. A humanized antibody of claim 18, wherein said light chain comprises the light chain deposited as Accession Number ATCC 203774.
20. A humanized antibody of claim 18, further comprising a heavy chain deposited as Accession Number ATCC 203631.
21. A humanized antibody of claim 19, further comprising a heavy chain deposited as Accession Number ATCC 203631.
22. A humanized antibody of claim 7 comprising a light chain deposited as Accession Number ATCC 203628.

23. A humanized antibody of claim 7 comprising a heavy chain deposited as Accession Number ATCC 203631.

24. A humanized antibody of claim 7 comprising a light chain deposited as Accession Number ATCC 203774.

25. A recombinant DNA molecule that encodes a humanized antibody which binds to human CD40 or an active portion of said antibody which binds to human CD40 comprising a light chain deposited as ATCC Accession Number 203628 or ATCC Accession Number 203774.

26. A recombinant DNA molecule of claim 25 that further comprises a heavy chain deposited as Accession Number ATCC 203631.

* * * * *